US011285004B2

(12) United States Patent
Iversen et al.

(10) Patent No.: US 11,285,004 B2
(45) Date of Patent: Mar. 29, 2022

(54) VALVE REPAIR DEVICES AND PROCEDURES

(71) Applicant: Edwards Lifesciences Corporation, Irvine, CA (US)

(72) Inventors: Sven Benjamin Iversen, Bethesda, MD (US); Adam J. Yestrepsky, Lake Forest, CA (US); Amy E. Munnelly, Irvine, CA (US); Bin Tian, Irvine, CA (US); Danny Barrientos Baldo, Jr., San Diego, CA (US); Brian S. Conklin, Orange, CA (US); Louis A. Campbell, Santa Ana, CA (US); John Richard Carpenter, Santa Ana, CA (US); Derrick Johnson, Orange, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 148 days.

(21) Appl. No.: 16/430,334

(22) Filed: Jun. 3, 2019

(65) Prior Publication Data

US 2019/0380835 A1    Dec. 19, 2019

Related U.S. Application Data

(60) Provisional application No. 62/680,852, filed on Jun. 5, 2018.

(51) Int. Cl.
*A61F 2/24* (2006.01)
*A61B 17/00* (2006.01)
*A61B 17/04* (2006.01)
*A61B 17/30* (2006.01)

(52) U.S. Cl.
CPC ...... *A61F 2/2466* (2013.01); *A61B 17/00234* (2013.01); *A61B 17/0401* (2013.01); *A61B 17/0469* (2013.01); *A61B 2017/00243* (2013.01); *A61B 2017/00783* (2013.01); *A61B 2017/00867* (2013.01); *A61B 2017/0496* (2013.01); *A61B 2017/308* (2013.01)

(58) Field of Classification Search
CPC .................................. A61F 2/24; A61F 2/2466
See application file for complete search history.

(56) References Cited

U.S. PATENT DOCUMENTS

| 8,382,829 B1 | 2/2013 | Call et al. |
| 2005/0119735 A1 | 6/2005 | Spence et al. |
| 2010/0131057 A1* | 5/2010 | Subramanian ........ A61F 2/2445 623/2.36 |
| 2014/0094826 A1 | 4/2014 | Sutherland et al. |

* cited by examiner

*Primary Examiner* — Matthew W Schall
(74) *Attorney, Agent, or Firm* — Alan T. Hale; Chang & Hale

(57) ABSTRACT

A method for repairing a native valve of a patient during a non-open-heart procedure includes attaching two or more attachment members to the native valve. The method also includes applying a force to the two or more attachment members such that the two or more attachment members cause a cinching effect on at least a portion of the native valve. The method further includes securing the two or more attachment members with one or more anchor members such that the two or more attachment members maintain the cinching effect.

20 Claims, 61 Drawing Sheets

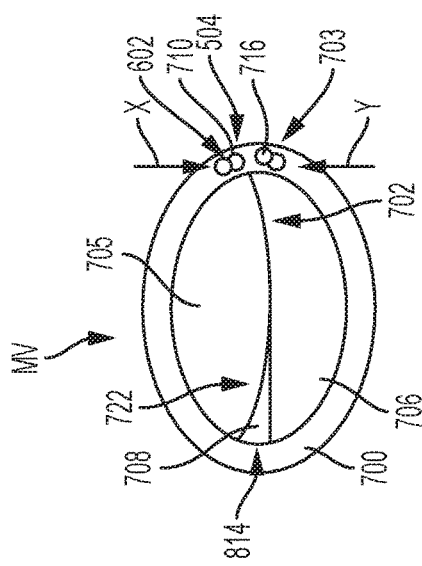
FIG. 7E
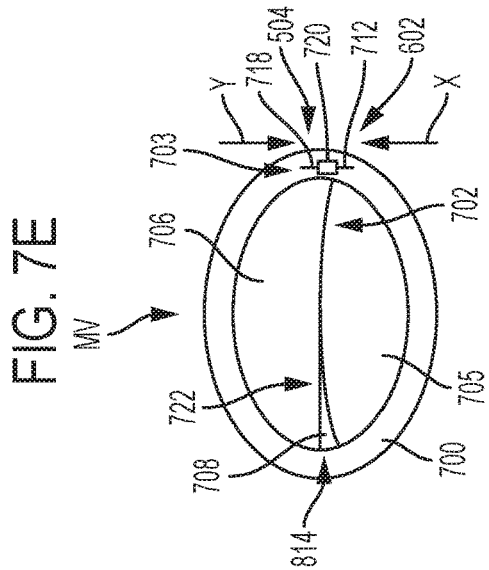
FIG. 7F
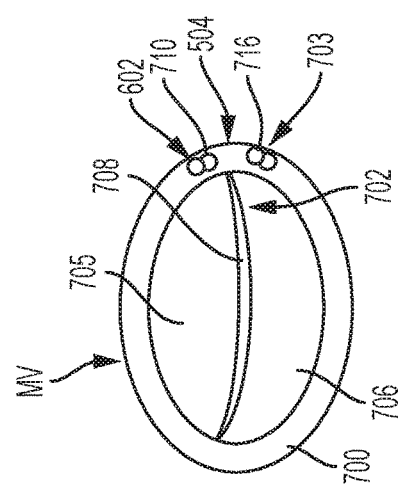
FIG. 7C
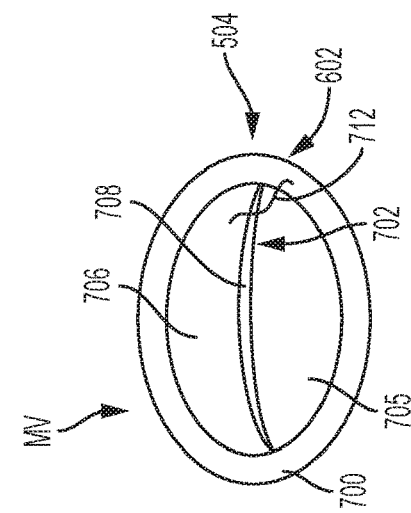
FIG. 7D
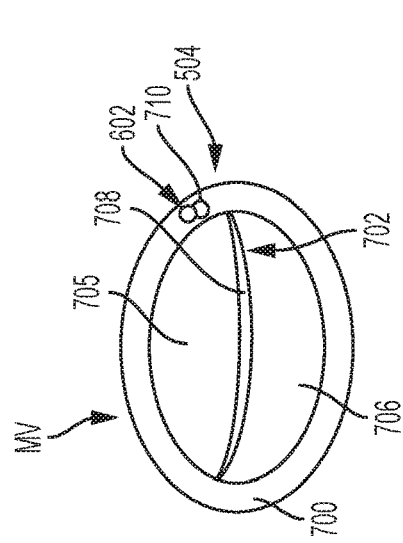
FIG. 7A
FIG. 7B

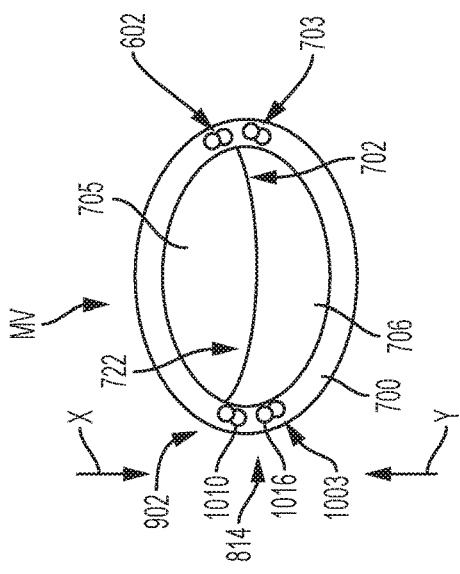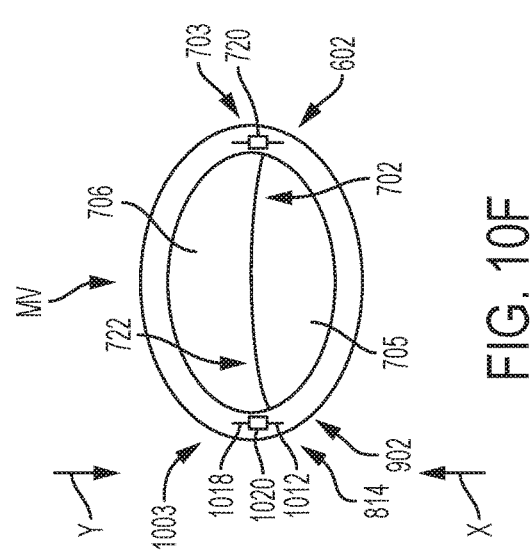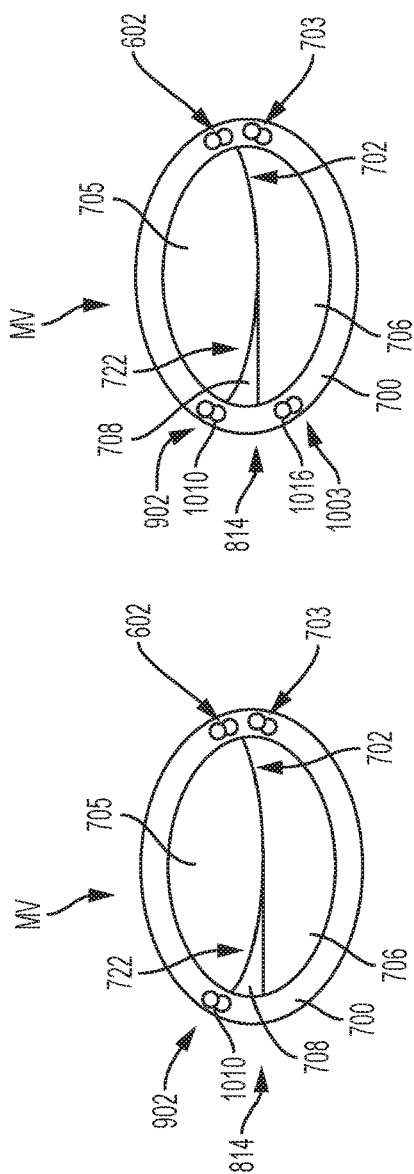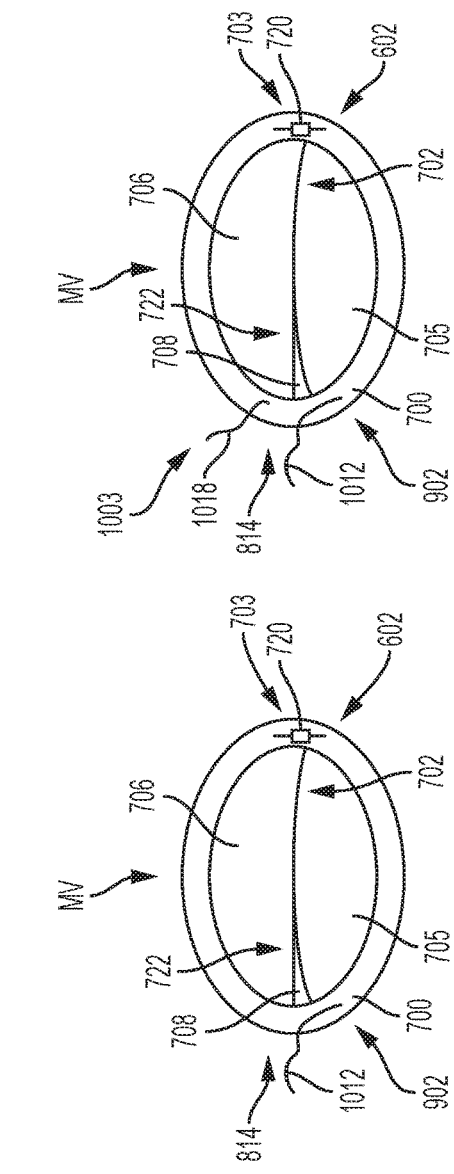

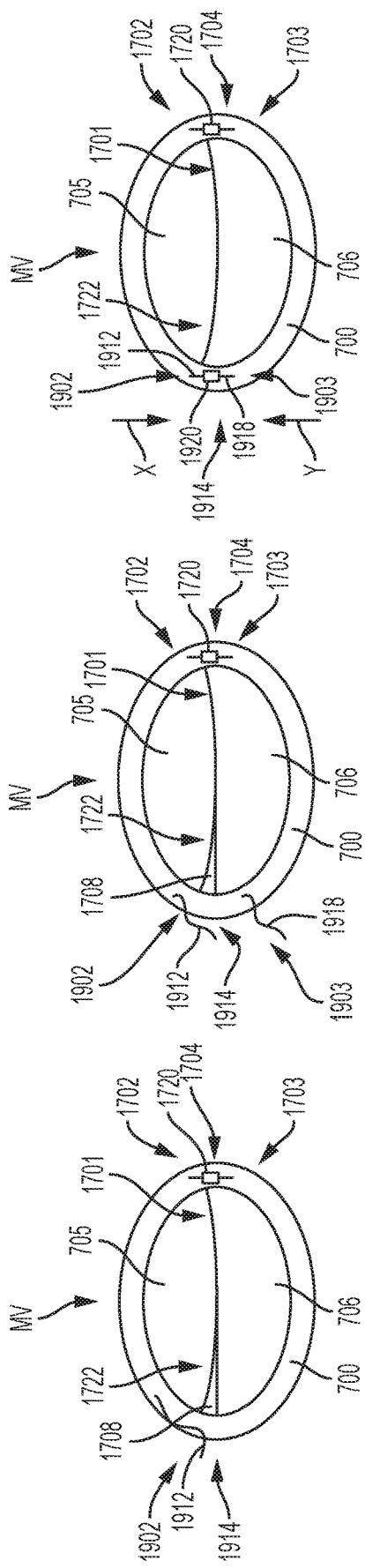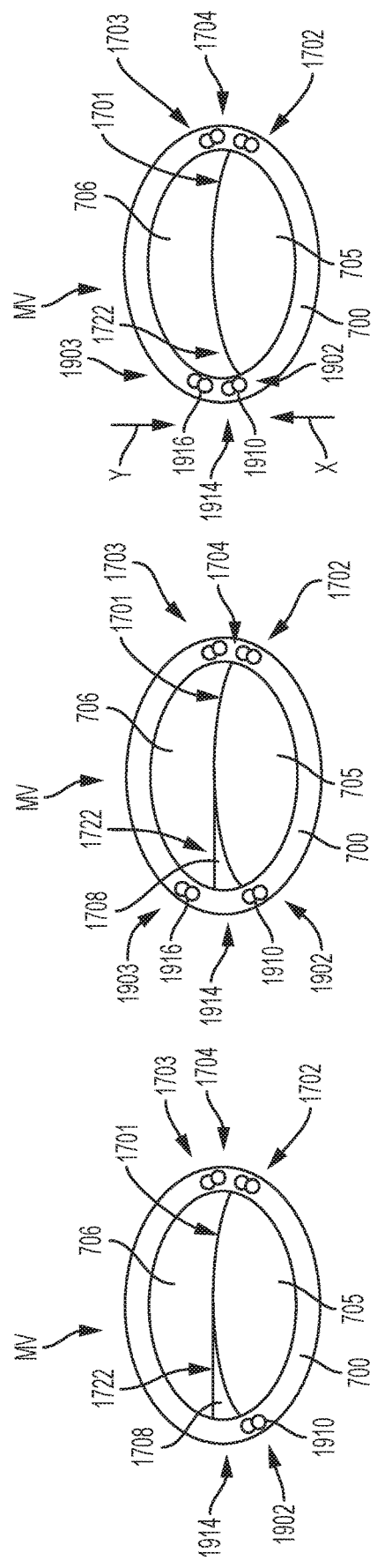

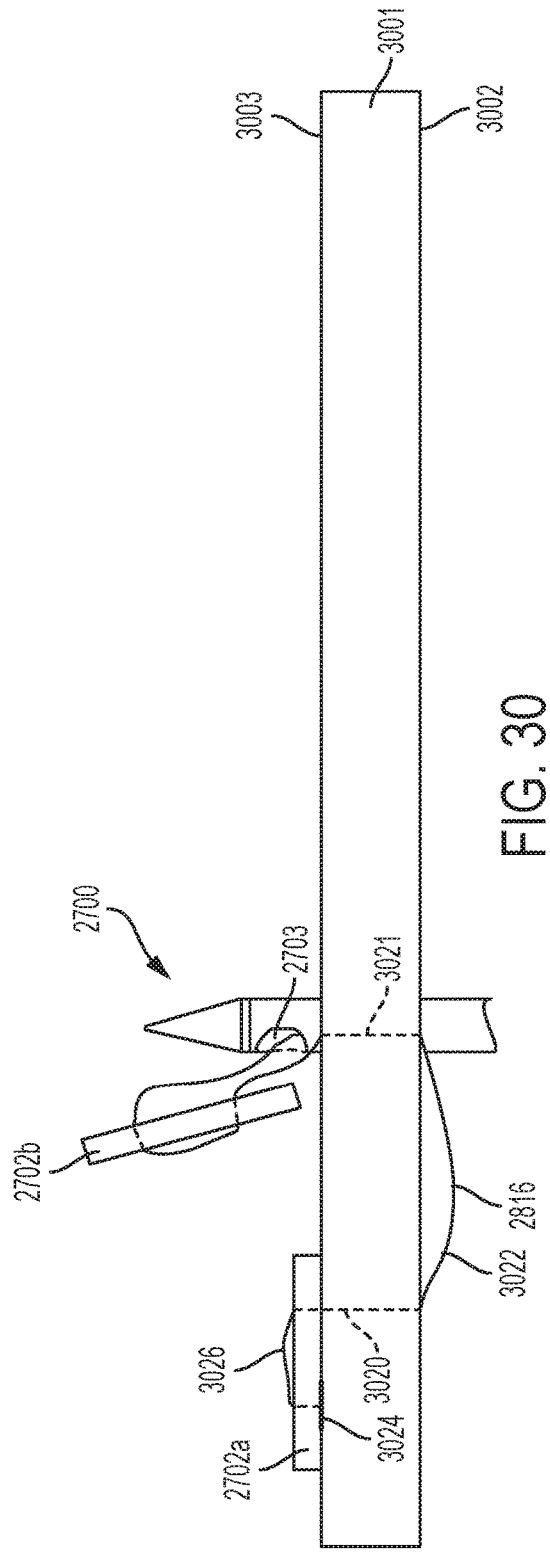
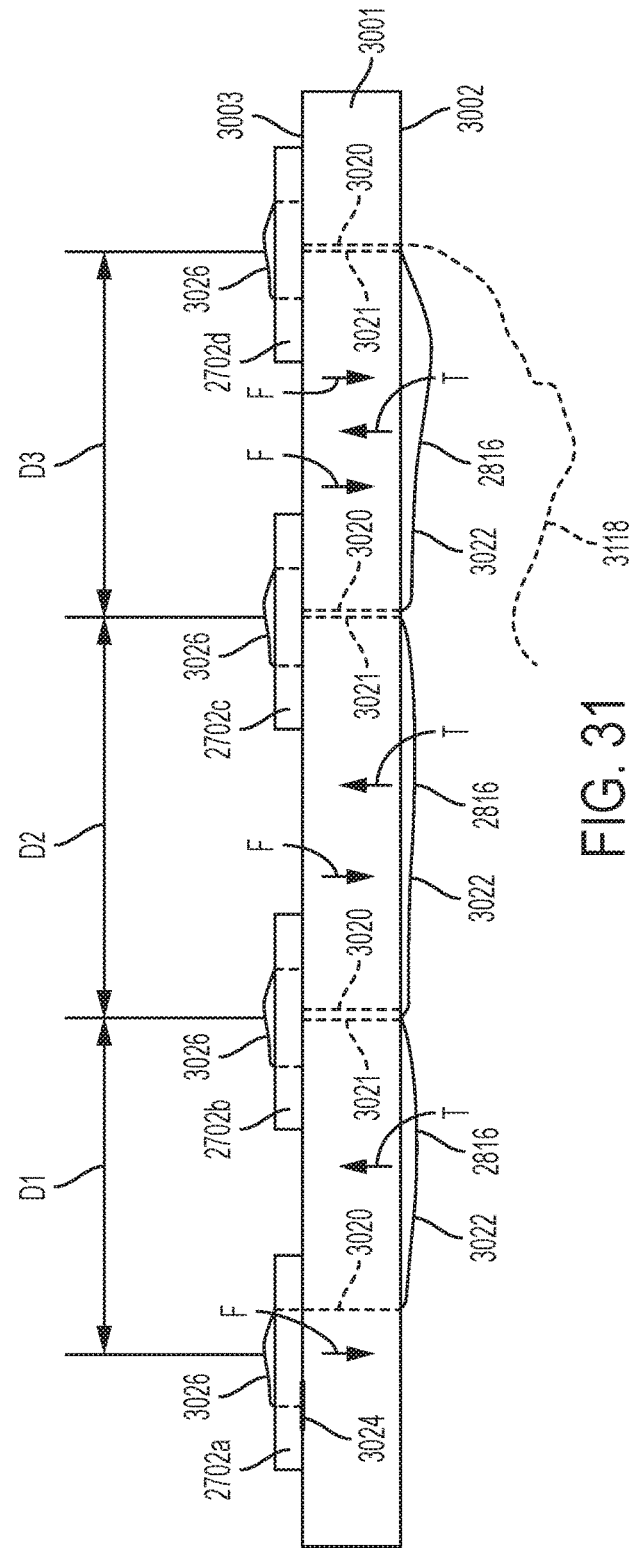
FIG. 30
FIG. 31

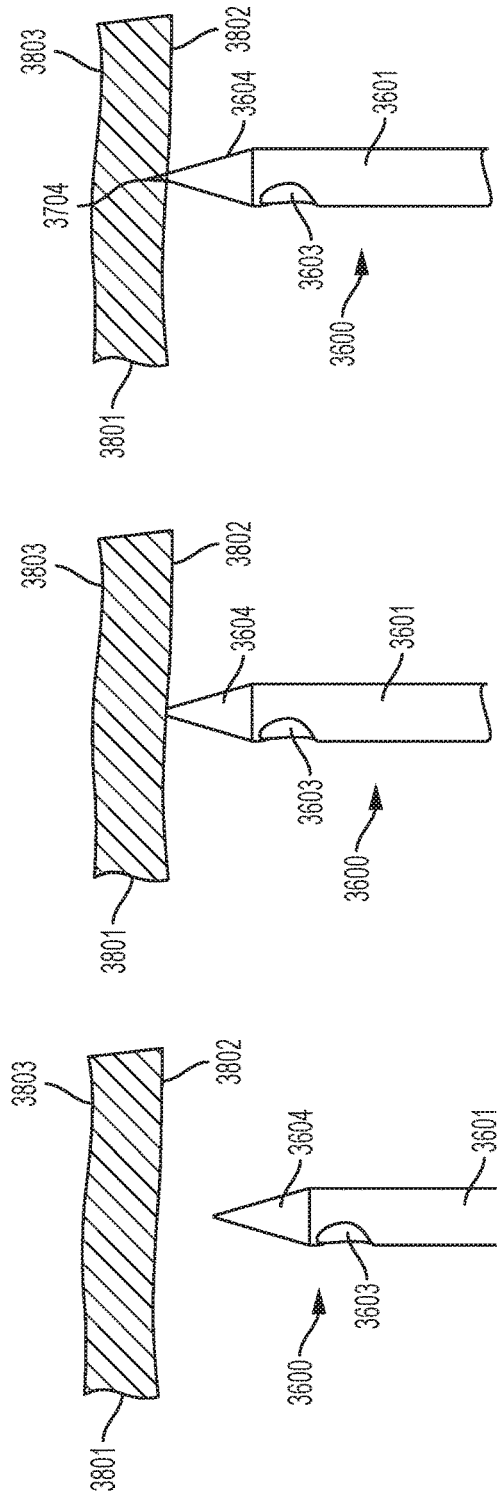

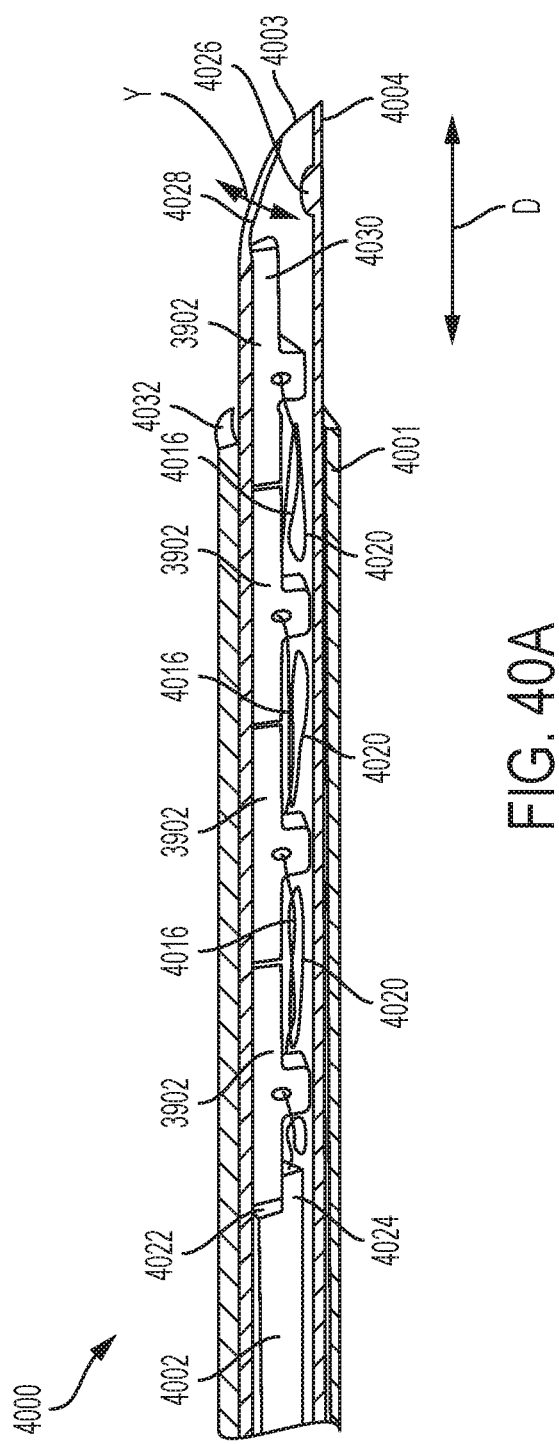
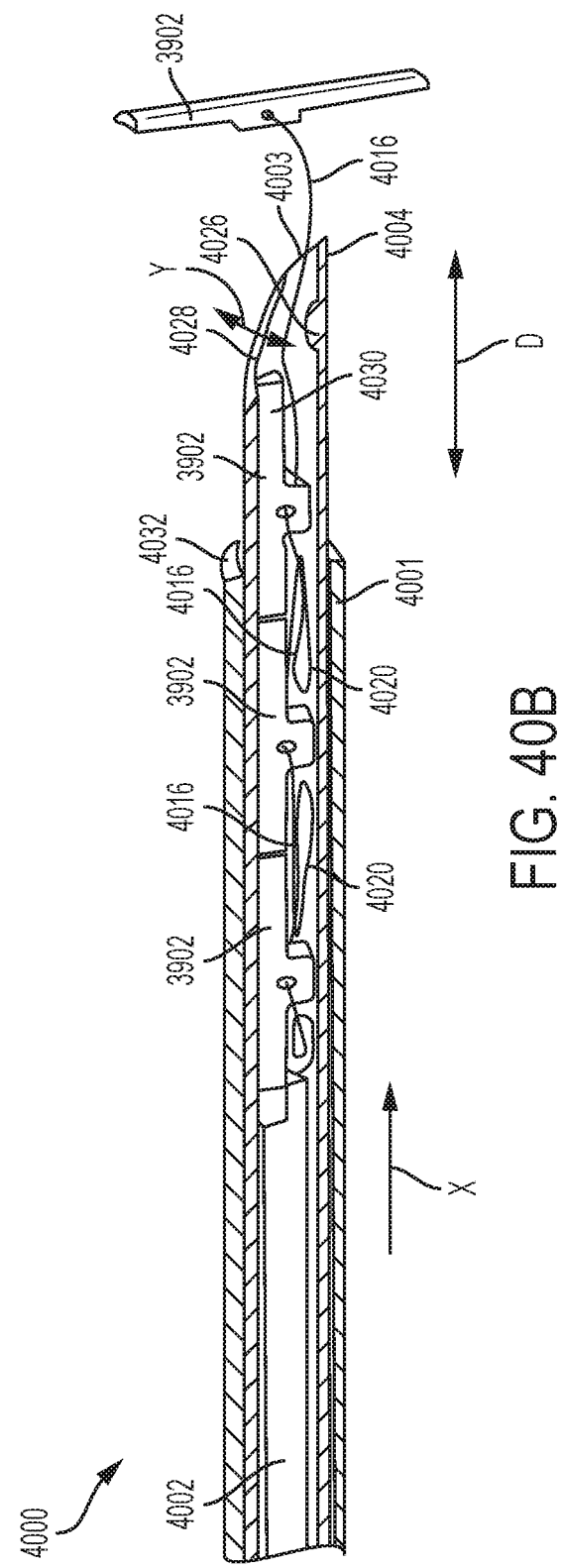
FIG. 40A
FIG. 40B

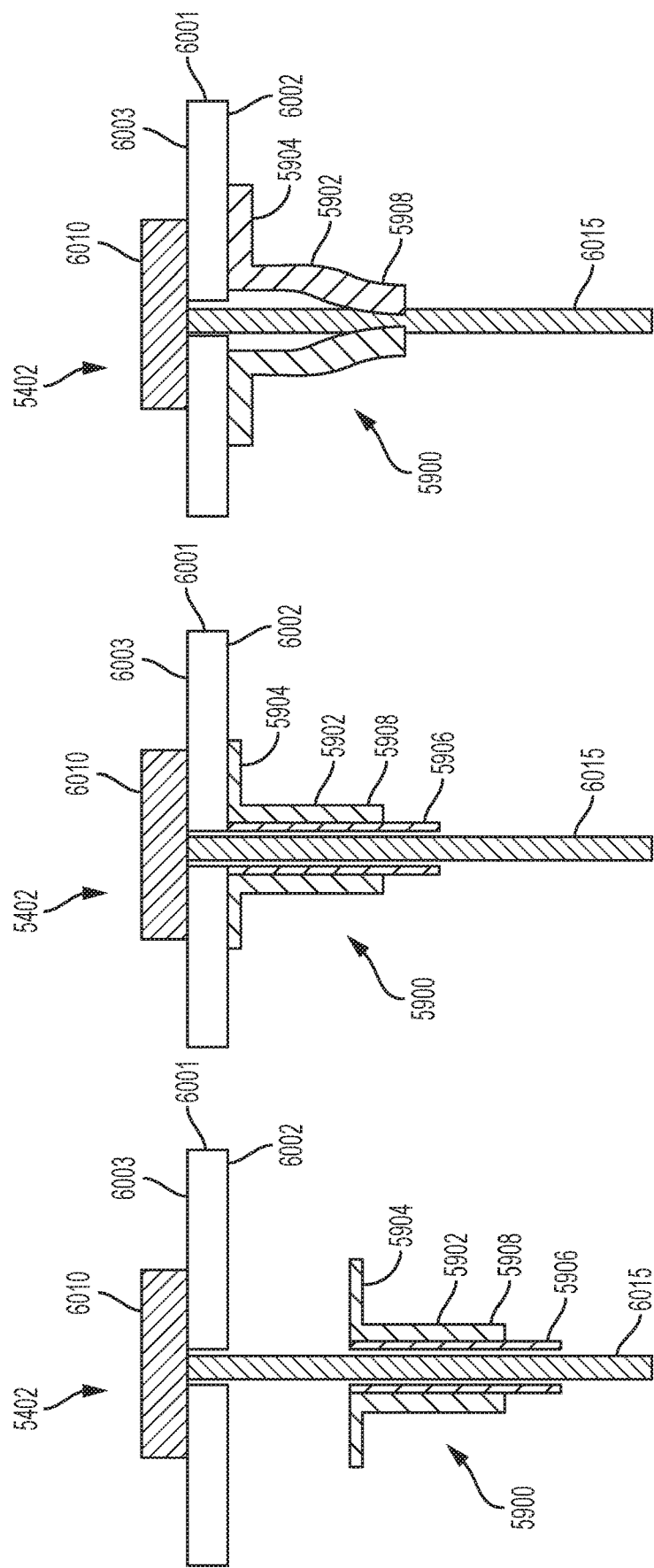

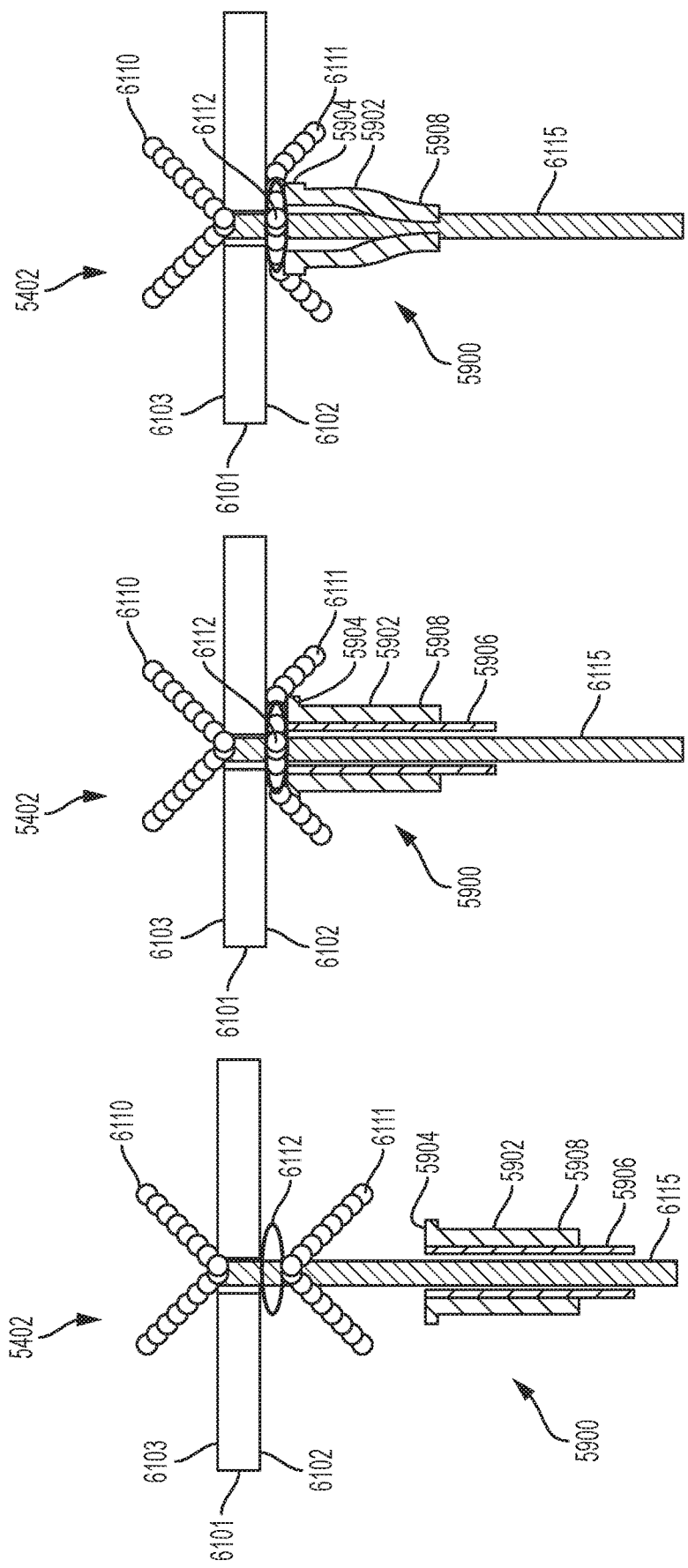

VALVE REPAIR DEVICES AND PROCEDURES

RELATED APPLICATION

This application claims the benefit of U.S. Patent Application No. 62/680,852, filed on Jun. 5, 2018, the entire disclosure of which is incorporated by reference herein.

BACKGROUND

Technical Field

The present disclosure generally relates to the field of valve repair devices and processes.

Description of Related Art

Biological valves, such as heart valves, can become defective, which can present certain health risks. Valve replacement and/or repair procedures can improve function of a defective heart valve in some cases.

SUMMARY

An exemplary method for repairing a native valve of a patient during a non-open-heart procedure includes attaching a pair of attachment members to the native valve. The pair of attachment members include a first attachment member and a second attachment member, and both the first attachment member and the second attachment member have a securing portion and a suture portion. The suture portion is attached to the securing portion. The securing portion abuts a first side of the native valve and the suture portion extends from the securing portion, through the native valve, and outward from a second side of the native valve. The exemplary method further includes applying a force to the suture portions of both the first attachment member and the second attachment member, such that the first attachment member and the second attachment member are drawn relatively toward one another to a cinched position. In addition, the exemplary method includes attaching an anchor member to the suture portions of both the first attachment member and the second attachment member such that the first and second attachment members are secured in the cinched position.

An exemplary method for repairing the mitral valve of a patient during a non-open-heart procedure includes inserting a valve repair device into a heart of the patient, in which two or more attachment members are disposed in the valve repair device. Each attachment member has a securing portion. The exemplary method also includes engaging a first side of the annulus of the mitral valve with the valve repair device and attaching the two or more attachment members to the annulus such that the securing portion of each attachment member is disposed on a second side of the annulus. In addition, the exemplary method includes applying a force to each of the two or more attachment members to cause a cinching effect on at least a portion of the annulus. The exemplary method further includes securing the two or more attachment members with one or more anchor members, such that each of the two or more attachment members maintain the cinching effect.

Another exemplary method for repairing the mitral valve of a patient during a non-open-heart procedure includes inserting a valve repair device into a heart of the patient. The valve repair device has a delivery member, an advancement member, and a puncturing member. The delivery member has an outlet. The advancement member is configured to move two or more attachment members out of the outlet of the delivery member. The attachment members are connected by a suture. The exemplary method further includes puncturing a first location of the annulus of the mitral valve with the puncturing member, such that the outlet of the delivery member moves from a first side of the annulus to a second side of the annulus. In addition, the exemplary method includes deploying a first attachment member out of the outlet of the delivery member, such that the first attachment member abuts the second side of the annulus. The exemplary method then includes moving the outlet of the delivery member from the second side of the annulus to the first side of the annulus, such that the suture extends from the first attachment member, through the annulus, and outward from the first side of the annulus. The exemplary method further includes puncturing a second location of the annulus of the mitral valve with the puncturing member of the valve repair device, such that the outlet of the delivery member moves from the first side to the second side of the annulus, and such that the suture extends through the annulus and outward from the second side of the annulus. Subsequently, the exemplary method includes deploying a second attachment member out of the outlet of the delivery member, such that the second attachment member abuts the second side of the annulus. Next, the exemplary method includes moving the outlet of the delivery member from the second side to the first side of the annulus, such that the suture extends from the second attachment member, through the annulus, and outward from the first side of the annulus. The exemplary method further includes applying a force to the suture such that the two or more attachment members cause a cinching effect on at least a portion of the annulus of the mitral valve and securing the suture with one or more anchor members to maintain the cinching effect.

An exemplary method for repairing the mitral valve of a patient during a non-open-heart procedure includes inserting a valve repair device into a heart of the patient. The valve repair device is configured to deploy an annuloplasty band, and the valve repair device is configured to attach one or more attachment members to the mitral valve and the annuloplasty band. Each attachment member has a securing portion and a suture portion. The exemplary method also includes deploying the annuloplasty band from the valve repair device such that the annuloplasty band abuts a first side of the annulus. Subsequently, the exemplary method includes attaching the one or more attachment members to the annulus and the annuloplasty band. The securing portions of the attachment members are disposed on a second side of the annulus, and the suture portions of the attachment members extend from the securing portion, through the annulus and the annuloplasty band, and extends outward from the annuloplasty band. The exemplary method further includes attaching an anchor member to the suture portion of each attachment member to secure the annuloplasty band to the annulus.

Counterparts of any of these methods are also suitable for simulating the repair of a mitral valve, for example, on a living animal, cadaver or portion thereof, or in simulation, for example, using physical and/or virtual models. Such simulations are useful, for example, in training, procedure development, research, and the like.

An exemplary embodiment of a valve repair device includes a delivery member, one or more attachment members, an advancement member, and a puncturing member. The delivery member has a shaft and an opening. The one or more attachment members are disposed in the shaft of the delivery member. The attachment members include a main body portion, a tab portion, an opening, and a suture. The main body portion of the attachment members has a tongue portion and a groove portion. The suture extends through the opening of each of the attachment members. The tongue portion of one attachment member and the groove portion of an adjacent attachment member are engaged when the one attachment member and the adjacent attachment member are disposed in the shaft of the delivery member. The advancement member is configured to move the one or more attachment members through the shaft and out of the opening of the delivery member. The puncturing member is configured to puncture a tissue member.

In some implementations, the present disclosure relates to a tissue anchor delivery device comprising a needle including a hollow shaft portion, a tip portion, and an outlet opening, a plurality of tissue anchors disposed within the shaft portion of the needle, and a suture coupled to each of the plurality of tissue anchors and disposed at least partially within the shaft portion of the needle. In some embodiments, the plurality of tissue anchors comprises a plurality of pledgets and the plurality of pledgets are configured in a compressed configuration within the shaft portion of the needle. For example, the compressed configuration can be a cylindrically-rolled configuration. The plurality of pledgets can be configured to automatically transition to an expanded configuration when deployed from the outlet opening of the needle. In some embodiments, the plurality of pledgets comprise at least one of: fabric, cotton, polymer, expandable foam, shape memory metal, and mesh.

The plurality of pledgets may comprise one or more radiopaque markers. In some embodiments, the tissue anchor delivery device further comprises a pusher device disposed at least partially within the shaft portion of the needle and configured to move the plurality of tissue anchors within the shaft portion, wherein the suture is disposed at least partially within a lumen of the pusher device. The outlet opening can an opening in a sidewall of the shaft portion of the needle. In some embodiments, the outlet opening is associated with the tip portion of the needle. The tissue anchor delivery device can further comprise a suction device configured to hold the tissue anchor delivery device to a heart valve annulus. The tissue anchor delivery device can be configured to attach the plurality of tissue anchors to the heart valve annulus.

In some embodiments, the tip portion of the needle is blunt. The tissue anchor delivery device of claim can further comprise a retractable puncturing feature configured to extend from the tip portion of the needle. For example, the retractable puncturing feature can be spring-loaded. In some embodiments, the tip portion is a separate component from the shaft portion and the tip portion is attached to an end of the shaft portion. The tip portion can be a solid tapered tip.

In some implementations, the present disclosure relates to a tissue anchor comprising an elongate body portion, a tab portion projecting from the body portion, and a suture engagement feature associated with the tab portion. The body portion can have a round cross-sectional shape. For example, the body portion can have a diameter between about 1-2 mm. In some embodiments, the body portion has a flat surface configured to engage a surface of a heart valve. For example, the flat surface can be configured to provide substantially even load distribution for the tissue anchor when engaged with a surface of biological tissue. In some embodiments, the body portion has of length of between about 4-10 mm.

The suture engagement feature can be or comprise an aperture in the tab portion dimensioned to allow for threading of a suture therethrough. In some embodiments, the tissue anchor further comprises a suture engaged with the suture engagement feature. In some embodiments, the tissue anchor further comprises a tongue feature associated with a first end of the body portion and a groove feature associated with a second end of the body portion. The tab portion and the body portion can define a first recess on a first side of the tab portion and a second recess on a second side of the tab portion. For example, the first recess can be configured to provide space for a suture when the anchor device is disposed within a lumen adjacent to another tissue anchor.

In some implementations, the present disclosure relates to a suture fixation device comprising a longitudinal compression shaft, and a radial abutment flange associated with a distal end of the compression shaft, wherein the compression shaft is configured to compress and apply inward radial force on a portion of a suture disposed within a lumen of the compression shaft. The suture fixation device can further comprise a placement shaft configured to be disposed within the lumen of the compression shaft. In some embodiments, the placement shaft forms an internal lumen configured to have the portion of the suture slidingly disposed at least partially therein and the placement shaft is configured to prevent the compression shaft from compressing on the portion of the suture when the placement shaft is disposed within the lumen of the compression shaft. In some embodiments, removal of the placement shaft from the lumen of the compression shaft causes the compression shaft to compress and fix the portion of the suture relative to compression shaft.

A further understanding of the nature and advantages disclosed herein are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments of the present disclosure will be described and explained with additional specificity and detail through the use of the accompanying drawings.

FIGS. 7A, 7C and 7E illustrate the mitral valve shown from the direction represented by line A-A FIG. 6 during an exemplary process for repairing a first portion of the mitral valve using the exemplary valve repair device of FIG. 5.

FIGS. 7B, 7D and 7F illustrate the mitral valve shown from the direction represented by line B-B FIG. 6 during an exemplary process for repairing a first portion of the mitral valve using the exemplary valve repair device of FIG. 5.

FIGS. 10A, 10C and 10E illustrate the mitral valve shown from the direction represented by line A-A FIG. 9 during an exemplary process for repairing a first portion of the mitral valve using the exemplary valve repair device of FIGS. 8 and 9.

FIGS. 10B, 10D and 10F illustrate the mitral valve shown from the direction represented by line B-B FIG. 9 during an exemplary process for repairing a first portion of the mitral valve using the exemplary valve repair device of FIGS. 8 and 9.

FIGS. 19A, 19C and 19E illustrate the mitral valve shown from the direction represented by line A-A FIG. 16 during an exemplary process for repairing a first portion of the mitral valve using the exemplary valve repair device of FIG. 18.

FIGS. 19B, 19D and 19F illustrate the mitral valve shown from the direction represented by line B-B FIG. 16 during an exemplary process for repairing a first portion of the mitral valve using the exemplary valve repair device of FIG. 18.

FIG. 30 illustrates the exemplary embodiment of the valve repair device of FIG. 27 engaging a tissue member to attach an exemplary embodiment of a pledget to the tissue member.

FIG. 31 illustrates the tissue member of FIG. 31 after multiple pledgets have been attached to the tissue member by the exemplary valve repair device of FIG. 27.

FIGS. 38A-38F illustrate the exemplary valve repair device shown in FIGS. 37A-37B engaging a tissue member and attaching a pledget to the tissue member.

FIGS. 40A-40B illustrate another exemplary embodiment of a valve repair device.

FIG. 60A-60C illustrates an exemplary procedure for securing an exemplary embodiment of an attachment member to a tissue member with the exemplary anchor member of FIGS. 59A-59C.

FIG. 61A-61C illustrates an exemplary procedure for securing an exemplary embodiment of an attachment member to a tissue member with the exemplary anchor member of FIGS. 59A-59C.

DETAILED DESCRIPTION

Figure 1:
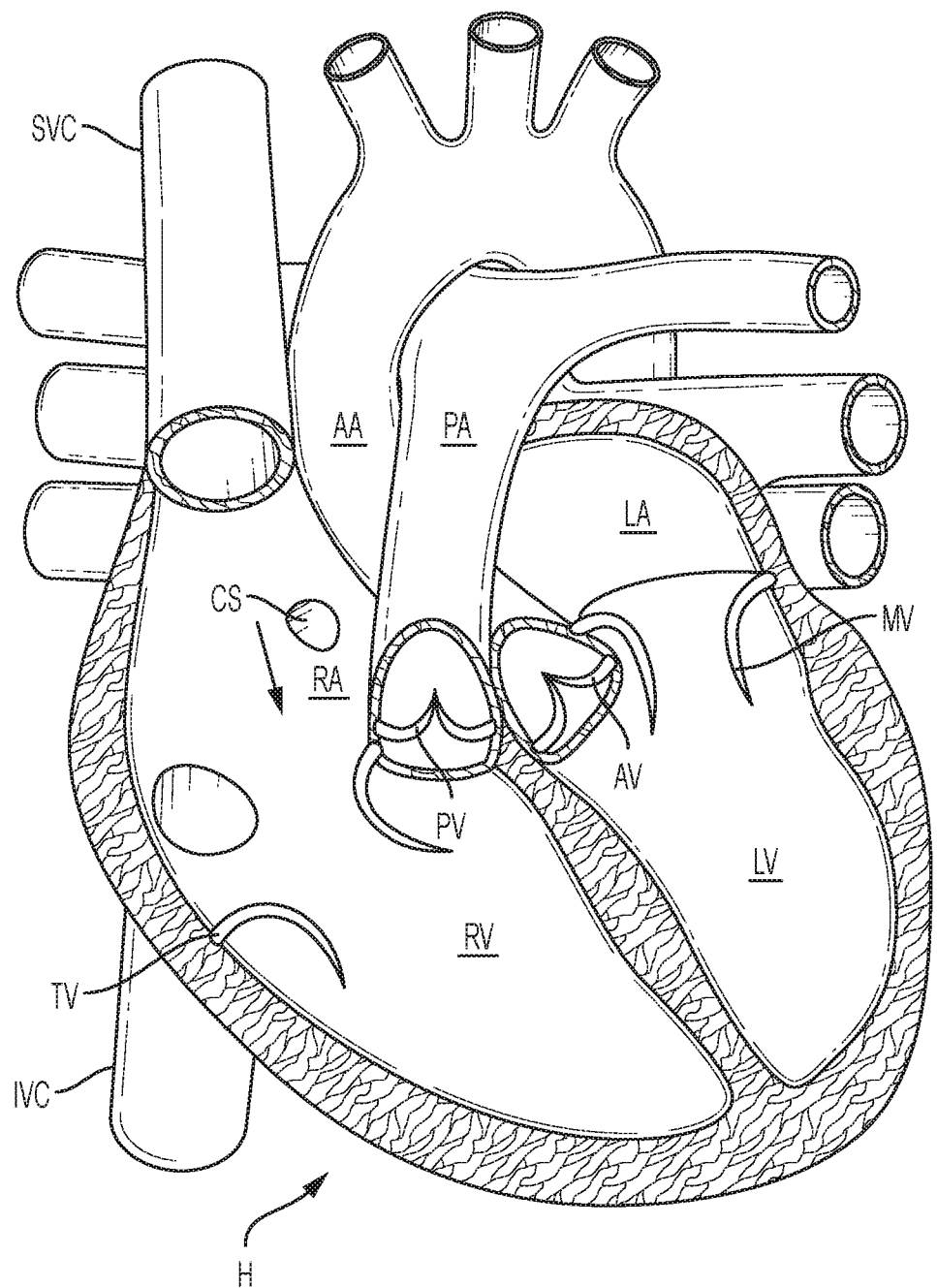
FIG. 1 is a cutaway view of the human heart in a diastolic phase.

The following description refers to the accompanying drawings, which illustrate specific embodiments. Other embodiments having different structures and operation do not depart from the scope of the disclosure.

Embodiments of the present disclosure relate to devices and methods for improving the function of a defective heart valve. Certain embodiments disclosed herein may be particularly well suited or adapted for reparations of a patient's native heart valve.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The function of the heart can be seriously impaired if any of the heart valves are not functioning properly. The heart valves may lose their ability to close properly due to, for example, annular dilation, ventricular dilation, or a failed native cord causing a prolapsing leaflet, with annular dilation being the most common. The leaflets may also have shrunk due to disease (e.g. rheumatic disease), and thereby leave a gap in the valve between the leaflets. The inability of the heart valve to close properly can cause a leak backwards (e.g., from the outflow to the inflow side), commonly referred to as regurgitation, through the valve. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmias or death.

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

Exemplary embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

Figure 2:
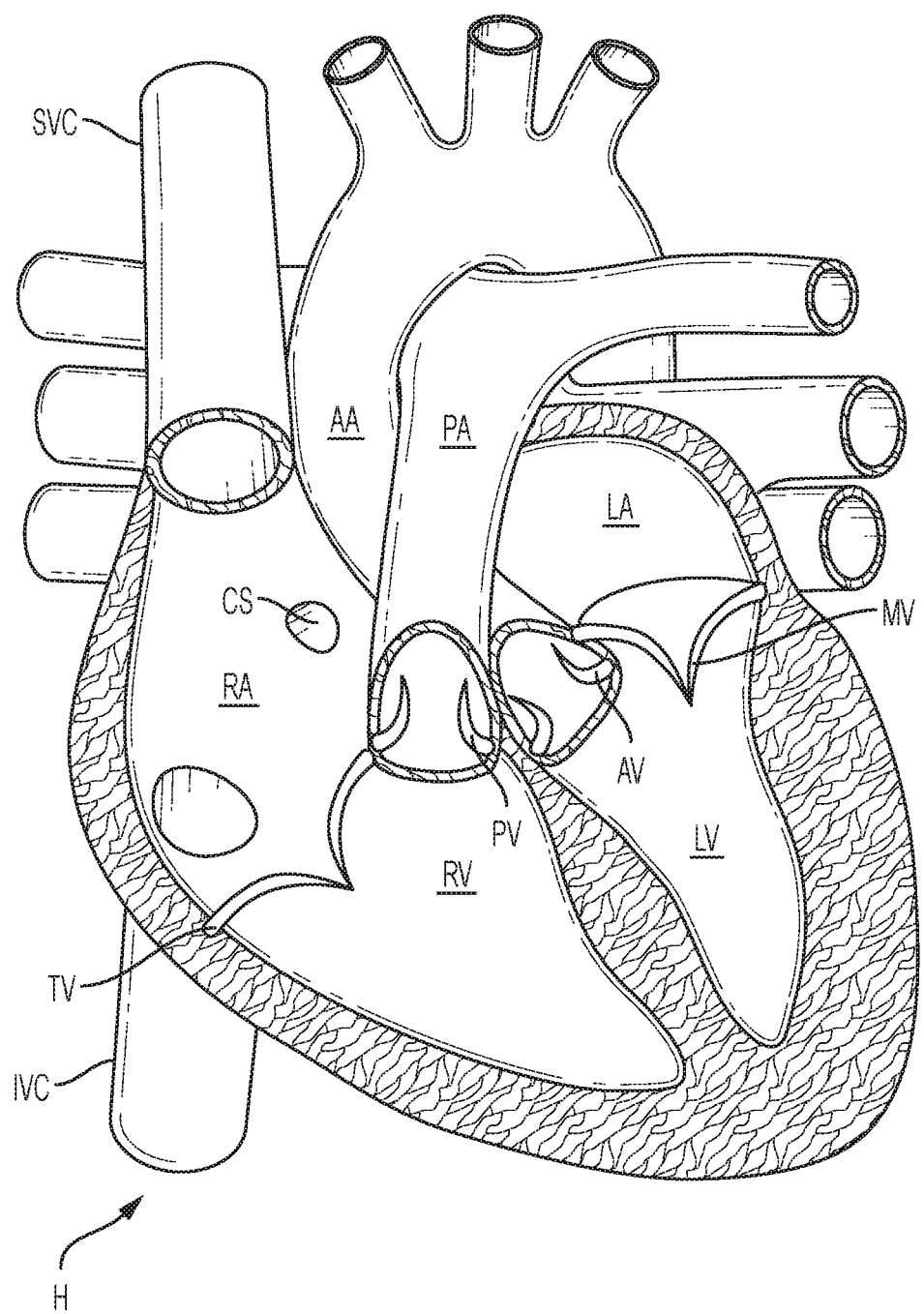
FIG. 2 is a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV (e.g., the atrioventricular valves). Additionally, the aortic valve AV separates the left ventricle LV from the ascending aorta AA, and the pulmonary valve PV separates the right ventricle from the pulmonary artery PA. Each of these valves has flexible leaflets (e.g., leaflets 302, 304 shown in FIGS. 3 and 4) extending inward across the respective orifices that come together or "coapt" in the flowstream to form the one-way, fluid-occluding surfaces. The native valve repair devices of the present application are described primarily with respect to the mitral valve MV. Therefore, anatomical structures of the left atrium LA and Left ventricle LV will be explained in greater detail. It should be understood that the devices described herein may also be used in repairing other native valves. For example, the devices can be used in repairing either of the atrioventricular valves, such as the tricuspid valve TV, in addition to the mitral valve MV. In addition, in some embodiments the devices described herein can be used to repair the aortic valve AV, and/or the pulmonary valve PV.

The left atrium LA receives oxygenated blood from the lungs. During the diastolic phase, or diastole, seen in FIG. 1, the blood that collects in the left atrium LA enters the mitral valve MV by expansion of the left ventricle LV. In the systolic phase, or systole, seen in FIG. 2, the left ventricle LV contracts to force the blood through the aortic valve AV and PA into the body. In one exemplary embodiment, the devices described by the present application are used to repair the function of a defective mitral valve MV. During systole, the leaflets of the mitral valve MV close to prevent the blood from regurgitating back into the left atrium LA.

Referring to FIGS. 1-4, the mitral valve MV includes two leaflets, the anterior leaflet 302 and the posterior leaflet 304. The mitral valve MV also includes an annulus 306, which is a variably dense fibrous ring of tissues that encircles the leaflets 302, 304. The mitral valve MV is anchored to the wall of the left ventricle LV (FIGS. 1 and 2) by chordae tendineae (not shown), which are cord-like tendons that connect the papillary muscles (e.g., the muscles located at the base of the chordae tendineae and within the walls of the left ventricle) to the leaflets 302, 304. Without the connection to the chordae tendineae and the papillary muscles, the mitral valve leaflets would revert or prolapse back toward and/or into the atrium, which is known as leaflet "flail." The papillary muscles serve to limit the movements of the mitral valve MV leaflets and prevent the mitral valve leaflets from flailing. The mitral valve opens and closes in response to pressure changes in the left atrium LA and the left ventricle LV. The papillary muscles brace the mitral valve MV against the high pressure needed to circulate blood throughout the body. Together the papillary muscles and the chordae tendineae are known as the subvalvular apparatus, which functions to keep the mitral valve MV leaflets from flailing into the left atrium LA when the mitral valve closes.

Various disease processes can impair proper function of one or more of the valves of the native valves of the heart H. These disease processes include degenerative processes (e.g., Barlow's Disease, fibroelastic deficiency), inflammatory processes (e.g., rheumatic heart disease), and infectious processes (e.g., endocarditis). In addition, damage to the left ventricle LV or the right ventricle RV from prior heart attacks (e.g., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 302, 304) of a native valve (e.g., the mitral valve MV), which results in prolapse and regurgitation.

Generally, a native valve may malfunction in two different ways. One possible malfunction is valve stenosis, which occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

Another possible malfunction is valve regurgitation, which occurs when the leaflets of the valve do not close completely thereby causing blood to leak back into the prior chamber (e.g., causing blood to leak from the left ventricle to the left atrium). There are three mechanisms by which a native valve becomes regurgitant or incompetent, which include Carpentier's type I, type II, and type III malfunctions. A Carpentier type 1 malfunction involves the dilation of the annulus such that normally functioning leaflets are distracted from each other and fail to form a tight seal (e.g., do not coapt properly). Included in a type I mechanism malfunction are perforations of the leaflets, as in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (111a) or dilation of a ventricle (111b).

Figure 3:
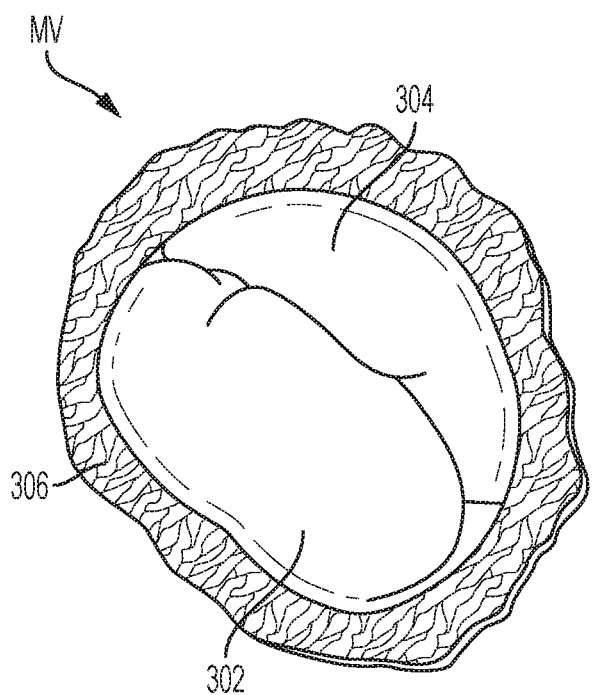
FIG. 3 is a perspective view of a healthy mitral valve with the leaflets closed (See also FIG. 67A).
Figure 4:
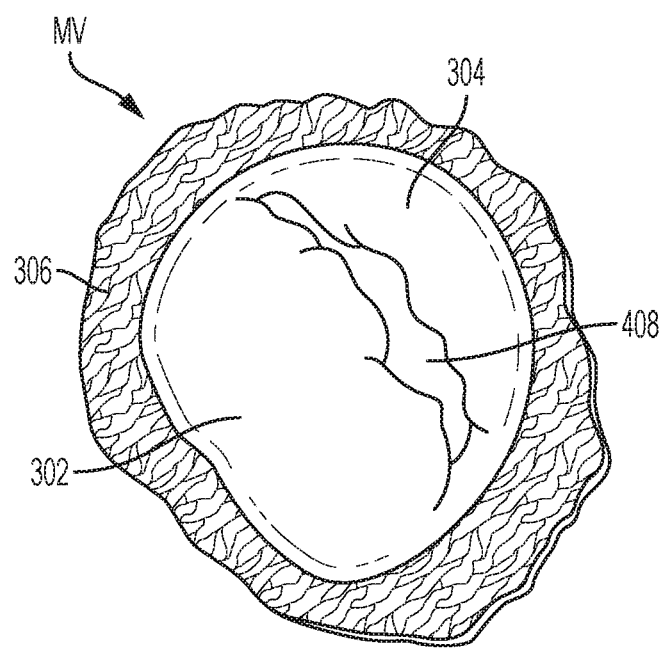
FIG. 4 is perspective view of a dysfunctional mitral valve with a visible gap between the leaflets.

Referring to FIG. 3, when a healthy mitral valve MV is in a closed position, the anterior leaflet 302 and the posterior leaflet 304 coapt, which prevents blood from leaking from the left ventricle LV to the left atrium LA. Referring to FIG. 4, regurgitation occurs when the anterior leaflet 302 and/or the posterior leaflet 304 of the mitral valve MV is displaced into the left atrium LA during systole. This failure to coapt causes a gap 408 between the anterior leaflet 302 and the posterior leaflet 304, which allows blood to flow back into the left atrium LA from the left ventricle LV during systole. As set forth above, there are several different ways that a leaflet (e.g. leaflets 302, 304 of mitral valve MV) may malfunction, which can thereby lead to regurgitation.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (e.g., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatment for a stenotic aortic valve or stenotic pulmonary valve is removal and replacement. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable.

Exemplary embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible. The devices and procedures disclosed herein make reference to correcting the dilation of the annulus for a mitral valve. However, it should be understood that the devices and concepts provided herein can be used to repair any native valve, as well as any component of a native valve.

Referring to FIGS. 5 through 10A-10F, an exemplary procedure for mitral annuloplasty is shown using an exemplary embodiment of a valve repair device 500. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 708 in FIGS. 7A-7F), which could lead to regurgitation of blood through the mitral valve. The exemplary mitral annuloplasty procedure provides annular support to the mitral valve by reducing the size of the annulus, which allows the leaflets to properly coapt.

Figure 5:
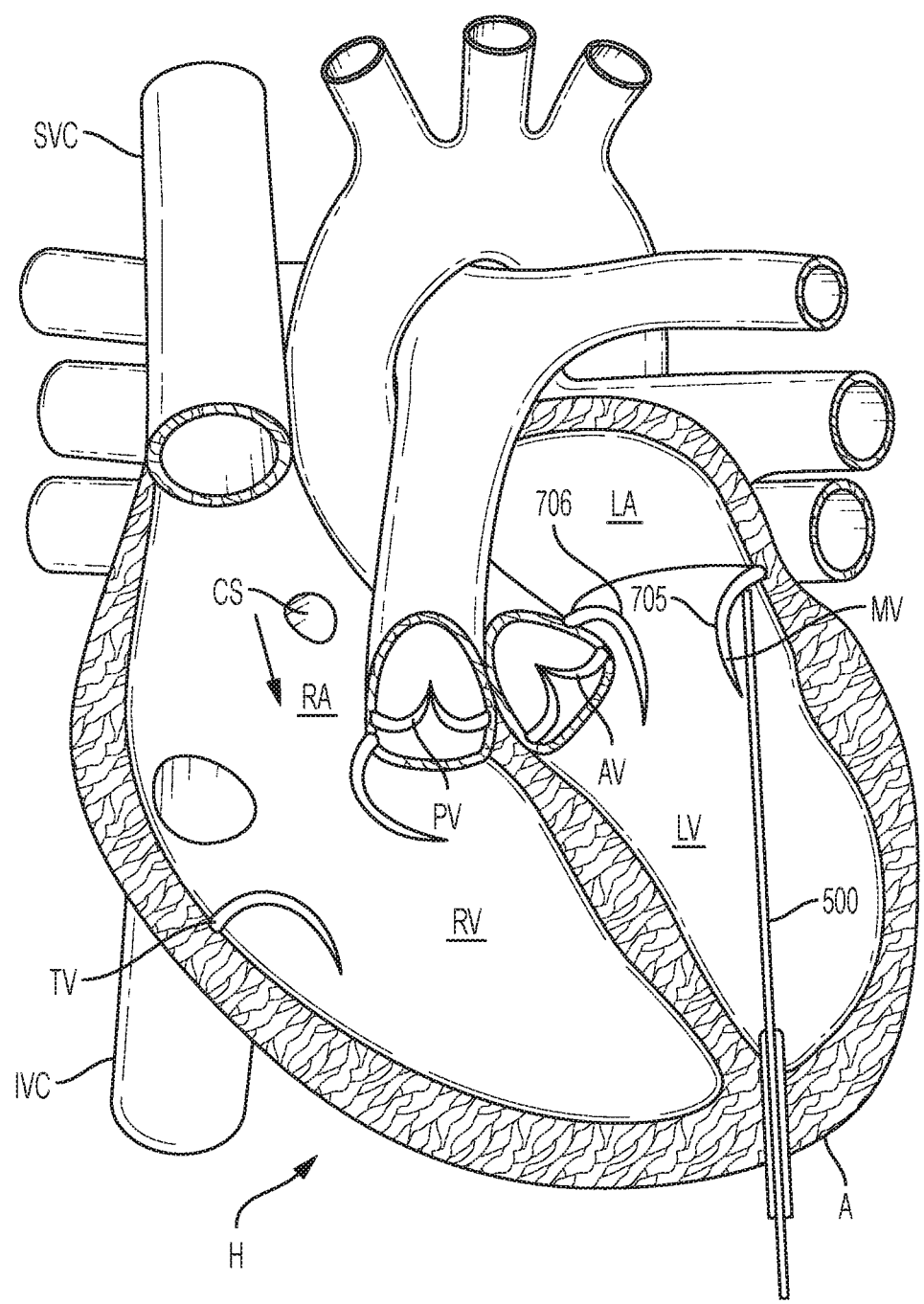
FIG. 5 is a cutaway view of the human heart showing an exemplary embodiment of a valve repair device engaging a first location of the annulus of the mitral valve through the apex of the heart.
Figure 6:
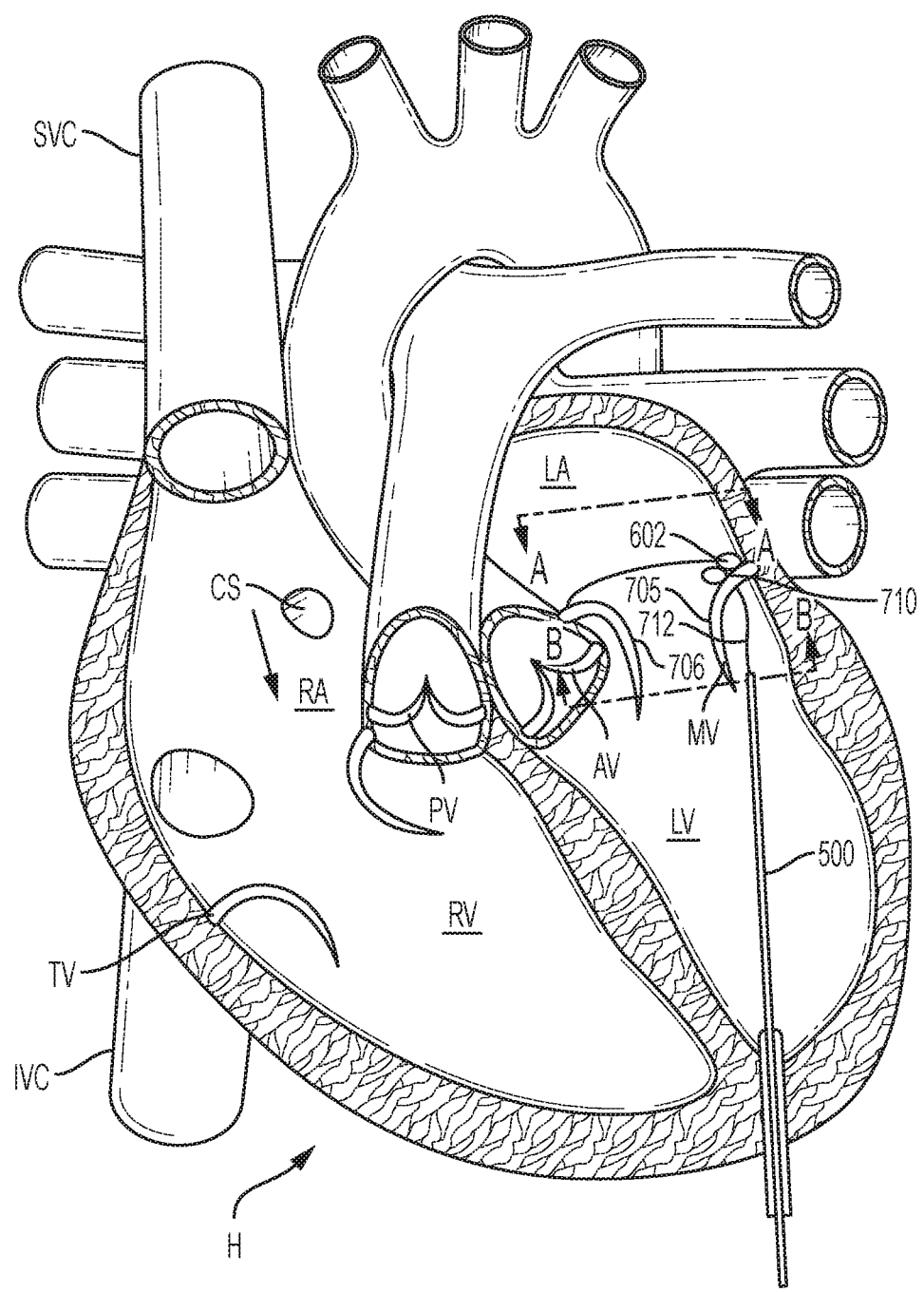
FIG. 6 illustrates the exemplary valve repair device engaging the first location of the annulus of the mitral valve, as shown in FIG. 5, after the valve repair device attaches an attachment member to the first location of the annulus.

Referring to FIG. 5, the valve repair device 500 enters the left ventricle LV through the apex A of the heart H. After the valve repair device 500 enters the left ventricle LV, the repair device engages the mitral valve MV. Referring to FIG. 6, the valve repair device 500 is configured to attach an attachment member 602 to the mitral valve MV. The valve repair device 500 may take any suitable form that is capable of entering the left ventricle LV through the apex A of the heart H and attaching an attachment member 602 to the mitral valve. For example, the valve repair device 500 can take the form of the devices described in U.S. Pat. No. 7,635,386 and U.S. Patent Application Publication No. 2014/0114404 A1, which are hereby incorporated by reference in their entireties. The attachment member 602 includes a securing portion 710 (FIGS. 7A-7F) and a suture portion 712 (FIGS. 7A-7F). In the illustrated embodiment, the securing portion 710 of the attachment member 602 is a knot. The securing portion 710 is configured to prevent the attachment member 602 from being removed from the annulus 700 when a force is applied to the suture portion 712. In alternative embodiments, the attachment member 602 may take any suitable form that is capable of providing annular support to the mitral valve, such as, for example, any form described in the present application.

The exemplary mitral annuloplasty procedure includes attaching a pair of attachment members to one or more locations (e.g., location 504 in FIGS. 5 through 7A-7F and location 814 in FIGS. 8 through 10A-10F) of the annulus 700 (FIGS. 7A-7F and FIGS. 10A-10F). In addition, the exemplary procedure includes tensioning the attachment members and anchoring the attachment members of the pair of attachment members together with an anchor member to repair at least a portion of the mitral valve MV. FIGS. 5 through 7A-7F show the valve repair device 500 attaching attachment members 602, 703 to a first location 504 of the annulus 700 to repair a first portion 702 of the mitral valve MV. FIGS. 7A, 7C, and 7E illustrate the mitral valve MV from the perspective of line A-A shown in FIG. 6 (e.g., illustrating the mitral valve MV from the left atrium LA), and FIGS. 7B, 7D, and 7F illustrate the mitral valve MV from the perspective of line B-B shown in FIG. 6 (e.g., illustrating the mitral valve MV from the left ventricle).

In a first step of the exemplary mitral annuloplasty procedure (as shown by FIGS. 7A and 7B), the valve repair device 500 attaches a first attachment member 602 of a pair of attachment members to the first location 504 of the annulus 700. Referring to FIG. 7A, the first attachment member 602 includes a securing portion 710 that extends into the left atrium LA. Referring to FIG. 7B, the first attachment member 602 includes a suture portion 712 that extends into the left ventricle LV. In a second step of the exemplary mitral annuloplasty procedure (as shown by FIGS. 7C and 7D), the valve repair device 500 attaches a second attachment member 703 of the pair of attachment members to the first location 504 of the annulus 700. Referring to FIG. 7C, the attachment member 703 includes a securing portion 716 that extends into the left atrium LA. Referring to FIG. 7D, the attachment member 703 includes a suture portion 718 that extends into the left ventricle LV. In a third step of the exemplary mitral annuloplasty procedure (as shown by FIGS. 7E and 7F), the suture portion 712 of the first attachment member 602 and the suture portion 718 of the second attachment member 703 are tensioned to create a cinching effect on the annulus 700. That is, the attachment member 602 is tensioned in a direction X and the attachment member 703 is tensioned in a direction Y. The tensioning of the attachment members 602, 703 causes the anterior leaflet 705 and the posterior leaflet 706 on the first portion 702 mitral valve MV to coapt. Once the anterior leaflet 705 and the posterior leaflet 706 properly coapt, an anchor 720 (FIG. 7F) secures the attachment members 602, 703 together to remove the gap 708 on the first portion of the mitral valve MV. The second attachment member 703 of the pair of attachment members can be placed any suitable or desirable distance from the first attachment member 602. The attachment members 602, 703 can be placed any distance apart from each other that allows the attachment members to be tensioned and secured together in order to repair at least a portion of the mitral valve MV.

The removal of the gap 708 on the first portion 702 of the mitral valve MV prevents regurgitation of blood from the left ventricle LV to the left atrium LA through the first portion 702 of the mitral valve MV. The attachment members 602, 703 can be tensioned, and the anchor 720 can be deployed, by the valve repair device 500 or a separate anchoring device (not shown). If a separate anchoring device is used, the anchoring device enters the left ventricle LV through the apex A of the heart H to engage the suture portions 712, 718 of the attachment members 602, 703. The anchor 720 may take any suitable form that is capable of securing the first attachment member 602 to the second attachment member 703 to close the gap 708 on at least a portion of the mitral valve MV. For example, the anchor 720 can be a clip that clamps onto the suture portions 712, 718, a knot tying the two suture portions 712, 718 together, any of the anchors described in this application, any other device capable of securing two sutures together, or the like, including one or more clasps, locks, fasteners, or similar device(s).

The term "suture" is used herein according to its broad and ordinary meaning and may refer to any elongate strip, strand, line, tie, string, ribbon, strap, or other type of material used in medical procedures. One having ordinary skill in the art will understand that a wire or other similar material may be used in place of a suture, and description herein of sutures or the like is applicable to wires or other similar materials.

In the illustrated embodiment, the first portion 702 of the mitral valve MV is closed by the attachment members 602, 703 attached at the first location 504 of the mitral valve MV. However, in this example, the attachment members 602, 703 did not completely close the gap 708 between the anterior leaflet 705 and the posterior leaflet 706. That is, referring to FIGS. 7E and 7F, the gap 708 remains between the anterior leaflet 705 and the posterior leaflet 706 at a second portion 814 of the mitral valve MV.

Referring to FIGS. 8 through 10A-10F, the exemplary procedure for mitral annuloplasty further includes attaching another pair of attachment members to the annulus 700 at a second location 814 to close the remaining gap 708 (e.g., the gap 708 shown in FIGS. 7E-7F and FIGS. 10A-10D) between the anterior leaflet 705 and the posterior leaflet 706. The second pair of attachment members can be attached to the annulus 700 by using the same valve repair device 500 that was used to attach the first pair of attachment members 602, 703, or the second pair of attachment members can be attached to annulus by a separate valve repair device (not shown). In the illustrated embodiment, the second pair of attachment members are attached to the annulus using the same valve repair device 500 that was used to attach the first pair of attachment members 602, 703 to the annulus. In situations where multiple pairs of attachment members are attached to the annulus 700 of the mitral valve MV, it is advantageous to attach the multiple pairs of attachment members to the annulus by the same device because attaching the pairs of attachment members using the same device will allow for less insertions of devices through the apex A of the heart H.

Figure 8:
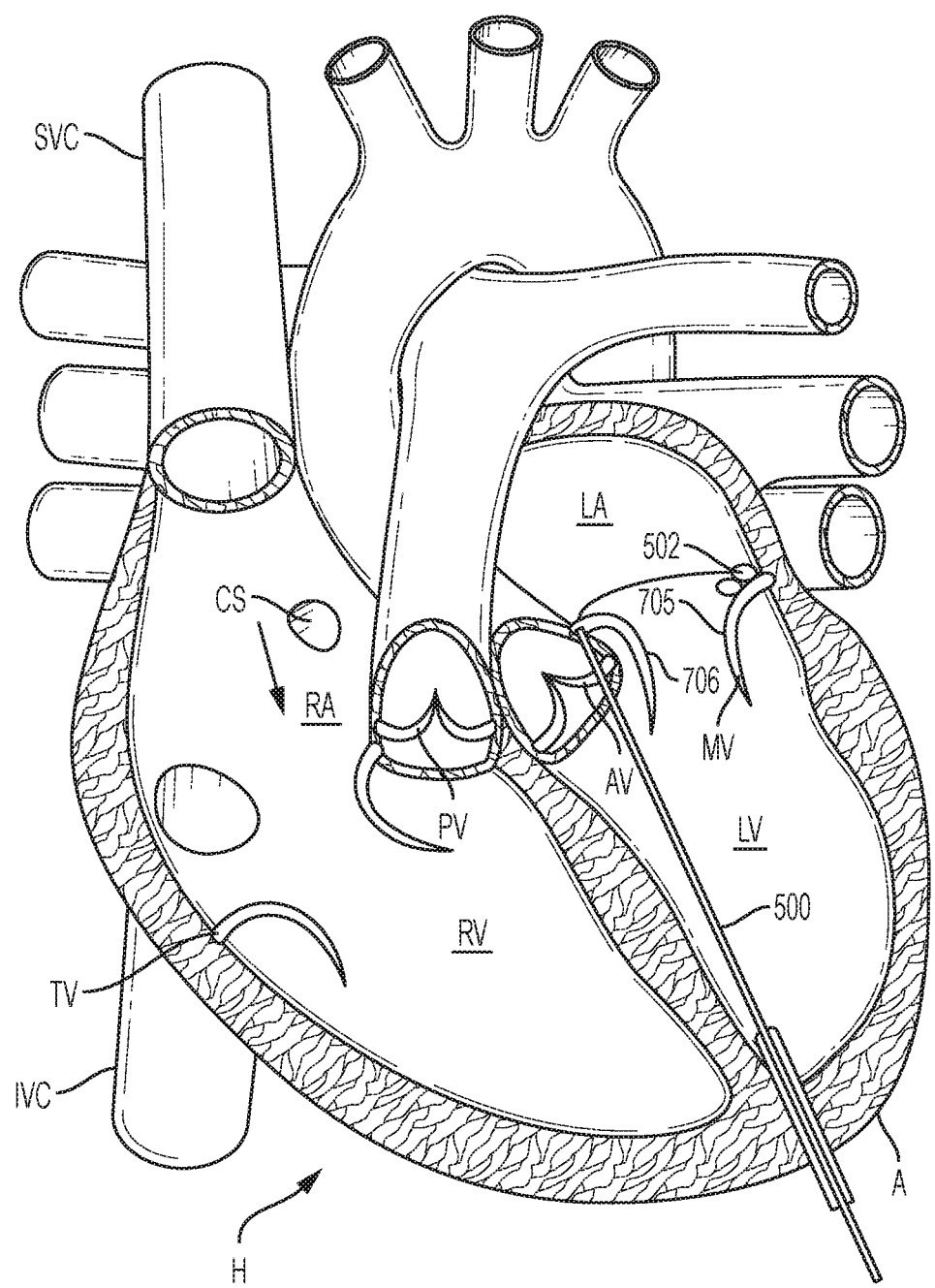
FIG. 8 is a cutaway view of the human heart showing an exemplary embodiment of a valve repair device engaging a second location of the annulus of the mitral valve through the apex of the heart.
Figure 9:
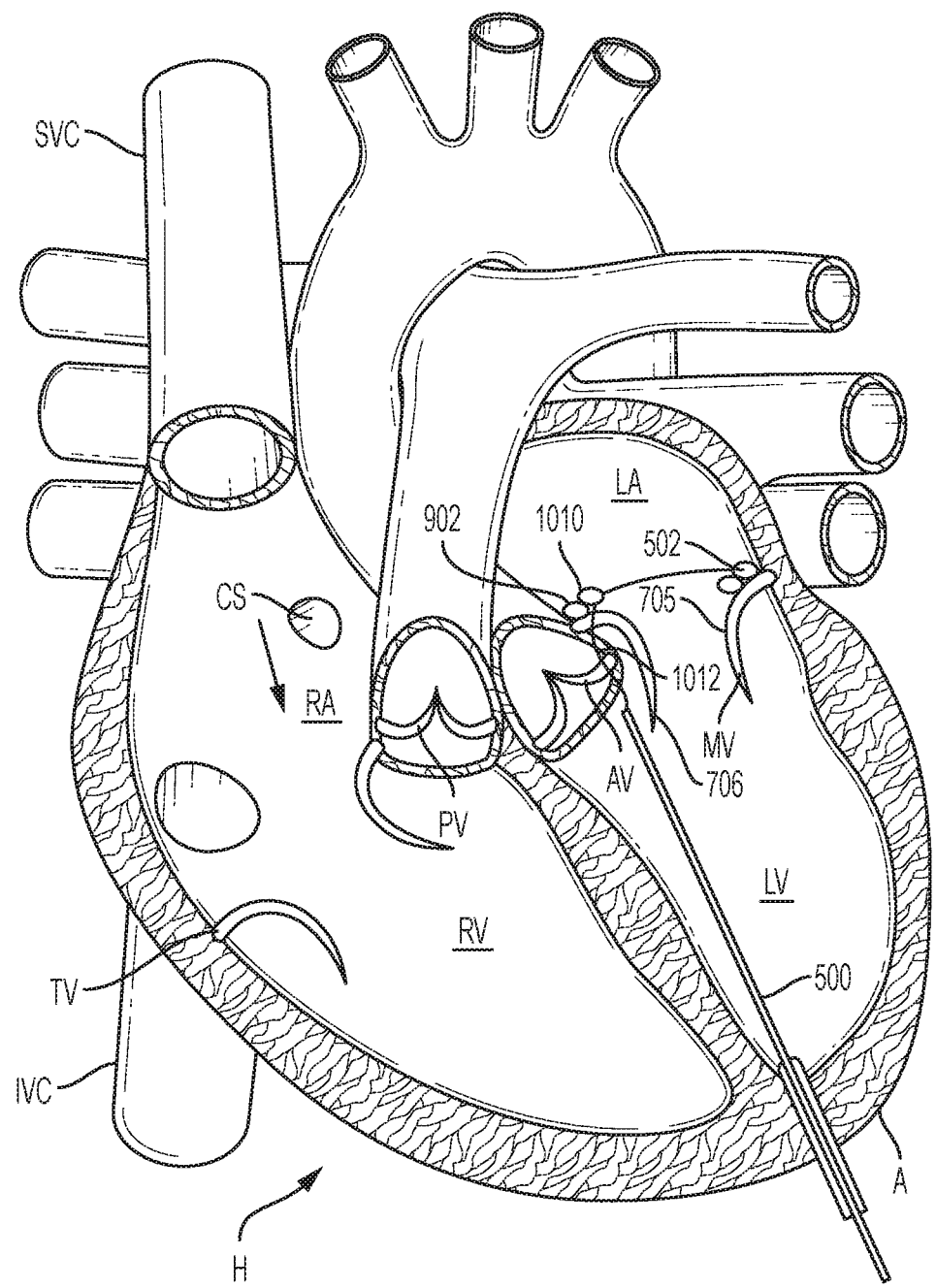
FIG. 9 illustrates the exemplary valve repair device engaging the second location of the annulus of the mitral valve, as shown in FIG. 8, after the valve repair device attaches an attachment member to the second location of the annulus.

Referring to FIG. 8, the valve repair device 500 enters the left ventricle LV through the apex A of the heart H. After the valve repair device 500 enters the left ventricle LV, the repair device engages the mitral valve MV. Referring to FIG. 9, the valve repair device 500 is configured to attach an attachment member 902 to the mitral valve MV. The attachment member 902 includes a securing portion 1010 (FIGS. 10A-10F) and a suture portion 1012 (FIGS. 10A-10F). In the illustrated embodiment, the securing portion 1010 of the attachment member 602 is a knot. The securing portion 1010 is configured to prevent the attachment member 902 from being removed from the annulus 700 when a force is applied to the suture portion 1012. In alternative embodiments, the attachment member 902 may take any suitable form that is capable of providing annular support to the mitral valve, such as, for example, any form described in the present application.

As described above, the exemplary mitral annuloplasty procedure includes attaching a pair of attachment members to one or more locations (e.g., location 504 in FIGS. 5 through 7A-7F and location 814 in FIGS. 8 through 10A-10F) of the annulus 700 (FIGS. 7A-7F and FIGS. 10A-10F). In addition, the exemplary procedure includes tensioning the attachment members and anchoring the attachment members of a pair of attachment members together with an anchor member to repair at least a portion of the mitral valve MV. FIGS. 8 through 10A-10F show the valve repair device 500 attaching attachment members 902, 1003 to a second location 814 of the annulus 700 to repair a second portion 722 of the mitral valve MV. FIGS. 10A, 10C, and 10E illustrate the mitral valve MV from the perspective of line A-A shown in FIG. 9 (e.g., illustrating the mitral valve MV from the left atrium LA), and FIGS. 10B, 10D, and 10F illustrate the mitral valve MV from the perspective of line B-B shown in FIG. 9 (e.g., illustrating the mitral valve MV from the left ventricle).

In a fourth step of the illustrated exemplary mitral annuloplasty procedure (as shown by FIGS. 10A and 10B), the valve repair device 500 attaches a first attachment member 902 of a pair of attachment members to the second location 814 of the annulus 700. Referring to FIG. 10A, the first attachment member 902 includes a securing portion 1010 that extends into the left atrium LA. Referring to FIG. 10B, the first attachment member 902 includes a suture portion 1012 that extends into the left ventricle LV. In a fifth step of the exemplary mitral annuloplasty procedure (as shown by FIGS. 10C and 10D), the valve repair device 500 attaches a second attachment member 1003 of the pair of attachment members to the second location 814 of the annulus 700. Referring to FIG. 10C, the attachment member 1003 includes a securing portion 1016 that extends into the left atrium LA. Referring to FIG. 7D, the attachment member 1003 includes a suture portion 1018 that extends into the left ventricle LV. In a sixth step of the exemplary mitral annuloplasty procedure (as shown by FIGS. 10E and 10F), the suture portion 1012 of the first attachment member 902 and the suture portion 1018 of the second attachment member 1003 are tensioned to create a cinching effect on the annulus 700. That is, the attachment member 902 is tensioned in a direction X and the attachment member 1003 is tensioned in a direction Y. The tensioning of the attachment members 902, 1003 causes the anterior leaflet 705 and the posterior leaflet 706 on the second portion 722 mitral valve MV to coapt. Once the anterior leaflet 705 and the posterior leaflet 706 properly coapt, an anchor 1020 (FIG. 10F) secures the attachment members 902, 1003 together to remove the gap 708 on the second portion 814 of the mitral valve MV. The attachment members 902, 1003 can be placed any distance apart from each other that allows the attachment members to be tensioned and secured together in order to repair at least a portion of the mitral valve MV.

The removal of the gap 708 on the second portion 722 of the mitral valve MV prevents regurgitation of blood from the left ventricle LV to the left atrium LA through the second portion 722 of the mitral valve MV. The attachment members 902, 1003 can be tensioned, and the anchor 1020 can be deployed, by the valve repair device 500 or a separate anchoring device (not shown). If a separate anchoring device is used, the anchoring device enters the left ventricle LV through the apex A of the heart H to engage the suture portions 1012, 1018 of the attachment members 902, 1003. The anchor 1020 may take any suitable form that is capable of securing the first attachment member 602 to the second attachment member 703 to close the gap 708 on at least a portion of the mitral valve MV, such as, for example, any form described in the present application. In situations in which a separate anchoring device is used, each pair of attachment members can be attached to the annulus 700, and, then, the anchoring device can be used to deploy an anchor member to each pair of attachment members.

While the example provided above (in FIGS. 7A-7F and 10A-10F) include using two pairs of attachment members to close the gap 708 between the anterior leaflet 705 and the posterior leaflet 706, it should be understood that any number of pairs of attachment members can be used to close the gap 708. In certain situations, only one pair of attachment members can be required to close the gap 708, and, in other situations, more than two pairs of attachment members can be required to close the gap 708. The pairs of attachment members can be attached to any location on the annulus 700 in order to cause the anterior leaflet 705 and the posterior leaflet 706 to properly coapt.

While the valve repair device 500 and the exemplary annuloplasty procedure provided above is described with reference to repairing the mitral valve MV, it should be understood that the valve repair device and the concepts used in the exemplary mitral annuloplasty procedure can be used to repair any native valve. For example, the valve repair device 500 and the concepts of the exemplary annuloplasty procedure described above can be used to repair the aortic valve AV, the tricuspid valve TV, and the pulmonary valve PV.

Referring to FIGS. 11-15, the valve repair device 500 may engage the anterior leaflet 705 (FIGS. 13 and 15), the posterior leaflet 706 (FIGS. 13 and 15), or both in order to attach an attachment member 1202 (FIGS. 12-15) to the leaflet(s) and secure the leaflet(s) to an outer surface 1100 of the heart H or an inner surface of the heart, such as a papillary muscle of the heart. As described above, the anterior leaflet 705 and the posterior leaflet 706 are attached to the wall of the left ventricle LV by a plurality of chordae tendineae (not shown), which prevent the leaflet(s) from being flailing and allowing regurgitation of blood from the left ventricle LV to the left atrium LA. In certain circumstances, the chordae tendineae can become dysfunctional (e.g., the chordae tendineae may stretch or rupture), which allows the anterior leaflet 705 and/or the posterior leaflet 706 to revert and allow regurgitation of blood into the left atrium LA. The device 500 (shown in FIGS. 11-15) attaches one or more attachment members 1202 to the anterior leaflet 705 and/or the posterior leaflet 706 and secures the leaflet(s) to the outer surface 1100 (or an interior surface such as a papillary muscle) of the heart H in order to prevent the leaflet(s) from reverting as a result of dysfunctional chordae tendineae.

Figure 11:
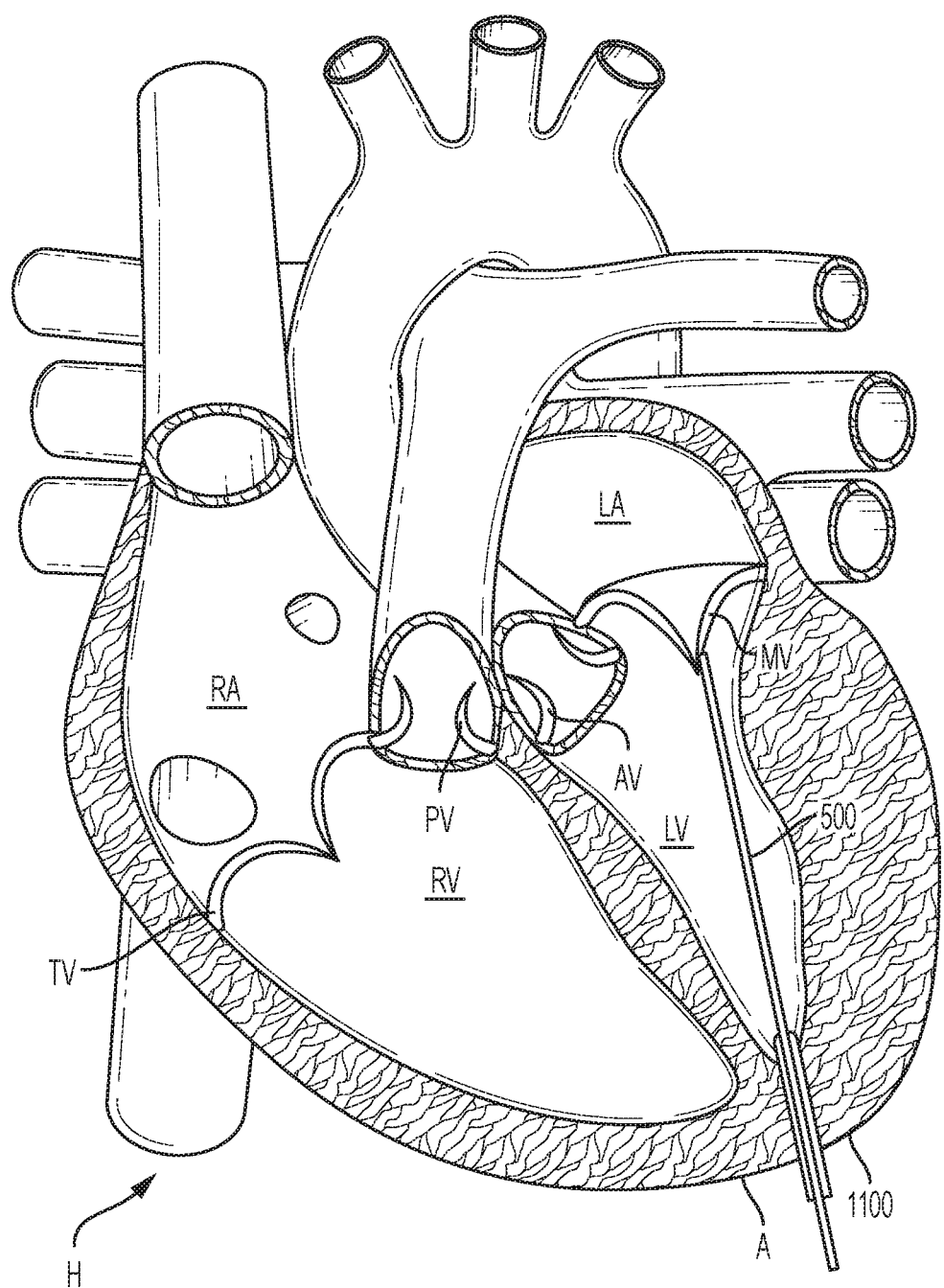
FIG. 11 is a cutaway view of the human heart showing an embodiment of an exemplary valve repair device engaging a leaflet of the mitral valve through the apex of the heart.
Figure 13:
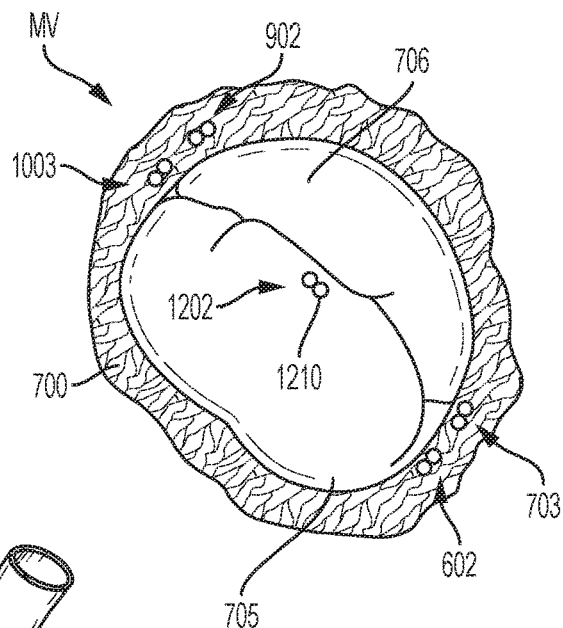
FIG. 13 illustrates the mitral valve shown from the perspective of line A-A in FIG. 12 after the anterior leaflet is anchored to the outer surface of the heart.
Figure 12:
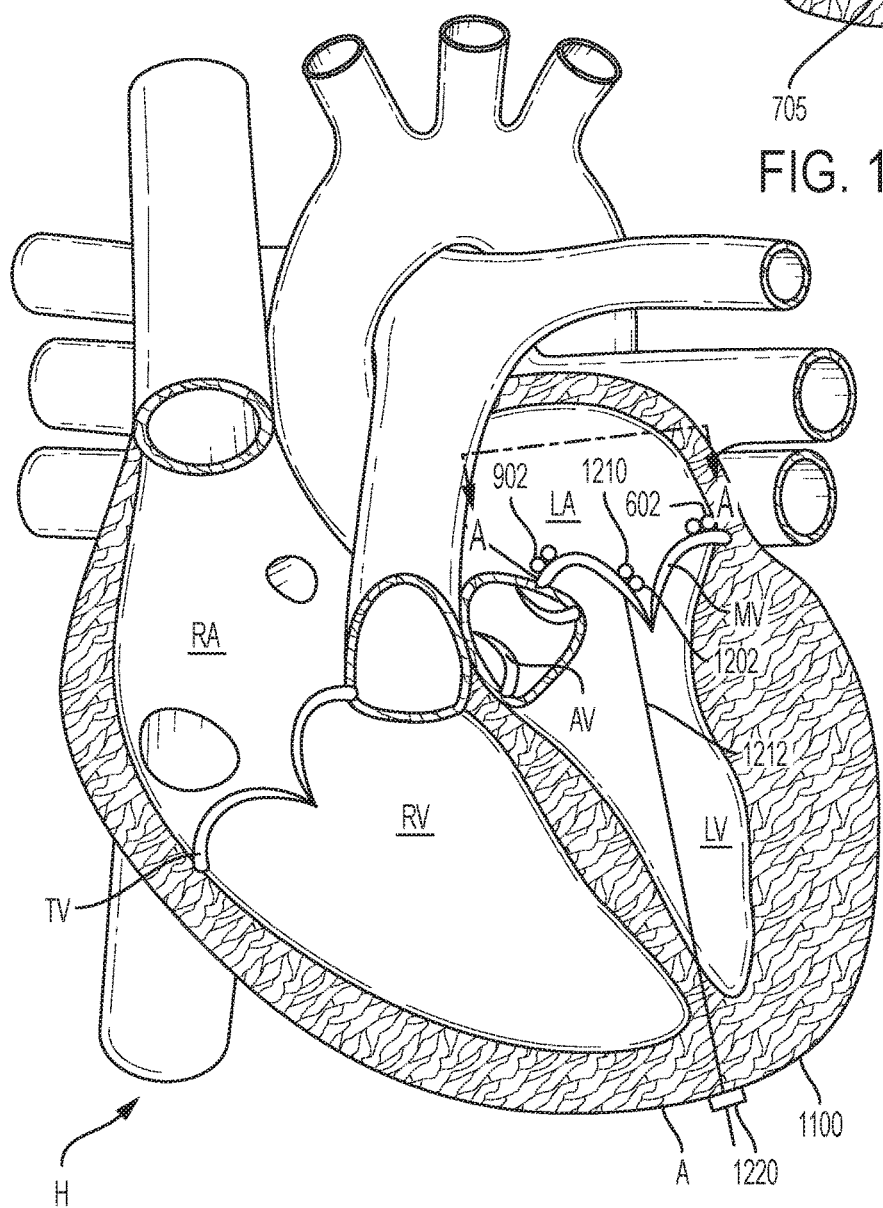
FIG. 12 is a cutaway view of the human heart after the exemplary valve repair device of FIG. 11 attaches an attachment member to the anterior leaflet of the mitral valve and anchors the anterior leaflet to an outer surface of the heart.

FIGS. 11-13 illustrate an exemplary procedure for repairing the anterior leaflet 705 of the mitral valve MV. Referring to FIG. 11, the valve repair device 500 enters the left ventricle LV through the apex A of the heart H and engages the mitral valve MV. Referring to FIGS. 12 and 13, the valve repair device 500 is configured to attach an attachment member 1202 to the anterior leaflet 705 of the mitral valve MV. The attachment member 1202 includes a securing portion 1210 and a suture portion 1212. In the illustrated embodiment, the securing portion 1210 of the attachment member 1202 is a knot. The securing portion 1210 is configured to prevent the attachment member 1202 from being removed from the anterior leaflet 705 or posterior leaflet 706 when a force is applied to the suture portion 1212. In alternative embodiments, the attachment member 1202 may take any suitable form that is capable of securing the anterior leaflet 705 and/or the posterior leaflet 706 to the outer surface 1100 (or an interior surface, such as a papillary muscle) of the heart H, such as, for example, any form described in the present application. The suture portion 1212 of the attachment member 1202 is tensioned to prevent the anterior leaflet 705 from reverting and is attached to the outer surface 1100 (or an interior surface, such as a papillary muscle) of the heart using an anchor member 1220.

Figure 15:
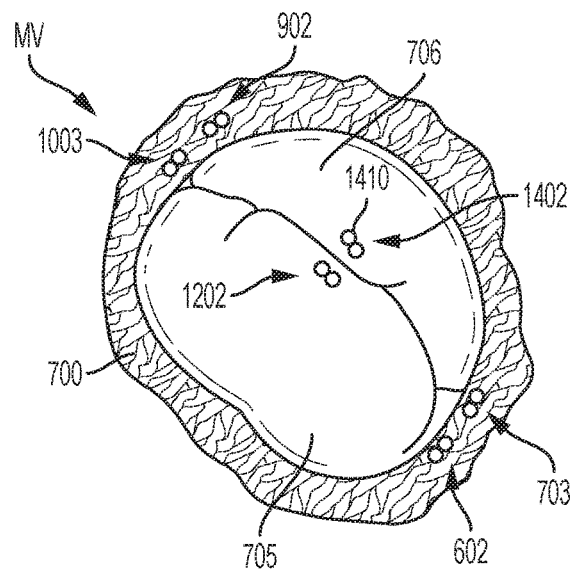
FIG. 15 illustrates the mitral valve shown from the perspective of line A-A in FIG. 14 after the posterior leaflet is anchored to the outer surface of the heart.
Figure 14:
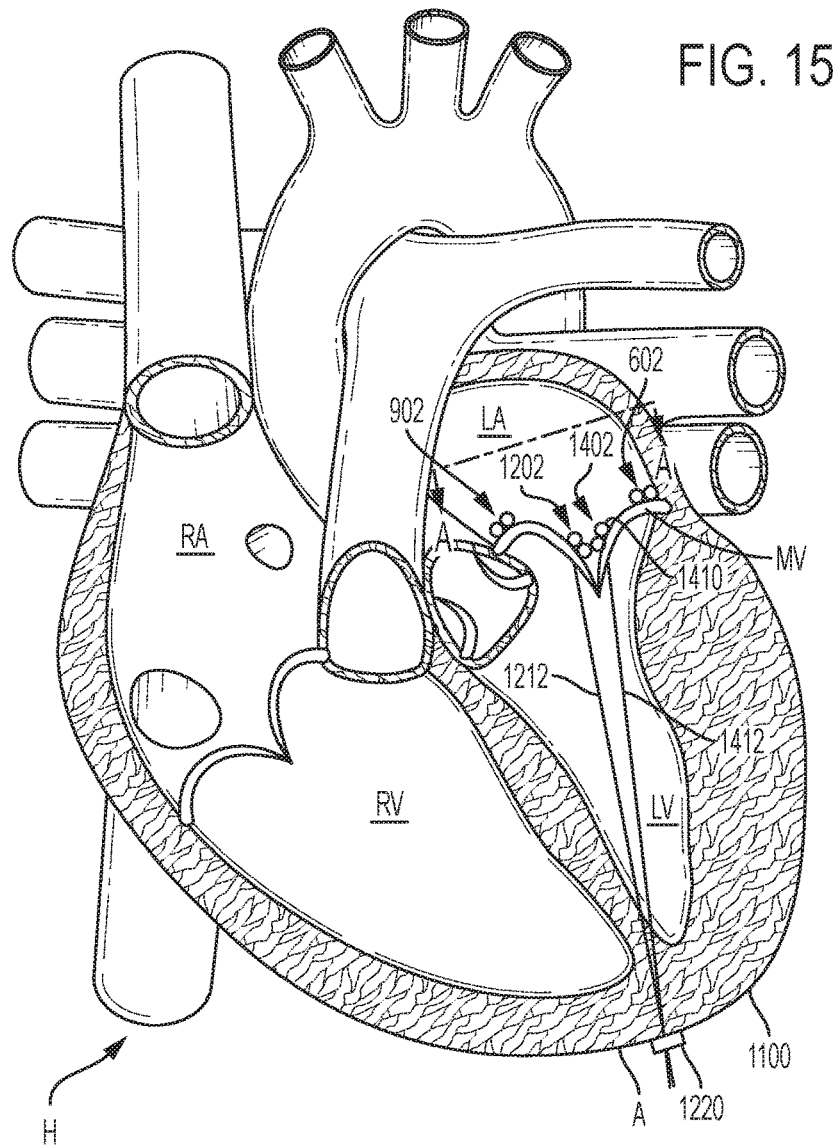
FIG. 14 is a cutaway view of the human heart after the exemplary valve repair device of FIG. 11 attaches an attachment member to the posterior leaflet of the mitral valve and anchors the posterior leaflet to an outer surface of the heart.

FIGS. 11 and 14-15 illustrate an exemplary procedure for repairing the posterior leaflet 706 of the mitral valve MV. Referring to FIG. 11, the valve repair device 500 enters the left ventricle LV through the apex A of the heart H and engages the mitral valve MV. Referring to FIGS. 14 and 15, the valve repair device 500 is configured to attach an attachment member 1402 to the posterior leaflet 706 of the mitral valve MV. The attachment member 1402 includes a securing portion 1410 and a suture portion 1412. In the illustrated embodiment, the securing portion 1410 of the attachment member 1402 is a knot. In alternative embodiments, the attachment member 1402 may take any suitable form that is capable of securing the anterior leaflet 705 and/or the posterior leaflet 706 to the outer surface 1100 (or an interior surface or anatomy, such as a papillary muscle) of the heart H, such as, for example, any form described in the present application. The suture portion 1412 of the attachment member 1402 is tensioned to prevent the posterior leaflet 706 from reverting and is attached to the outer surface 1100 (or an interior surface, such as a papillary muscle) of the heart using an anchor member 1220. In the illustrated example, a single anchor member 1220 is used to attach both the attachment member 1202 attached to the anterior leaflet 705 and the attachment member 1402 attached to the posterior leaflet 706 to the outer surface 1100 (or an interior surface, such as a papillary muscle) of the heart H. In alternative situations, a separate anchor member can be used to attach each of the attachment members 1202, 1402 to the outer surface 1100 (or an interior surface, such as a papillary muscle) of the heart H.

Referring to FIGS. 12-15, an anchor 1220 can be deployed to attach the attachment members 1202, 1402 to the outer surface 1100 (or an interior surface, such as a papillary muscle) of the heart H by the valve repair device 500 or a separate anchoring device (not shown). If the valve repair device 500 is used, after the attachment members 1202, 1402 are attached to the leaflets 705, 706, the device 500 is configured to tension the suture portions 1212, 1412 of the attachment members 1202, 1402 to prevent the leaflets 705, 706 from reverting, and the device 500 is configured to deploy the anchor member 1220. If a separate anchoring device is used, the anchoring device enters the left ventricle LV through the apex A of the heart H to engage the suture portions 1212, 1412 of the attachment members 1202, 1402 and tension the suture portions 1212, 1412 to provide adequate support to prevent the leaflets 705, 706 from reverting. After adequate support is provided to the leaflet 705, 706, the anchor 1220 is deployed to attach the suture portions 1212, 1412 to the outer surface 1100 (or an interior surface such, as a papillary muscle) of the heart H. The anchor 1220 may take any suitable form that is capable of anchoring one or more attachment members to the outer surface 1100 (or an interior surface, such as a papillary muscle) of the heart H. For example, the anchor 1220 can be a clip that clamps onto one or more suture portions, a knot tied at the end of a suture portion, a knot tying the two or more suture portions together, any of the anchors described in this application, any other device capable of securing a suture to an outer wall of the heart or internal tissue of the heart, such as papillary muscle tissue, or the like.

In the illustrated examples shown in FIGS. 12-15, the valve repair device 500 that is used to attach the attachment members 1202, 1402 to the leaflets 705, 706 is the same device that was used to attach the attachment members 602, 703, 902, 1003 to the annulus 700 (as shown in FIGS. 5 through 10A-10F). Having the same device 500 attach attachment members to both the annulus 700 and leaflets 705, 706 is advantageous because it allows for less insertions of devices through the apex A of the heart H. In other situations, a different device can be used to attach attachment members to the leaflets 705, 706 than is used to attach attachment members to the annulus 700.

While the illustrated examples shown in FIGS. 11-15 have a single attachment member 1202 attached to the anterior leaflet 705 and a single attachment member 1402 attached to the posterior leaflet 706, it should be understood that one or more attachment members can be attached to the anterior leaflet and/or the posterior leaflet in order to repair the mitral valve MV. It should also be understood that the one of the anterior leaflet 705 and the posterior leaflet 706 may require more attachment members than the other of the anterior leaflet and the posterior leaflet in order to properly repair the mitral valve MV. In addition, it should be understood that one of the anterior leaflet 705 and the posterior leaflet 706 may require one or more attachment members, and the other of the anterior leaflet and the posterior leaflet may not require any attachment members, to properly repair the mitral valve MV.

Referring to FIGS. 12-15, the valve repair device 500 is shown repairing the leaflets 705, 706 (by attaching attachment members 1202, 1402 to the leaflets) after attachment members 602, 703, 902, 1003 have been attached to the annulus 700. In the illustrated example, the mitral valve is repaired by attaching attachment members to both annulus 700 and the leaflets 705, 706. In situations in which both the annulus 700 and leaflets 705, 706 need to be repaired, the exemplary procedure may include repairing the annulus 700, and, subsequently, repairing the leaflets 705, 706, or vice versa. In the above example, it can be advantageous to repair the annulus 700 prior to repairing one or more of the leaflets 705, 706 because reducing the size of the annulus 700 can make it easier to repair the leaflets 705, 706. In certain situations, only one of the annulus 700 or the leaflets 705, 706 may need to be repaired. The steps of the exemplary procedure shown in FIGS. 5-15 can be completed in any suitable order to repair the mitral valve MV.

While the exemplary procedure described above refers to reparation of the mitral valve, it should be understood that the device 500 and/or the concepts for repairing the mitral valve 500 can be used to repair any native valve. For example, the valve repair device 500 and the concepts of the exemplary procedure described above can be used to repair the aortic valve AV, the tricuspid valve TV, and the pulmonary valve PV.

Referring to FIGS. 16-18 and 19A-19F, another exemplary procedure for mitral annuloplasty is shown using an exemplary embodiment of a valve repair device 1600. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 1708 in FIGS. 17A-17F), which could lead to regurgitation of blood through the mitral valve. The exemplary mitral annuloplasty procedure provides annular support to the mitral valve by reducing the size of the annulus, which allows the leaflets to properly coapt.

Figure 16:
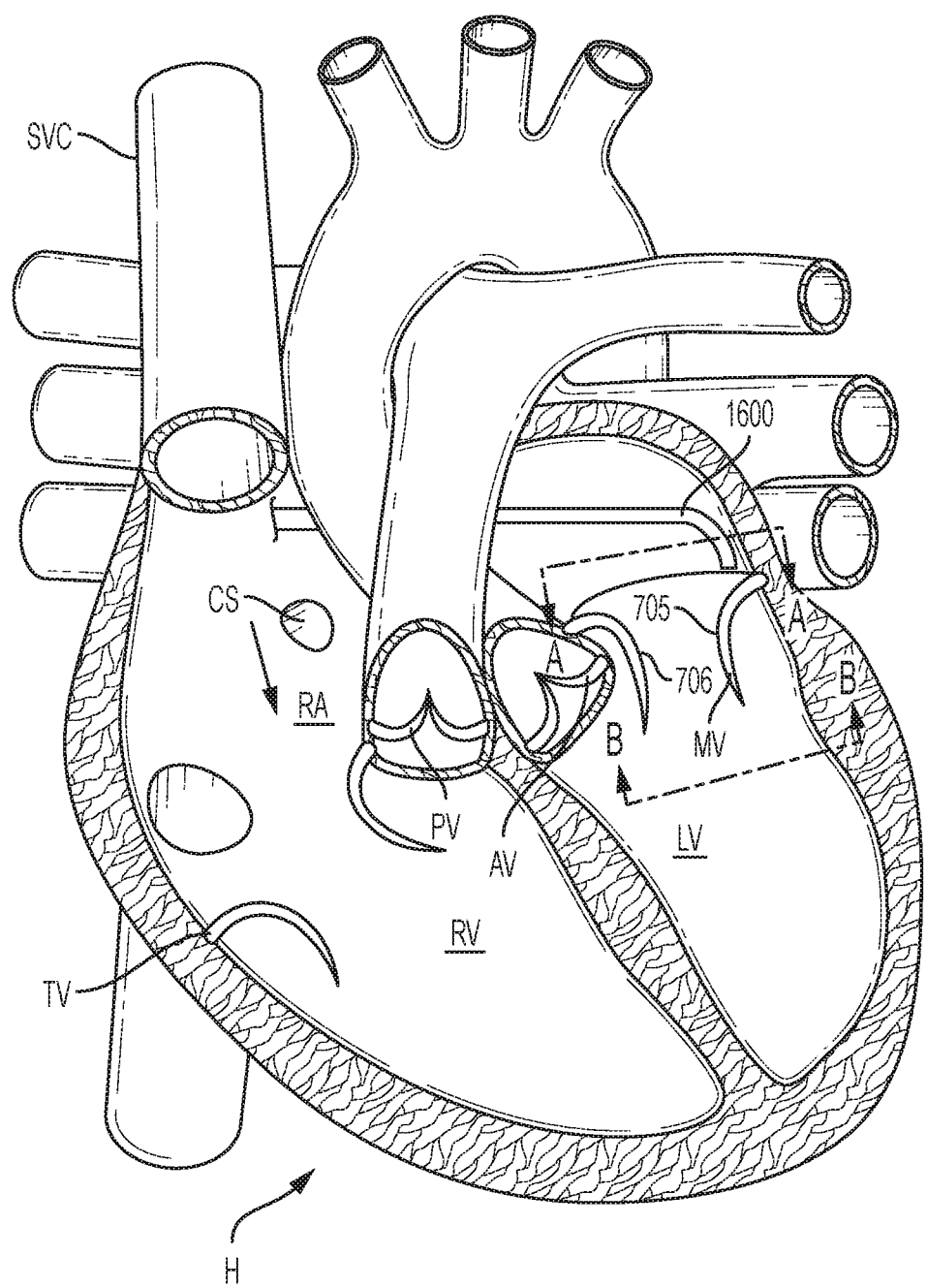
FIG. 16 is a cutaway view of the human heart showing an exemplary embodiment of a valve repair device engaging a first location of the annulus of the mitral valve through the atrial septum of the heart.
Figure 18:
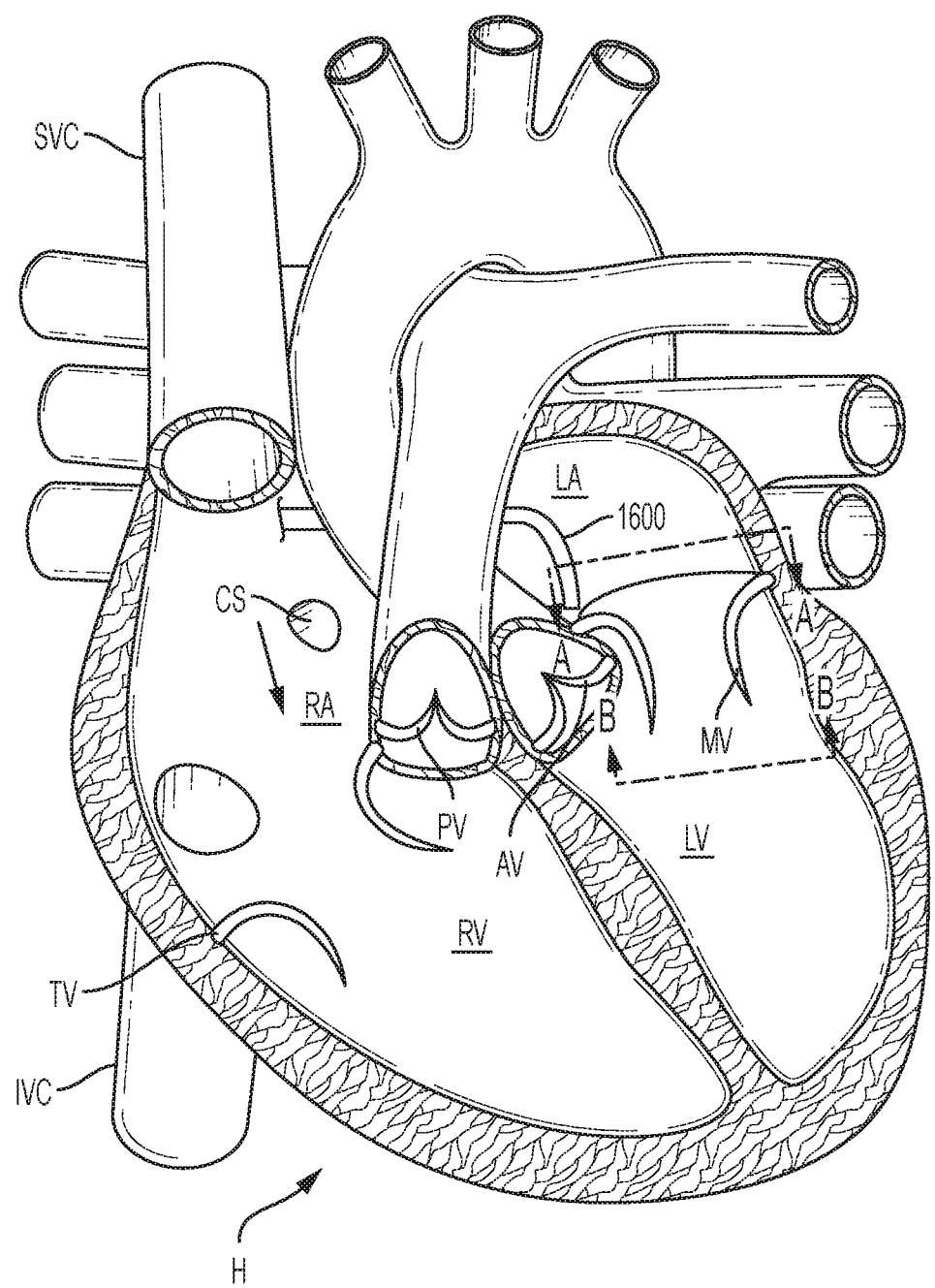
FIG. 18 is a cutaway view of the human heart showing an exemplary embodiment of a valve repair device engaging a second portion of the mitral valve through the atrial septum of the heart.

Referring to FIGS. 16 and 18, the valve repair device 1600 enters the left atrium LA through the atrial septum (not shown) of the heart H. After the valve repair device 1600 enters the left atrium LA, the repair device engages the mitral valve MV. The valve repair device 1600 is configured to attach one or more attachment members to the mitral valve MV. The valve repair device 1600 may take any suitable form that is capable of entering the left atrium LA through the atrial septum of the heart H and attaching one or more attachment members to the mitral valve. For example, the valve repair device 1600 can take the form of the devices described in U.S. Pat. No. 7,635,386 and U.S. Patent Application Publication No. 2014/0114404 A1, which are hereby incorporated by reference in their entireties.

Referring to FIGS. 17A-17F and 19A-19F, the exemplary mitral annuloplasty procedure includes attaching a pair of attachment members (e.g., attachment members 1702, 1703, 1902, 1903) to one or more locations (e.g., location 1704 in FIGS. 17A-17F and location 1914 in FIGS. 19A-19F) of the annulus 700 (FIGS. 17A-17F and FIGS. 19A-19F). In addition, the exemplary procedure includes tensioning the attachment members and anchoring the attachment members of the pair of attachment members together with an anchor member (e.g., anchor members 1720, 1920) to repair at least a portion of the mitral valve MV. Each of the attachment members includes a securing portion and a suture portion. In the illustrated embodiment, the securing portion of each attachment member is a knot. The securing portion is configured to prevent the attachment member from being removed from the annulus 700 when a force is applied to the suture portion. In alternative embodiments, the attachment members may take any suitable form that is capable of providing annular support to the mitral valve, such as, for example, any form described in the present application.

Figure 17A:
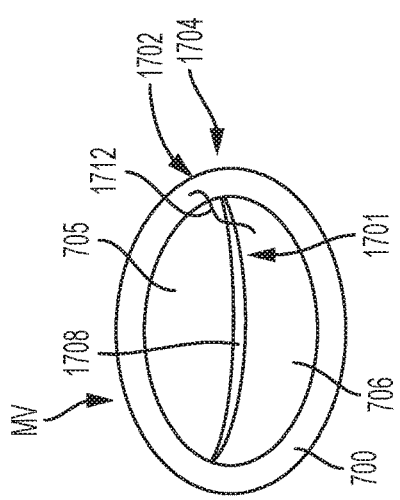
FIGS. 17A, 17C and 17E illustrate the mitral valve shown from the direction represented by line A-A FIG. 16 during an exemplary process for repairing a first portion of the mitral valve using the exemplary valve repair device of FIG. 16.
Figure 17B:
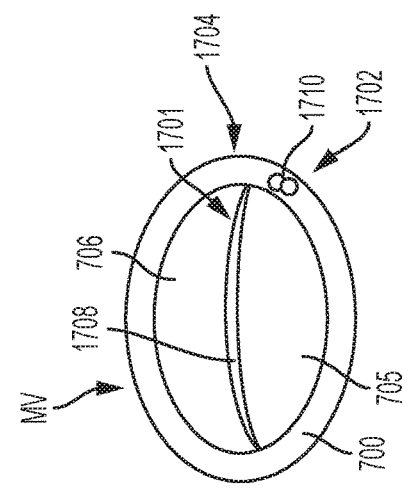
FIGS. 17B, 17D and 17F illustrate the mitral valve shown from the direction represented by line B-B FIG. 16 during an exemplary process for repairing a first portion of the mitral valve using the exemplary valve repair device of FIG. 16.
Figure 17C:
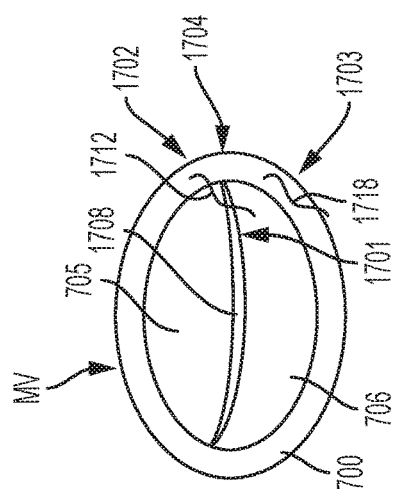
Figure 17D:
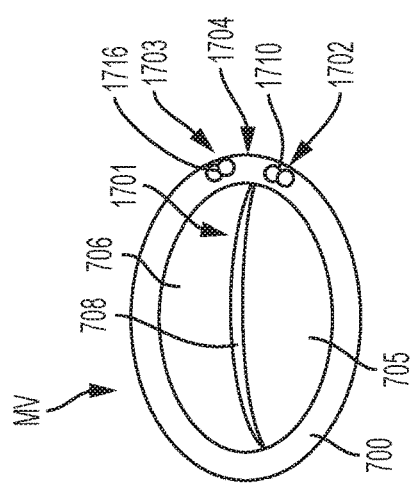
Figure 17E:
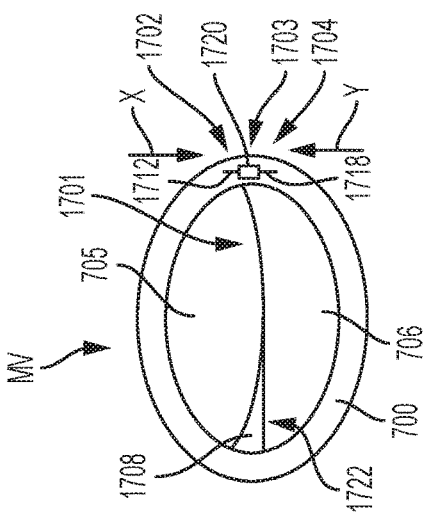
Figure 17F:
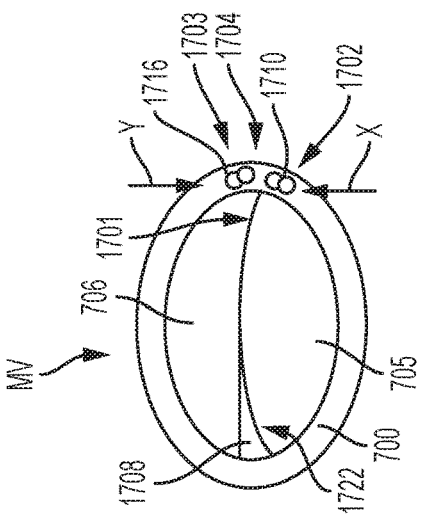

FIGS. 16 and 17A-17F show the valve repair device 1600 attaching attachment members 1702, 1703 to a first location 1704 of the annulus 700 to repair a first portion 1701 of the mitral valve MV. FIGS. 17A, 17C, and 17E illustrate the mitral valve MV from the perspective of line A-A shown in FIG. 16 (e.g., illustrating the mitral valve MV from the left atrium LA), and FIGS. 17B, 17D, and 17F illustrate the mitral valve MV from the perspective of line B-B shown in FIG. 16 (e.g., illustrating the mitral valve MV from the left ventricle). FIGS. 18 and 19A-19F show the valve repair device 1600 attaching attachment members 1902, 1903 to a second location 1904 of the annulus 700 to repair a second portion 1901 of the mitral valve MV. FIGS. 19A, 19C, and 19E illustrate the mitral valve MV from the perspective of line A-A shown in FIG. 18 (e.g., illustrating the mitral valve MV from the left atrium LA), and FIGS. 19B, 19D, and 19F illustrate the mitral valve MV from the perspective of line B-B shown in FIG. 18 (e.g., illustrating the mitral valve MV from the left ventricle).

In a first step of the exemplary mitral annuloplasty procedure (as shown by FIGS. 17A and 17B), the valve device 1600 attaches a first attachment member 1702 of a pair of attachment members to the first location 1704 of the annulus 700. Referring to FIG. 17A, the first attachment member 1702 includes a suture portion 1712 that extends into the left atrium LA. Referring to FIG. 17B, the first attachment member 1702 includes a securing portion 1710 that extends into the left ventricle LV. In a second step of the exemplary mitral annuloplasty procedure (as shown by FIGS. 17C and 17D), the valve device 1600 attaches a second attachment member 1703 of the pair of attachment members to the first location 1704 of the annulus 700. Referring to FIG. 17C, the attachment member 1703 includes a suture portion 1718 that extends into the left atrium LA. Referring to FIG. 17D, the attachment member 1703 includes a securing portion 1716 that extends into the left ventricle LV. In a third step of the exemplary mitral annuloplasty procedure (as shown by FIGS. 17E and 17F), the suture portion 1712 of the first attachment member 1702 and the suture portion 1718 of the second attachment member 1703 are tensioned to create a cinching effect on the annulus 700. That is, the attachment member 1702 is tensioned in a direction X and the attachment member 1703 is tensioned in a direction Y. The tensioning of the attachment members 1702, 1703 causes the anterior leaflet 705 and the posterior leaflet 706 on the first portion 1701 of the mitral valve MV to coapt. Once the anterior leaflet 705 and the posterior leaflet 706 properly coapt, an anchor 1720 (FIG. 17E) secures the attachment members 1702, 1703 together to remove the gap 1708 on the first portion 1701 of the mitral valve MV. The attachment members 1702, 1703 can be placed any distance apart from each other that allows the attachment members to be tensioned and secured together in order to repair at least a portion of the mitral valve MV.

The removal of the gap 1708 on the first portion 1701 of the mitral valve MV prevents regurgitation of blood from the left ventricle LV to the left atrium LA through the first portion 1701 of the mitral valve MV. The attachment members 1702, 1703 can be tensioned, and the anchor 1720 can be deployed, by the valve repair device 1600 or a separate anchoring device (not shown). If a separate anchoring device is used, the anchoring device enters the left atrium LA through the atrial septum of the heart H to engage the suture portions 1712, 1718 of the attachment members 1702, 1703. The anchor 1720 may take any suitable form that is capable of securing the first attachment member 1702 to the second attachment member 1703 to close the gap on at least a portion of the mitral valve MV. For example, the anchor 1720 can be a clip that clamps onto the suture portions 1712, 1718, a knot tying the two suture portions 1712, 1718 together, any of the anchors described in this application, any other device capable of securing two sutures together, or the like, including one or more clasps, locks, fasteners, or similar device(s).

In the illustrated embodiment, the first portion 1702 of the mitral valve MV is closed by the attachment members 1702, 1703 attached at the first location 1704 of the mitral valve MV. However, in this example, the attachment members 1702, 1703 did not completely close the gap 1708 between the anterior leaflet 705 and the posterior leaflet 706. That is, referring to FIGS. 17E and 17F, the gap 708 remains between the anterior leaflet 705 and the posterior leaflet 706 at a second portion 1 of the mitral valve MV.

Referring to FIGS. 18 and 19A-19F, the exemplary procedure for mitral annuloplasty further includes attaching another pair of attachment members to the annulus 700 at a second location 1914 to close the remaining gap 1708 (e.g., the gap 1708 shown in FIGS. 17E-17F and FIGS. 19A-19D) between the anterior leaflet 705 and the posterior leaflet 706. The second pair of attachment members 1902, 1903 can be attached to the annulus 700 by using the same valve repair device 1600 that was used to attach the first pair of attachment members 1702, 1703, or the second pair of attachment members can be attached to annulus by a separate valve repair device (not shown). In the illustrated embodiment, the second pair of attachment members 1902, 1903 are attached to the annulus 700 using the same valve repair device 1600 that was used to attach the first pair of attachment members 1702, 1703 to the annulus 700. In situations where multiple pairs of attachment members are attached to the annulus 700 of the mitral valve MV, it is advantageous to attach the multiple pairs of attachment members to the annulus by the same device because attaching the pairs of attachment members using the same device will allow for less insertions of devices through the atrial septum of the heart H.

Referring to FIGS. 19A and 19B, in a fourth step of the illustrated exemplary mitral annuloplasty procedure, the valve device 1600 attaches a first attachment member 1902 of a pair of attachment members to the second location 1914 of the annulus 700. Referring to FIG. 19A, the first attachment member 1902 includes a suture portion 1912 that extends into the left atrium LA. Referring to FIG. 19B, the first attachment member 1902 includes a securing portion 1910 that extends into the left ventricle LV. In a fifth step of the exemplary mitral annuloplasty procedure (as shown by FIGS. 19C and 19D), the valve device 1600 attaches a second attachment member 1903 of the pair of attachment members to the second location 1914 of the annulus 700. Referring to FIG. 19C, the attachment member 1903 includes a suture portion 1918 that extends into the left atrium LA. Referring to FIG. 19D, the attachment member 1903 includes a securing portion 1916 that extends into the left ventricle LV. In a sixth step of the exemplary mitral annuloplasty procedure (as shown by FIGS. 19E and 19F), the suture portion 1912 of the first attachment member 1902 and the suture portion 1918 of the second attachment member 1903 are tensioned to create a cinching effect on the annulus 700. That is, the attachment member 1902 is tensioned in a direction X and the attachment member 1903 is tensioned in a direction Y. The tensioning of the attachment members 1902, 1903 causes the anterior leaflet 705 and the posterior leaflet 706 on the second portion 1722 of the mitral valve MV to coapt. Once the anterior leaflet 705 and the posterior leaflet 706 properly coapt, an anchor 1920 (FIG. 19E) secures the attachment members 1902, 1903 together to remove the gap 1708 on the second portion 1722 of the mitral valve MV. The attachment members 1902, 1903 can be placed any distance apart from each other that allows the attachment members to be tensioned and secured together in order to repair at least a portion of the mitral valve MV.

The removal of the gap 1708 on the second portion 1722 of the mitral valve MV prevents regurgitation of blood from the left ventricle LV to the left atrium LA through the second portion 1722 of the mitral valve MV. The attachment members 1902, 1903 can be tensioned, and the anchor 1920 can be deployed, by the valve repair device 1600 or a separate anchoring device (not shown). If a separate anchoring device is used, the anchoring device enters the left atrium LA through the atrial septum of the heart H to engage the suture portions 1912, 1918 of the attachment members 1902, 1903. The anchor 1920 may take any suitable form that is capable of securing the first attachment member 1902 to the second attachment member 1903 to close the gap 1708 on at least a portion of the mitral valve MV, such as, for example, any form described in the present application. In situations in which a separate anchoring device is used, each pair of attachment members can be attached to the annulus 700, and, then, the anchoring device can be used to deploy an anchor member to each pair of attachment members.

While the example provided above (in FIGS. 17A-17F and 19A-19F) include using two pairs of attachment members to close the gap 1708 between the anterior leaflet 705 and the posterior leaflet 706, it should be understood that any number of pairs of attachment members can be used to close the gap 1708. In certain situations, only one pair of attachment members can be required to close the gap 1708, and, in other situations, more than two pairs of attachment members can be required to close the gap 1708. The pairs of attachment members can be attached to any location on the annulus 700 in order to cause the anterior leaflet 705 and the posterior leaflet 706 to properly coapt.

Figure 16A:
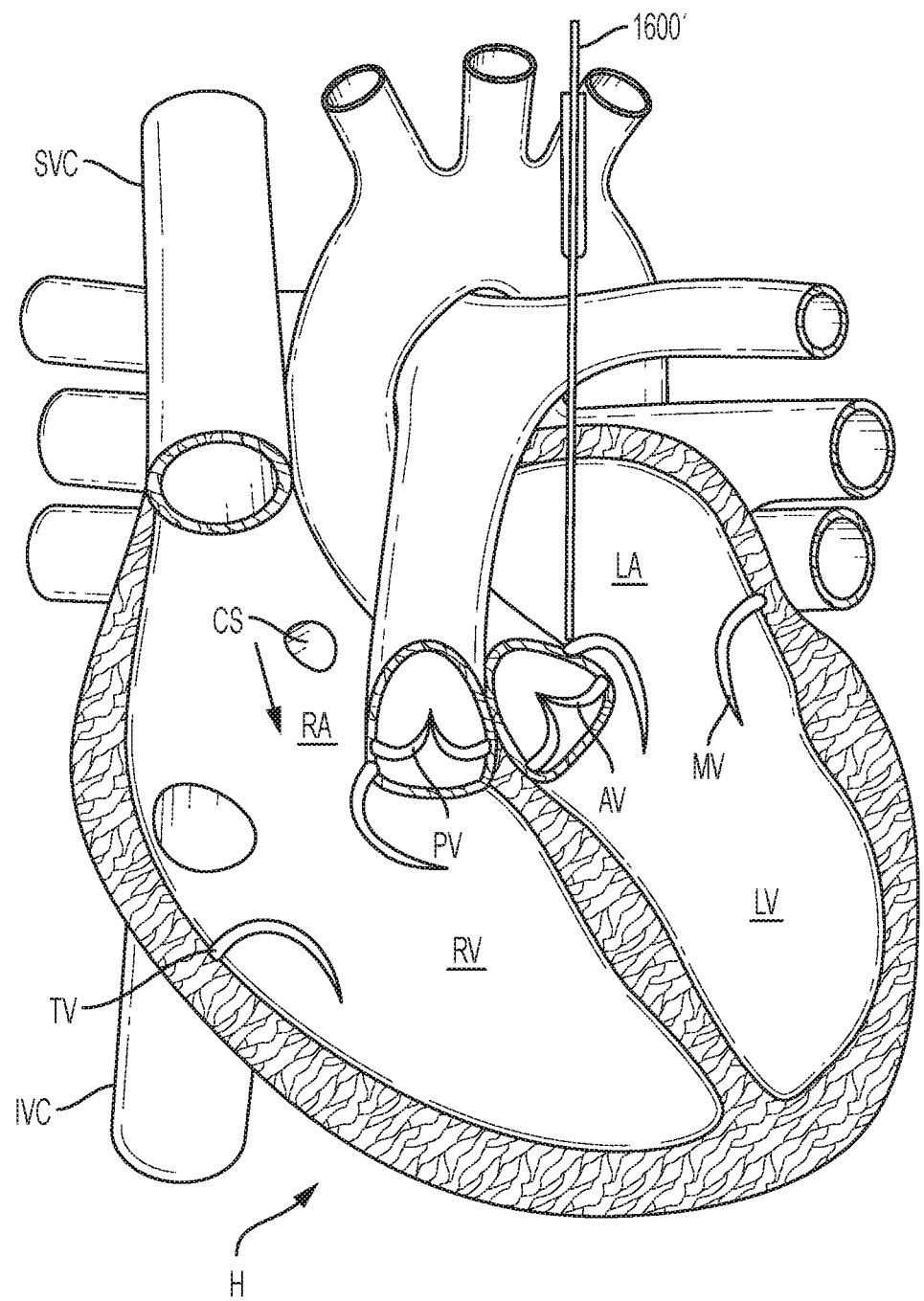
FIG. 16A is a cutaway view of the human heart illustrating an exemplary valve repair device useful for performing a mitral annuloplasty procedure.

Referring to FIG. 16A, in certain embodiments, the exemplary procedure for mitral annuloplasty shown in FIGS. 16-18 and 19A-19F can be completed with a transatrial procedure using valve repair device 1600'. Referring to FIG. 16A, the valve repair device 1600' enters the left atrium LA through an outer wall of the heart H. After the valve repair device 1600' enters the left atrium LA, the repair device engages the mitral valve MV. The valve repair device 1600' is configured to attach one or more attachment members (e.g., any of the attachment members described in the present application) to the mitral valve MV. The valve repair device 1600' may take any suitable form that is capable of entering the left atrium LA through an outer wall of the heart H and attaching one or more attachment members to the mitral valve. For example, the valve repair device 1600' can take the form of the devices described in U.S. Pat. No. 7,635,386 and U.S. Patent Application Publication No. 2014/0114404 A1, which are hereby incorporated by reference in their entireties.

While the valve repair devices 1600, 1600' and the exemplary annuloplasty procedure provided above is described with reference to repairing the mitral valve MV, it should be understood that the valve repair device and the concepts used in the exemplary mitral annuloplasty procedure can be used to repair any native valve. For example, the valve repair devices 1600, 1600' and the concepts of the exemplary annuloplasty procedure described above can be used to repair the aortic valve AV, the tricuspid valve TV, and the pulmonary valve PV.

Referring to FIGS. 20 through 22A-22D, another exemplary procedure for mitral annuloplasty is shown using an exemplary embodiment of a valve repair device 2000. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 2208 in FIGS. 22A-22D), which could lead to regurgitation of blood through the mitral valve. The exemplary mitral annuloplasty procedure provides annular support to the mitral valve by reducing the size of the annulus, which allows the leaflets to properly coapt.

Figure 20:
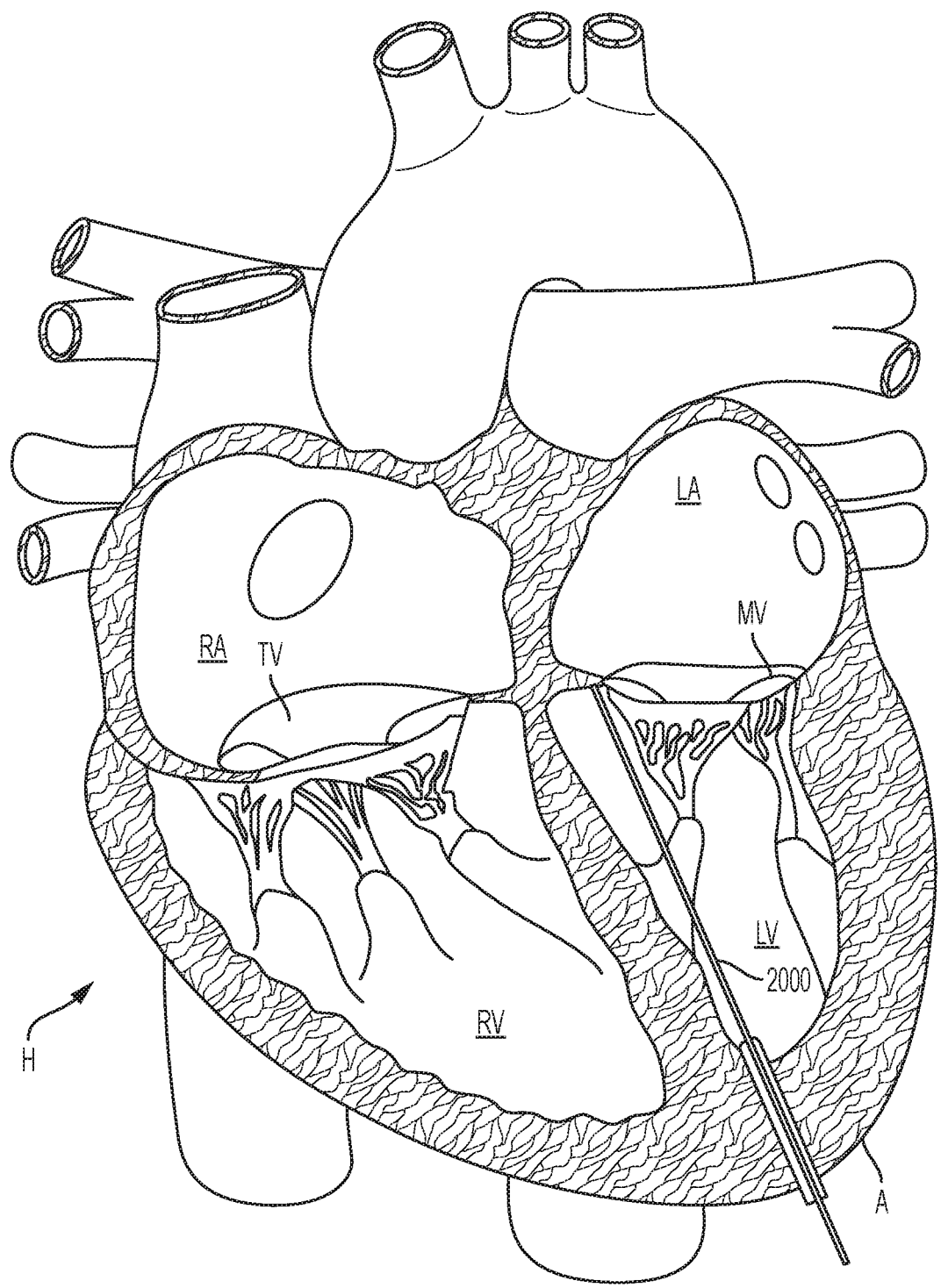
FIG. 20 is a cutaway view of the human heart showing an exemplary embodiment of a valve repair device engaging the annulus of the mitral valve through the apex of the heart.
Figure 21:
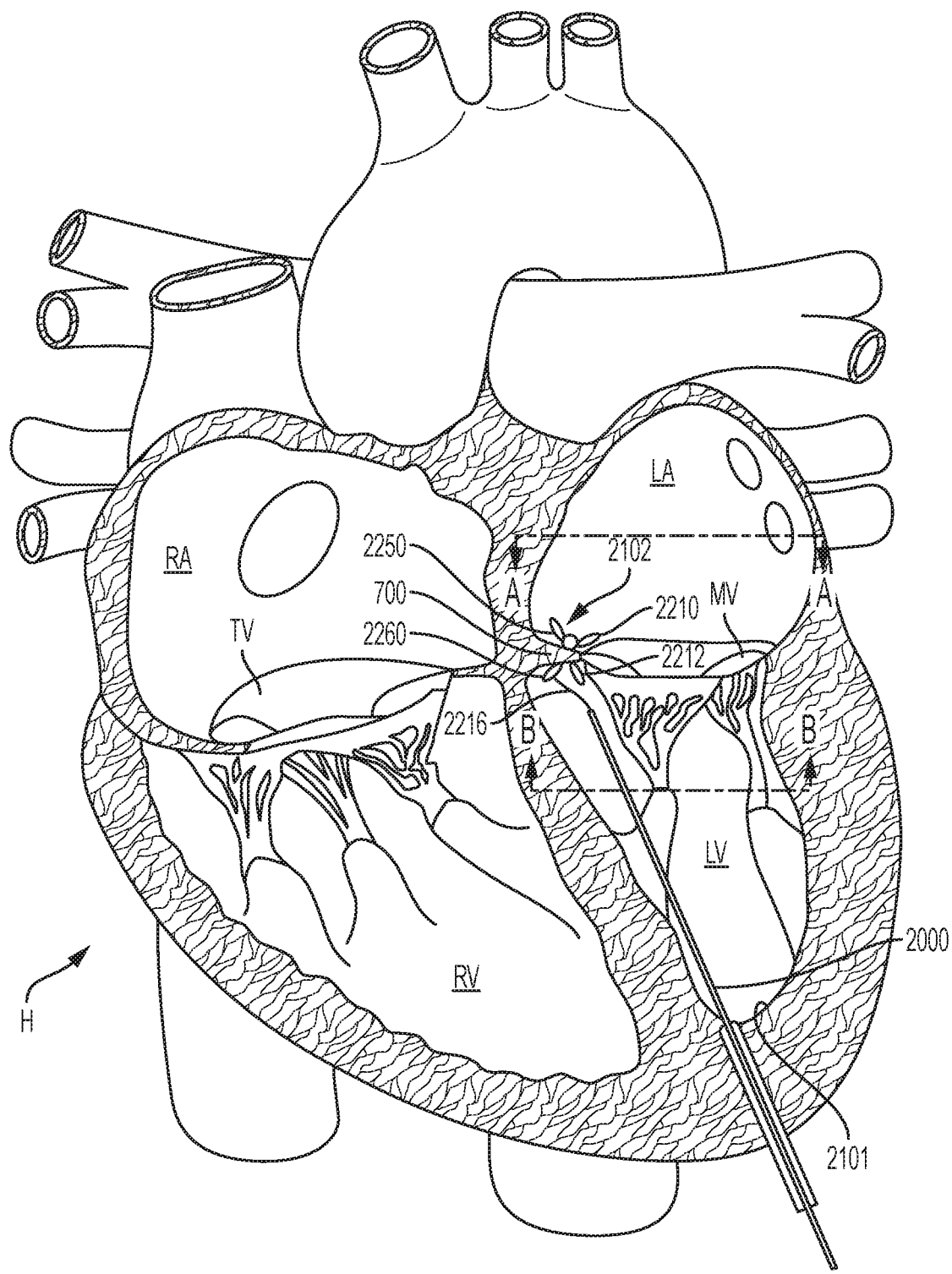
FIG. 21 illustrates the exemplary valve repair device engaging the annulus of the mitral valve, as shown in FIG. 20, after the valve repair device attaches an attachment member to the annulus.

Referring to FIG. 20, the valve repair device 2000 enters the left ventricle LV through the apex A of the heart H. After the valve repair device 2000 enters the left ventricle LV, the repair device engages the mitral valve MV. Referring to FIG. 21, the valve repair device 2000 is configured to attach an attachment member 2102 to the mitral valve MV. The valve repair device 2000 may take any suitable form that is capable of entering the left ventricle LV through the apex A of the heart H and attaching an attachment member 2102 to the mitral valve. For example, the valve repair device 2000 can take the form of the devices described in U.S. Pat. No.

7,635,386 and U.S. Patent Application Publication No. 2014/0114404 A1, which are hereby incorporated by reference in their entireties.

Figure 22C:
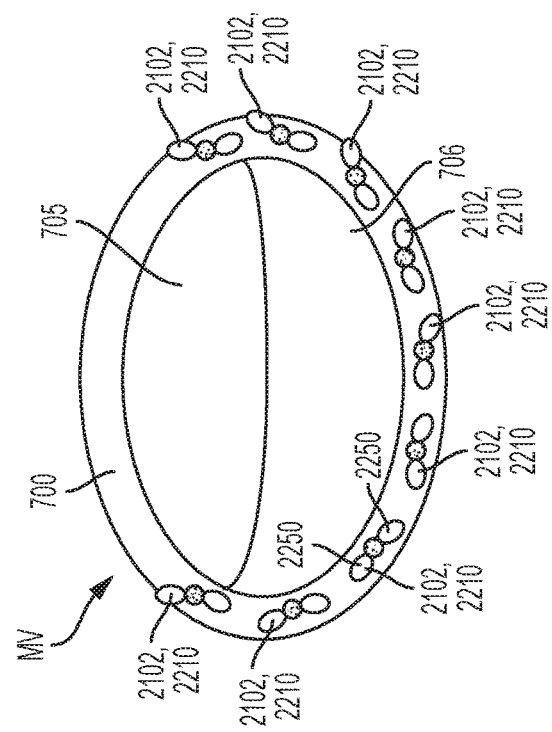
FIGS. 22A and 22C illustrate the mitral valve shown from the direction represented by line A-A FIG. 21 during an exemplary process for repairing a first portion of the mitral valve using the exemplary valve repair device of FIG. 21.
Figure 22D:
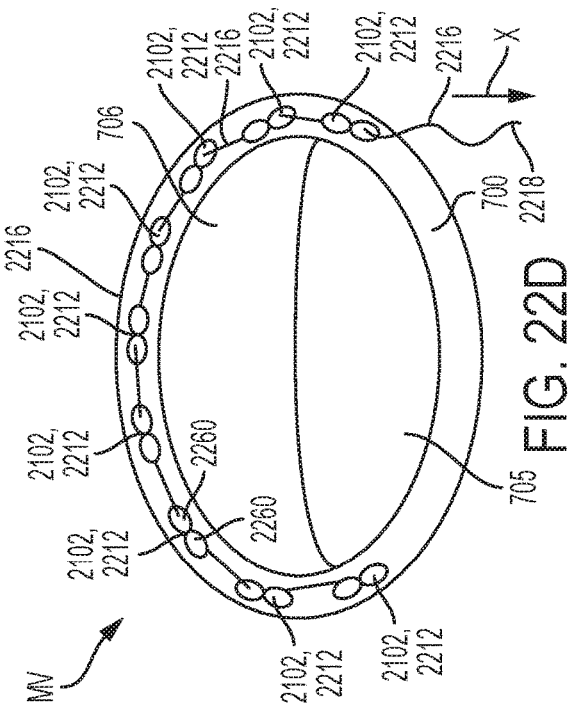
FIGS. 22B and 22D illustrate the mitral valve shown from the direction represented by line B-B FIG. 21 during an exemplary process for repairing a first portion of the mitral valve using the exemplary valve repair device of FIG. 21.
Figure 22A:
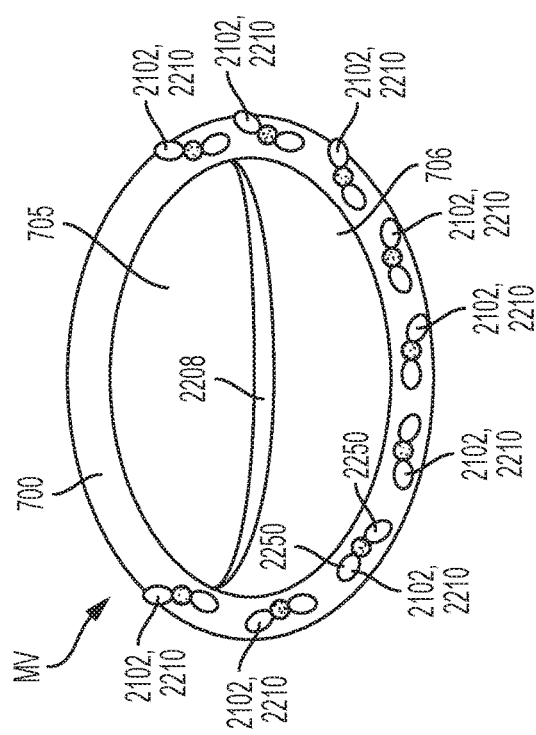
Figure 22B:
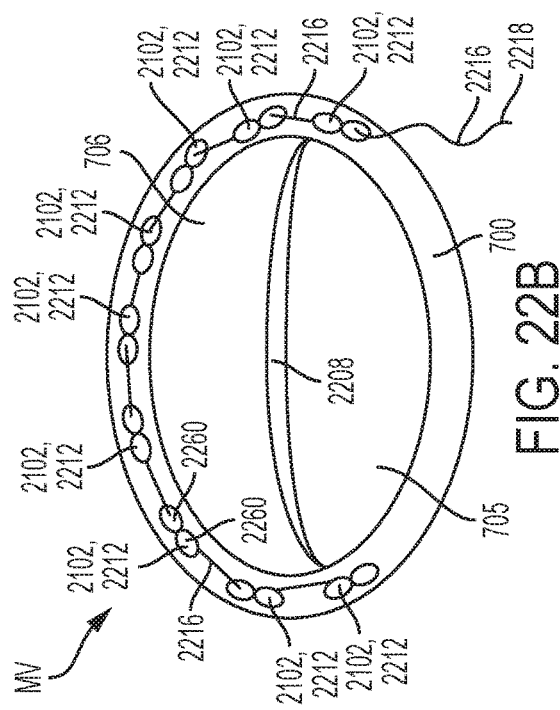

The attachment member 2102 includes an atrial portion 2210 (FIGS. 22A and 22C) and a ventricular portion 2212 (FIGS. 22B and 22D). The atrial portion 2210 and the ventricular portion 2212 are connected together to secure each atrial portion 2210 and ventricular portion 2212 pair to the native valve annulus 700. The atrial portions 2210 and the ventricular portion can be connected together in a wide variety of different ways. For example, the atrial portion 2210 and the ventricular portion can be connected together by a fixed-length suture. As another example, the atrial portion 2210 is fixed to the end of a suture and the ventricular portion 2012 is slideably disposed on the suture and can be secured on the suture relative to the atrial portion 2210 by an anchor (See, for example, anchor 5900 in FIGS. 61A-61C). In the illustrated embodiment, the atrial portion 2210 and the ventricular portion 2212 of the attachment member 2102 are knots. The knots can take a wide variety of different forms. For example, the knots can take any of the forms shown and described in U.S. Patent Application Publication No. 2014/0114404 A1, which is incorporated herein by reference in its entirety. In the illustrated embodiment, the atrial portion 2210 includes two loops 2250 that are connected together at a center 2252 and the ventricular portion 2212 includes two loops 2260 (See FIG. 23).

The atrial portion 2210 is configured to prevent the attachment member 2102 from being removed from the annulus 700 when a force is applied to the ventricular portion 2212. The ventricular portion 2212 is configured to prevent the attachment member 2102 from being removed from the annulus 700 when a force is applied to the atrial portion 2210.

The exemplary mitral annuloplasty procedure includes attaching two or more attachment members 2102 to the annulus 700, in which the two or more attachment members are connected by a suture 2216. The two or more attachment members 2102 can be connected by a suture 2216 prior to being attached to the annulus 700, or the two or more attachment members 2102 can be connected by a suture 2216 after being attached to the annulus 700. In addition, the exemplary procedure includes tensioning the suture 2216 (and, as a result, the two or more attachment members 2102) to reduce the size of the annulus, and, subsequently, fixing the suture once a desired reduction of the size of the annulus is achieved. The suture 2216 can be made of an ePTFE suture, a braid of suture, or any other suitable material. FIGS. 22A and 22C illustrate the mitral valve MV from the perspective of line A-A shown in FIG. 21 (e.g., illustrating the mitral valve MV from the left atrium LA), and FIGS. 22B and 22D illustrate the mitral valve MV from the perspective of line B-B shown in FIG. 21 (e.g., illustrating the mitral valve MV from the left ventricle).

Referring to FIGS. 22A and 22B, in a first step of the exemplary mitral annuloplasty procedure, the valve device 2000 attaches the two or more attachment members 2102 to the annulus 700. In the illustrated embodiment, the device 2000 attaches nine attachment members to the annulus 700. In alternative embodiments, between 2 attachment members and 20 attachment members can be attached to the annulus 700, such as between 4 attachment members and 18 attachment members, such as between 6 attachment members and 16 attachment members, such as between 8 attachment members and 14 attachment members, such as between 10 attachment members and 12 attachment members, such as 11 attachment members. In certain embodiments, the device can attach more than 20 attachment members to the annulus. In an exemplary procedure, the device 2000 attaches twelve attachment members to the annulus 700. Referring to FIG. 22A, each of the attachment members 2102 includes an atrial portion 2210 that extends into the left atrium LA. Referring to FIG. 22B, each of the attachment members 2102 includes a ventricular portion 2212 that extends into the left ventricle LV, and a suture 2216 links each of the ventricular portions 2212 of the attachment members 2102, such that providing a tension to the suture 2216 will cause the attachment members 2102 to reduce the size of the annulus 700. In the illustrated example, the ventricular portions 2212 of the attachment members 2102 are knots, and the suture 2216 is fixed to one attachment member 2102 and runs through the knots of each of the other attachment members. In addition, the suture 2216 includes an excess portion 2218 that is used to tension the suture.

Referring to FIGS. 22C and 22D, in a second step of the exemplary mitral annuloplasty procedure, a force is applied to the excess portion 2218 of the suture 2216 in the direction X (FIG. 22D) to create a cinching effect on the annulus 700. The force applied to the suture 2216 causes a reduction in size of the annulus 700, which causes the anterior leaflet 705 and the posterior leaflet 706 to coapt (e.g., the force causes the gap 2208 to close, as shown in FIGS. 22C and 22D). Once the anterior leaflet 705 and the posterior leaflet 706 properly coapt, the suture 2216 is fixed such that the size of the annulus remains in the reduced state. In one example, the suture 2216 can be fixed to an interior wall 2101 (FIG. 21) of the left ventricle LV. For example, the suture 2216 can be fixed on an interior wall 2101 near the location of insertion by the valve repair device 2000 (or other tensioning device) through the apex A so that suture 2216 is conveniently accessible by the valve repair device (or other tensioning device) if the amount of force applied on the suture 2216 needs to be altered to reduce or expand the size of the annulus. In alternative examples, the suture 2216 can be fixed on any other location of the interior wall 2101 of the left ventricle LA that is accessible by the valve repair device 2000 (or other tensioning device), or the suture may be fixed to the last attachment member 2102 in the series of attachment members by an anchor (See, for example, anchor 5900 in FIGS. 61A-61C).

Adjacent attachment members 2102 can be placed any distance apart from each other that allows the attachment members to be tensioned and secured together in order to repair at least a portion of the mitral valve MV. In certain embodiments, the attachment members 2102 are placed between one trigone (not shown) to another trigone.

The removal of the gap 2208 between the anterior leaflet 705 and the posterior leaflet 706 prevents regurgitation of blood from the left ventricle LV to the left atrium LA through the mitral valve MV. The suture 2216 can be tensioned and fixed by the valve repair device 2000 or a separate tensioning device (not shown). If a separate tensioning device is used, the tensioning device enters the left ventricle LV through the apex A of the heart H to engage the suture 2216.

Figure 23:
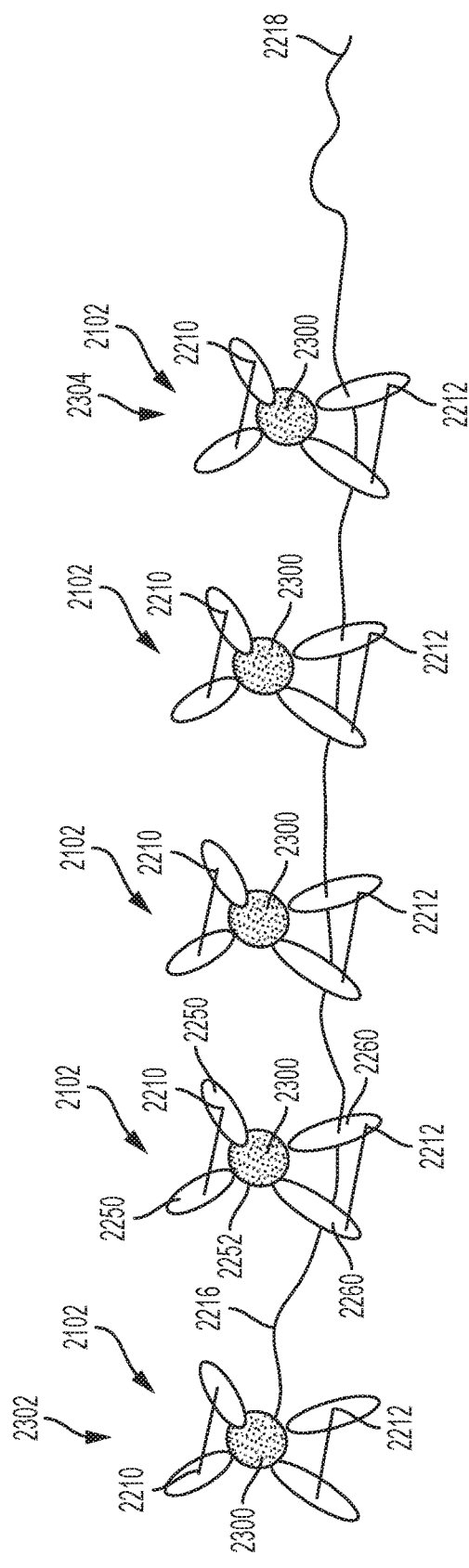
FIG. 23 illustrates an exemplary embodiment of an attachment member and suture configuration used to repair the mitral valve during the exemplary process shown in FIGS. 22A-22D.
Figure 24:
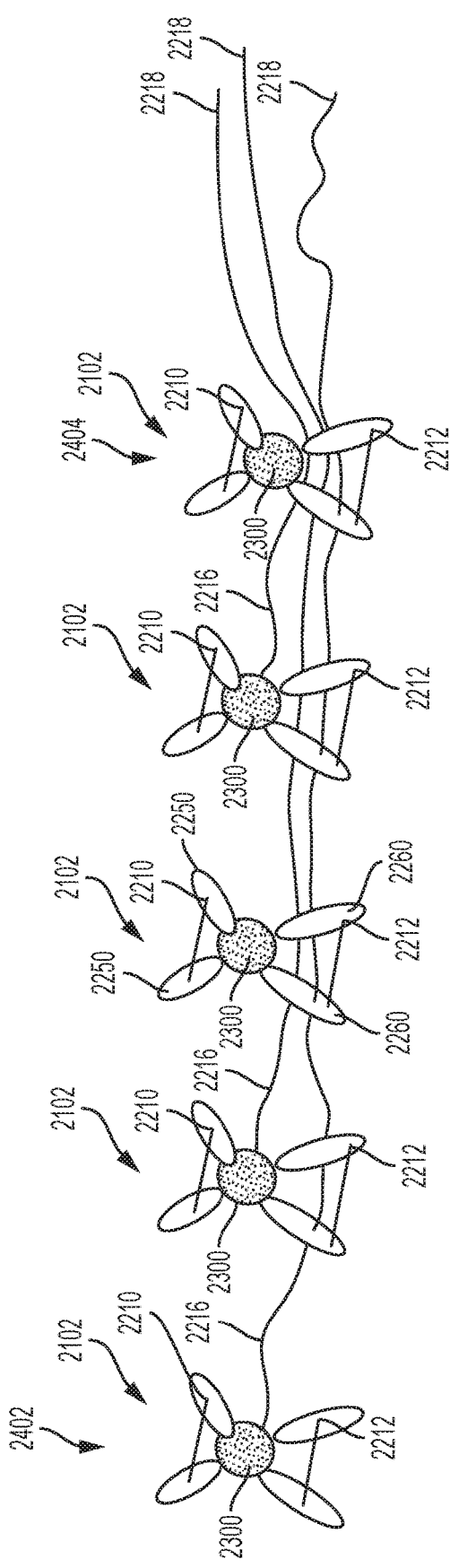
FIG. 24 illustrates another exemplary embodiment of an attachment member and suture configuration used to repair the mitral valve during the exemplary process shown in FIGS. 22A-22D.

The links between the attachment members 2102 and the suture 2216 may take several different forms. Referring to FIGS. 23 and 24, in an exemplary embodiment, each of the attachment members 2102 have an atrial portion 2210, a ventricular portion 2212, and a central portion 2300 that connects the atrial portion to the ventricular portion. Referring to FIG. 23, in one embodiment, the attachment members 2102 are linked by a single suture 2216 that is used to tension the annulus with the attachment members (e.g., a force is applied to the excess portion 2218 of the suture 2216 to provide a tension to the annulus 700 by the attachment members 2102). In this embodiment, the suture 2216 is fixed to the central portion 2300 of an attachment member 2102 that is at a first end of the sequence. For example, the sequence provided in FIG. 23 has a first end 2302 and a second end 2304, and the suture 2216 is fixed to the central portion 2300 of the attachment member 2102 located at the first end 2302 of the sequence. The suture is then slideably coupled to the attachment members 2102 between the first end 2302 and the second end 2304. For example, the suture 2216 can be threaded through loops 2260 of the attachment members 2102 between the first end 2302 and the second end 2304. In addition, in this example, the ventricular portions 2212 of the attachment members 2102 are the portions that are linked by the suture 2216. In an alternative example, the atrial portions 2210 can be the portions that are linked by the suture 2216. A single suture 2216 that links the attachment members in the manner illustrated by FIG. 23 can be used in situations where an even distribution of force or substantially even distribution of force is desired across the annulus to repair the mitral valve.

Referring to FIG. 24, in another example, multiple sutures 2216 are used to provide different levels of tension/cinching around the annulus by the attachment members 2102 (e.g., separate forces are applied to the excess portions 2218 to provide varying tension/cinching to different parts of the annulus where the attachment members 2102 are located). In this example, separate sutures 2216 are attached to three of the five attachment members 2102 and are slideably coupled to other attachment members. In alternative embodiments, individual sutures 2216 can be attached to any number of attachment members 2102 and optionally slideably coupled to none or any number of attachment members in a sequence of attachment members. As such, more or less tensioning/cinching can be tailored to the deficiency of the native valve annulus. In the example illustrated by FIG. 24, the sequence of attachment members 2102 has a first end 2402 and a second end 2404. Each suture 2216 can be slideably coupled to attachment members 2102 that are downstream in the sequence from the connection point with the corresponding attachment member 2102. For example, each suture can thread through one or both loops 2260 of downstream attachment members. The three illustrated sutures 2216 can be independently pulled and anchored. For example, pulling of the top illustrated suture 2218 pulls the fourth attachment member and the attachment member at the second end 2404 relatively together. Pulling of the middle illustrated suture 2218 pulls the second, third, fourth and the attachment member at the second end 2404 relatively together. Pulling of the bottom illustrated suture pulls all five of the attachment members relatively together. However, the attachment members 2102 and sutures 2218 can be tailored to correct regurgitation of individual mitral valves.

Referring to FIGS. 25 through 26A-26D, another exemplary procedure for mitral annuloplasty is shown using an exemplary embodiment of a valve repair device 2500. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 2608 in FIGS. 26A and 26B), which could lead to regurgitation of blood through the mitral valve. The exemplary mitral annuloplasty procedure provides annular support to the mitral valve by reducing the size of the annulus, which allows the leaflets to properly coapt.

Figure 25:
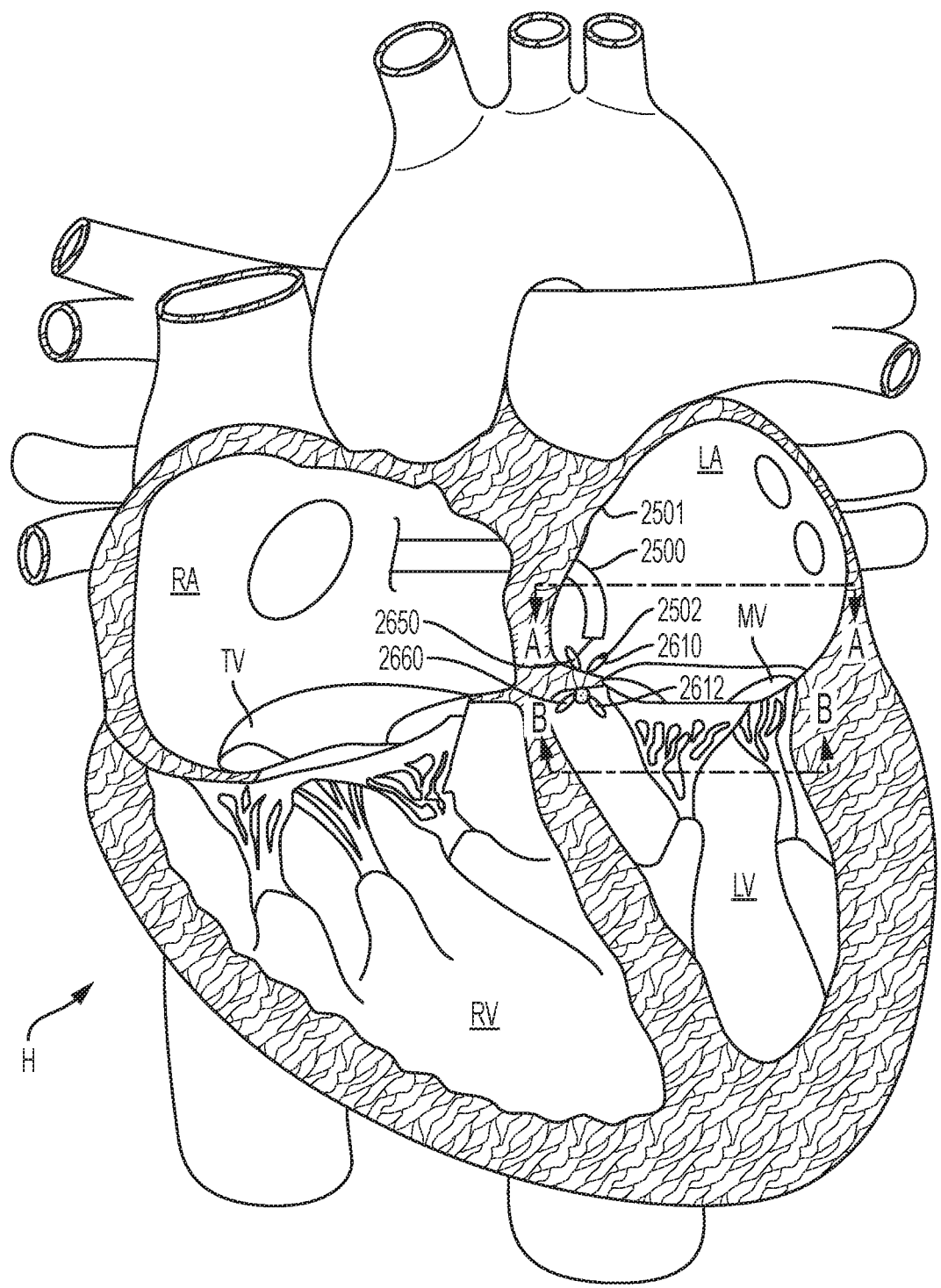
FIG. 25 is a cutaway view of the human heart showing an exemplary embodiment of a valve repair device engaging the annulus of the mitral valve through the atrial septum of the heart.

Referring to FIG. 25, the valve repair device 2500 enters the left atrium LA through the atrial septum (not shown) of the heart H. After the valve repair device 2000 enters the left ventricle LV, the repair device engages the mitral valve MV. The valve repair device 2500 is configured to attach an attachment member 2502 to the mitral valve MV. The valve repair device 2500 may take any suitable form that is capable of entering the left atrium LA through the atrial septum of the heart H and attaching an attachment member 2502 to the mitral valve. For example, the valve repair device 2500 can take the form of the devices described in U.S. Pat. No. 7,635,386 and U.S. Patent Application Publication No. 2014/0114404 A1, which are hereby incorporated by reference in their entireties.

The attachment member 2502 includes an atrial portion 2610 (FIGS. 22A and 22C) and a ventricular portion 2612 (FIGS. 22B and 22D). The atrial portion 2610 and the ventricular portion 2612 are connected together to secure each atrial portion 2610 and ventricular portion 2612 pair to the native valve annulus 700. The atrial portions 2610 and the ventricular portion 2612 can be connected together in a wide variety of different ways. For example, the atrial portion 2610 and the ventricular portion can be connected together by a fixed length suture. As another example, the ventricular portion 2612 is fixed to the end of a suture and the atrial portion 2610 is slideably disposed on the suture and can be secured on the suture relative to the ventricular portion 2612 by an anchor (See, for example, anchor 5900 in FIGS. 61A-61C).

In the illustrated embodiment, the atrial portion 2610 and the ventricular portion 2612 of the attachment member 2102 are knots. The knots can take a wide variety of different forms. For example, the knots can take any of the forms shown and described in U.S. Patent Application Publication No. 2014/0114404 A1. In the illustrated embodiment, the atrial portion 2610 includes two loops 2650 and the ventricular portion 2612 includes two loops 2660.

The atrial portion 2610 is configured to prevent the attachment member 2502 from being removed from the annulus 700 when a force is applied to the ventricular portion 2612. The ventricular portion 2612 is configured to prevent the attachment member 2502 from being removed from the annulus 700 when a force is applied to the atrial portion 2610.

Figure 26C:
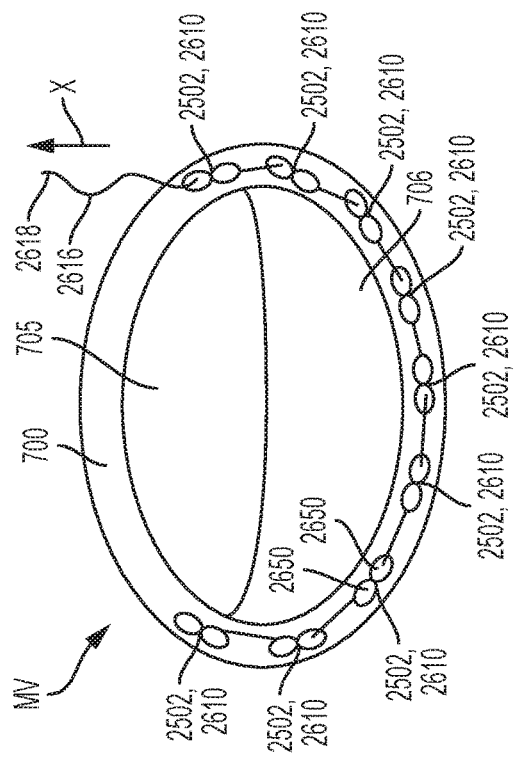
FIGS. 26A and 26C illustrate the mitral valve shown from the direction represented by line A-A FIG. 25 during an exemplary process for repairing a first portion of the mitral valve using the exemplary valve repair device of FIG. 25.

The exemplary mitral annuloplasty procedure includes attaching two or more attachment members 2502 to the annulus 700, in which the two or more attachment members are linked by a suture 2616. The two or more attachment members 2502 can be linked by a suture 2616 prior to being attached to the annulus 700, or the two or more attachment members 2502 can be connected by a suture 2616 after being attached to the annulus 700. In addition, the exemplary procedure includes tensioning the suture 2616 (and, as a result, the two or more attachment members 2502) to reduce the size of the annulus, and, subsequently, fixing the suture once a desired reduction of the size of the annulus is achieved. The suture 2616 can be made of an ePTFE suture, a braid of suture, or any other suitable material. FIGS. 26A and 26C illustrate the mitral valve MV from the perspective of line A-A shown in FIG. 25 (e.g., illustrating the mitral valve MV from the left atrium LA), and FIGS. 26B and 26D illustrate the mitral valve MV from the perspective of line B-B shown in FIG. 25 (e.g., illustrating the mitral valve MV from the left ventricle).

Figure 26D:
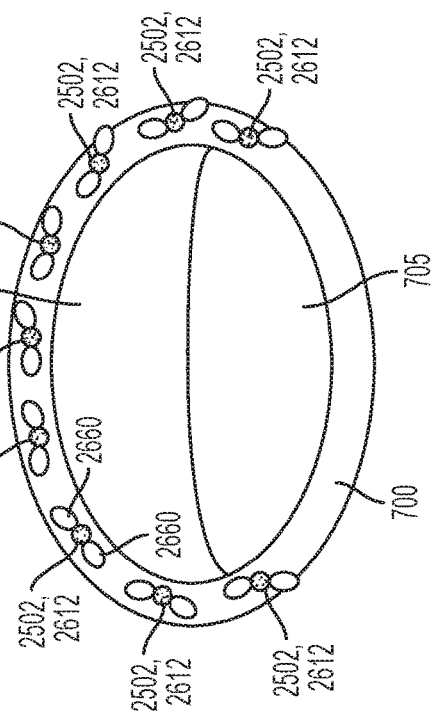
FIGS. 26B and 26D illustrate the mitral valve shown from the direction represented by line B-B FIG. 25 during an exemplary process for repairing a first portion of the mitral valve using the exemplary valve repair device of FIG. 25.
Figure 26A:
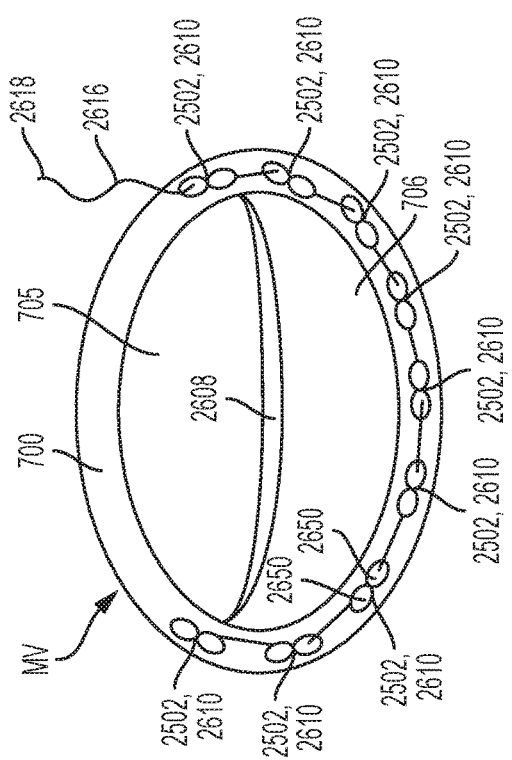
Figure 26B:
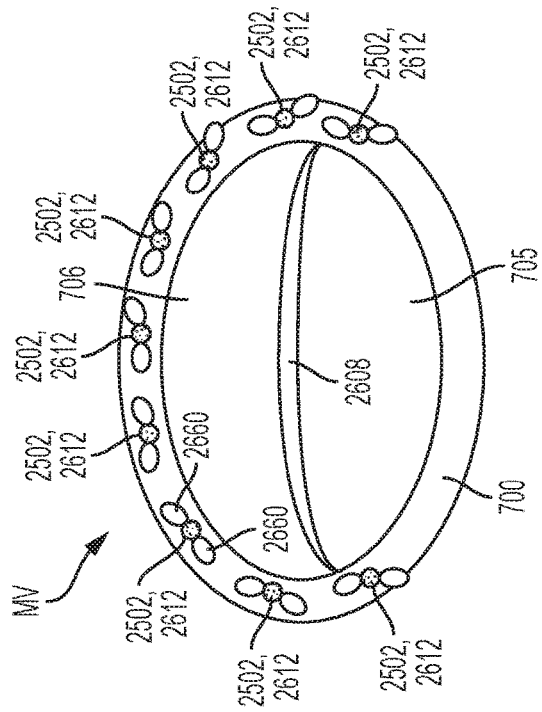

Referring to FIGS. 26A and 26B, in a first step of the exemplary mitral annuloplasty procedure, the valve device 2500 attaches the two or more attachment members 2502 to the annulus 700. In the illustrated embodiment, the device 2500 attaches nine attachment members to the annulus 700. In alternative embodiments, between 2 attachment members and 20 attachment members can be attached to the annulus 700. Referring to FIG. 26A, each of the attachment members 2502 includes an atrial portion 2610 that extends into the left atrium LA. Referring to FIG. 26B, each of the attachment members 2502 includes a ventricular portion 2612 that extends into the left ventricle LV. A suture 2616 links each of the atrial portions 2610 of the attachment members 2502, such that providing a tension to the suture 2616 will cause the attachment members 2502 to reduce the size of the annulus 700. In the illustrated example, the atrial portions 2610 of the attachment members 2102 are knots, and the suture 2616 is fixed to one attachment member 2102 and runs through the knots of each of the other attachment members. In addition, the suture 2216 includes an excess portion 2218 that is used to apply tension to the suture.

Referring to FIGS. 26C and 26D, in a second step of the exemplary mitral annuloplasty procedure, a force is applied to the excess portion 2618 of the suture 2616 in the direction X (FIG. 26C) to create a cinching effect on the annulus 700. The force applied to the suture 2216 causes a reduction in size of the annulus 700, which causes the anterior leaflet 705 and the posterior leaflet 706 to coapt (e.g., the force causes the gap 2608 to close, as shown in FIGS. 26C and 26D). Once the anterior leaflet 705 and the posterior leaflet 706 properly coapt, the suture 2616 is fixed such that the size of the annulus remains in the reduced state. In one example, the suture 2616 can be fixed to an interior wall of the left atrium LA. Alternatively, the suture 2616 the suture may be fixed to the last attachment member 2502 in the series of attachment members by an anchor (See, for example, anchor 5900 in FIGS. 61A-61C).

Adjacent attachment members 2502 can be placed any distance apart from each other that allows the attachment members to be tensioned and secured together in order to repair at least a portion of the mitral valve MV. In certain embodiments, the attachment members 2102 are placed between one trigone (not shown) to another trigone).

The removal of the gap 2608 between the anterior leaflet 705 and the posterior leaflet 706 prevents regurgitation of blood from the left ventricle LV to the left atrium LA through the mitral valve MV. The suture 2616 can be tensioned and fixed by the valve repair device 2500 or a separate tensioning device (not shown).

The link(s) between the attachment members 2502 and the suture 2616 may take several different forms, such as, for example, any form described in the present application. In certain embodiments, multiple sutures 2616 can be used to tension the annulus, as shown in FIG. 24.

Referring to FIG. 16A, in certain embodiments, the exemplary procedure for mitral annuloplasty shown in FIGS. 25 and 26A-26D can be completed with a transatrial procedure using valve repair device 1600'. Referring to FIG. 16A, the valve repair device 1600' enters the left atrium LA through an outer wall of the heart H. After the valve repair device 1600' enters the left atrium LA, the repair device engages the mitral valve MV. The valve repair device 1600' is configured to attach one or more attachment members (e.g., any of the attachment members described in the present application) to the mitral valve MV. The valve repair device 1600' may take any suitable form that is capable of entering the left atrium LA through an outer wall of the heart H and attaching one or more attachment members to the mitral valve. For example, the valve repair device 1600' can take the form of the devices described in U.S. Pat. No. 7,635,386 and U.S. Patent Application Publication No. 2014/0114404 A1, which are hereby incorporated by reference in their entireties.

While the example provided above (in FIGS. 22A-22D and 26A-26D) include using two or more attachment members connected or linked by one or more sutures to close the gap 2208, 2608 between the anterior leaflet 705 and the posterior leaflet 706, it should be understood that any number of attachment members connected or linked by sutures can be used. In certain situations, only one sequence of attachment members connected or linked by a suture can be required to close the gap 2208, 2608. In other situations, more than one sequence of attachment members connected or linked by one or more suture can be used to close the gap 2208, 2608. The attachment members can be attached to any location on the annulus 700 in order to cause the anterior leaflet 705 and the posterior leaflet 706 to properly coapt.

While the valve repair devices 2000, 2500, 1600' and the exemplary annuloplasty procedures provided above are described with reference to repairing the mitral valve MV, it should be understood that the valve repair devices and the concepts used in the exemplary mitral annuloplasty procedures can be used to repair any native valve. For example, the valve repair devices 2000, 2500, 1600' and the concepts of the exemplary annuloplasty procedures described above can be used to repair the aortic valve AV, the tricuspid valve TV, and the pulmonary valve PV.

Figure 27:
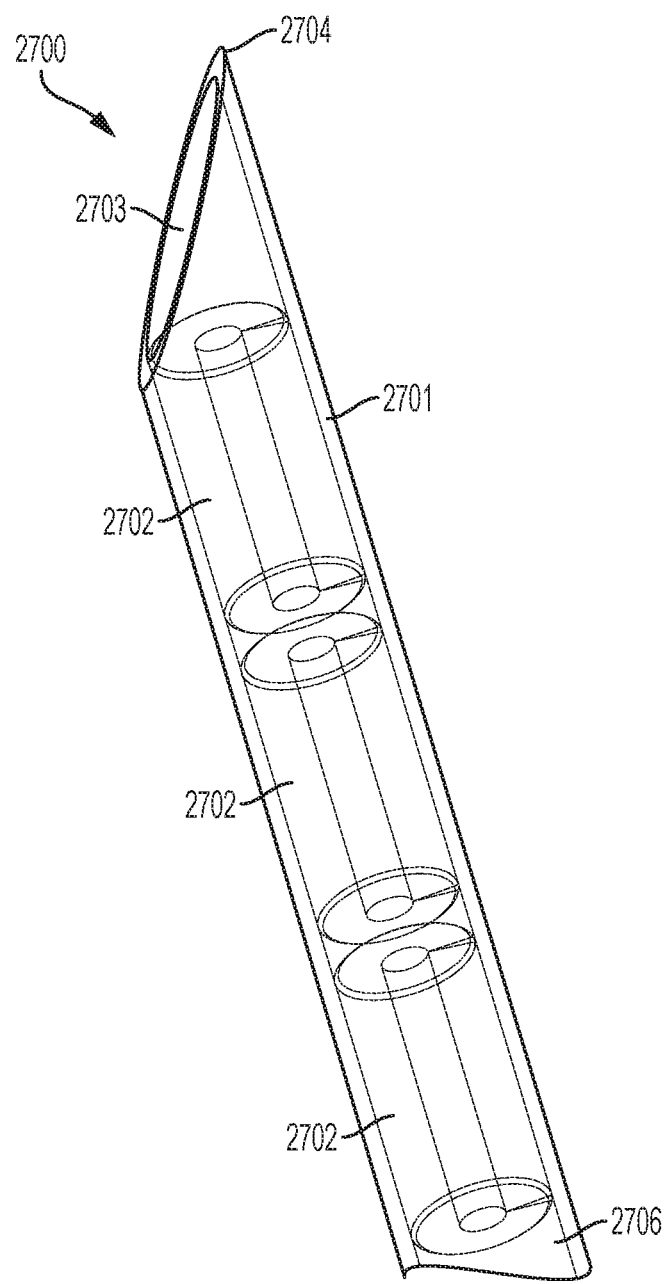
FIG. 27 illustrates another exemplary embodiment of a valve repair device.
Figure 28:
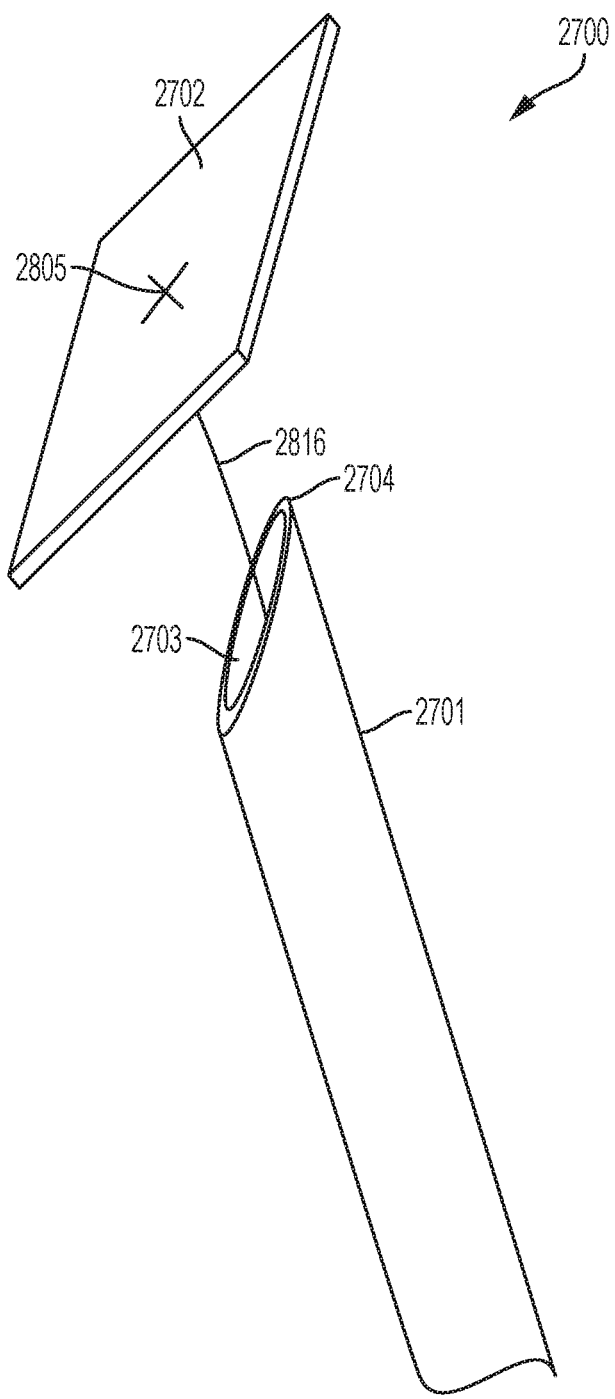
FIG. 28 illustrates the exemplary valve repair device of FIG. 27, in which the valve repair device is configured to provide an exemplary embodiment of a pledget.
Figure 29:
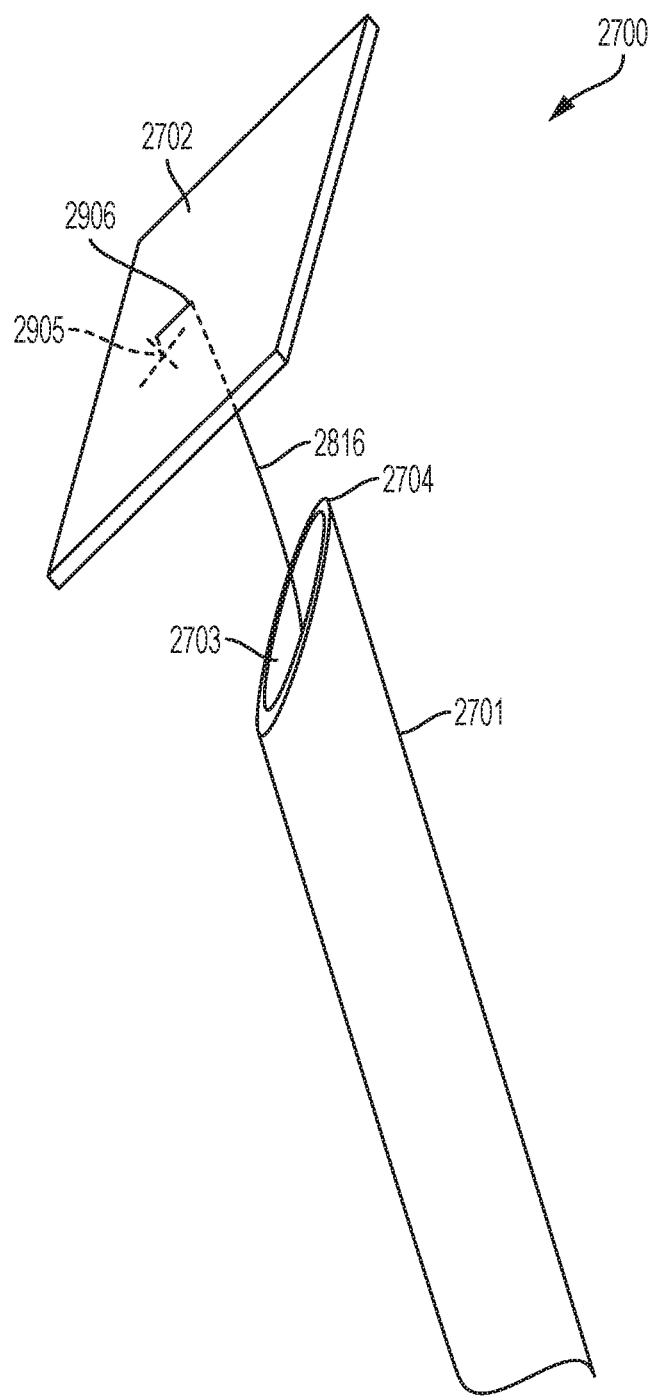
FIG. 29 illustrates the exemplary valve repair device of FIG. 27, in which the valve repair device is configured to provide another exemplary embodiment of a pledget.

Referring to FIGS. 27-29, an exemplary valve repair device 2700 for repairing the mitral valve includes a delivery member 2701 and an advancement member (not shown). The delivery member 2701 can optionally include a suction device for holding valve tissue, such as valve annulus tissue, against the valve repair device 2700. Details of one suction device that can be used are disclosed in U.S. Patent Application No. 62/326,609, filed on Apr. 22, 2016, entitled "Catheter with a Collapsible Funnel-Shaped Suction Cup for Placing Prosthetic Chords for a Heart Valve," the disclosure of which is incorporated herein by reference in its entirety.

The advancement member is configured to move one or more pledgets 2702 (e.g., one or more attachment members), such that the pledgets can be deployed through an outlet 2703 of the delivery member 2701. In certain embodiments, the delivery member 2701 of the valve repair device 2700 includes a puncturing member 2704 that is configured to puncture tissue member (e.g., the annulus of the mitral valve, the leaflets of the mitral valve, etc.). For example, the delivery member 2701 can be a hollow needle. The valve repair device 2700 is configured to deploy one or more pledgets 2702 (by the advancement member) out of the outlet 2703 of the delivery member 2701 and attach the pledgets to a tissue member. The pledgets 2702 can be linked in a wide variety of different ways. For example, the pledgets 2702 can be linked in any of the ways the attachment members 2502 can be linked, as described above. In the illustrated embodiment, the pledgets 2702 are linked to each other by a suture 2816 (FIGS. 28 and 29). The pledgets 2702 can be configured to be crimped and compressed to occupy less space in the shaft 2706 of the of the delivery member 2701. In the example illustrated by FIG. 27, rectangular pledgets 2702 are rolled into a cylindrical configuration. However, the pledgets 2702 can have any compressed configuration and any expanded configuration.

Upon being deployed through the outlet 2703 of the delivery member 2701, the pledgets 2702 are configured to expand. The pledgets 2702 can be made out of, for example, fabric, such as, cotton, PTFE, etc. fabric, expandable foam, shape memory alloy material, such as nitinol, a mesh, a mesh of shape memory allow material, such as Nitinol, any other compressible material that is capable of adequately securing the pledget against a tissue, or any combination thereof. In certain embodiments, the pledgets 2702 have radiopaque markers that are visible on echocardiography and fluoroscopy, which allows the location of the pledgets to be identified.

Referring to FIG. 28, in one embodiment, an individual suture 2816 is attached to each of the pledgets 2702 in a single location 2805. Referring to FIG. 29, in another embodiment, one suture 2816 is attached a first the pledget at a first location 2905, is threaded over the pledget, and is threaded back through the pledget at a second location 2906. In this example, subsequent pledgets 2702 are slideably disposed on the suture 2816 by threading the suture 2816 through each pledget at the first and second locations 2905, 2906. In the embodiment shown in FIG. 29, the suture 2816 includes a tensioning portion 3026 (See FIGS. 30 and 31 below) attached to a top surface of the pledget 2702 that can be tensioned to help the pledget provide a force on a tissue member on which the pledget is attached. In alternative embodiments, the suture 2816 is attached to the pledgets at more than two locations. The suture 2816 can be attached to the pledgets 2702 by any manner that allows the pledgets to be attached to a tissue member and provide a force to the tissue member.

Referring to FIGS. 30 and 31, the valve repair device 2700 is configured to attach one or more pledgets 2702 to a tissue member 3001 (e.g., the annulus of the mitral valve, the leaflets of the mitral valve, etc.). The tissue member 3001 has a first side 3002 and a second side 3003. In the illustrated example, the device 2700 is penetrating the tissue member (from the first side 3002 to the second side 3003) in order to attach the pledgets 2702 to the second side 3003 of the tissue member 3001. Referring to FIG. 30, the device 2700 attached a first pledget 2702a (e.g., the starting pledget of the sequence) to the tissue member 3001 and is in the process of deploying a second pledget 2702b to attach to the tissue member 3001. The first pledget 2702a and the second pledget 2702b are coupled by a suture 2816.

Still referring to FIG. 30, to attach the first pledget 2702a, the device 2700 penetrated the tissue member (e.g., using the puncturing member 2704 shown in FIG. 27) and deployed the first pledget 2702a out of the outlet 2703 of the delivery member 2701 and attaches to the second side 3003 of the tissue member 3001 by a connection member 3024. The connection member 3024 can be, for example, a stitch or a knot, or a fastener. The suture member 2816 extends from the connection member 3024, through the pledget 2702a, above the pledget, and through a second location on the pledget, such that a tensioning portion 3026 of the suture 2816 exists on a top surface of the pledget 2702a. After deployment of the first pledget 2702a, the device 2700 returned through the tissue member 3001 such that a return portion 3020 of the suture 2816 extends from the second side 3003 to the first side 3002 of the tissue member 3001. Subsequently, the device 2700 penetrates the tissue member 3001 to deploy the second pledget 2702b, and, during this penetration, a penetrating portion 3021 of the suture 2816 extends from the first side 3002 to the second side 3003 of the tissue member 3001. In between the return portion 3020 of the suture 2816 from a pledget 2702a-2702d and the penetrating portion 3021 of the suture 2816 of an adjacent subsequent pledget 2702a-2702d is a tightening portion 3022 of the suture 2816.

Referring to FIG. 31, the device 2700 was used to complete the sequence of attaching four pledgets 2702a-2702d to the tissue member 3001, and the four pledgets are attached by suture 2816. The sequence of pledgets starts with the first pledget 2702a and ends with the fourth pledget 2702d. The first pledget 2702a is attached to the second side 3003 of the tissue member 3001 by the connection member 3024 and the return portion 3020 of the suture 2816. The second pledget 2702b, third pledget 2702c, and fourth pledget 2702d are attached to the second side 3003 of the tissue member 3001 by the corresponding penetrating portions 3021 and the return portions 3020 of the suture 2816. The suture 2816 extends past the fourth pledget 2702d, such that an excess suture 3118 exists at the end of the suture 2816. That is, after the return portion 3020 of the suture 2816 attaches the fourth pledget 2702d to the tissue member 3001, an excess suture 3118 extends below the first side 3002 of the tissue member 3001. In addition, a tensioning portion 3026 exists above each of the pledgets 2702a-2702d, and a tightening portion exists on the first side 3002 of the tissue member 3001 and in between each of the pledgets 2702a-2702d.

The pledgets 2702a-2702d are disposed on the suture 2816 such that the suture is fixed to the pledget 2702 and is slideably movable in relation to the pledgets 2702b-2702d. The movement of the suture 2816 in relation to the pledgets 2702a-2702d allows each of the pledgets to be attached to the tissue member 3001 at different distances from each other. For example, the distance D1 between the first pledget 2702a and the second pledget 2702b can be the same or different from the distance D2 between the second pledget 2702b and the third pledget 2702c. Similarly, the distance D3 between the third pledget 2702c and the fourth pledget 2702d can be the same or different from the distances D1 and/or D2.

The movability of the pledgets 2702a-2702d with respect to the suture 2816 also allows force F to be applied to the tissue member 3001 by the pledgets 2702a-2702d. The tensioning portion 3026 and the tightening portion 3022 of the suture 2816 is in a loosened state when the pledgets 2702a-2702d are initially attached to the tissue member 3001. When a pulling force is applied to the excess portion 3118 of the suture 1816, the tensioning portion 3026 and the tightening portion 3022 change from a loosened state to a taut state, which makes the amount of force F applied by the pledgets 2702a-2702d and the amount of force T applied by the suture 2816 larger. The force F applied by the pledgets 2702a-2702d and the force T applied by the suture 2816 create a cinching effect on the tissue member 3001.

While the above example shows a sequence having four pledgets to provide a cinching effect on the tissue member 3001, it should be understood that a sequence having any number of pledgets can be used to cinch a tissue member. For example, a sequence may include between 2 pledgets and 20 pledgets, such as, between 4 pledgets and 18 pledgets, such as between 6 pledgets and 16 pledgets, such as between 8 pledgets and 14 pledgets, such as between 10 pledgets and 12 pledgets, such as 11 pledgets. In an exemplary procedure, 14 pledgets can be used to cinch a tissue member 3001. In alternative examples, more than 20 pledgets can be used to cinch a tissue member 3001.

Referring to FIGS. 32 and 33A-33D, another exemplary procedure for mitral annuloplasty is shown using the exemplary valve repair device 2700 (FIGS. 27-31). The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 3308 in FIGS. 33A-33D), which could lead to regurgitation of blood through the mitral valve. The exemplary mitral annuloplasty procedure provides annular support to the mitral valve by reducing the size of the annulus, which allows the leaflets to properly coapt.

Figure 32:
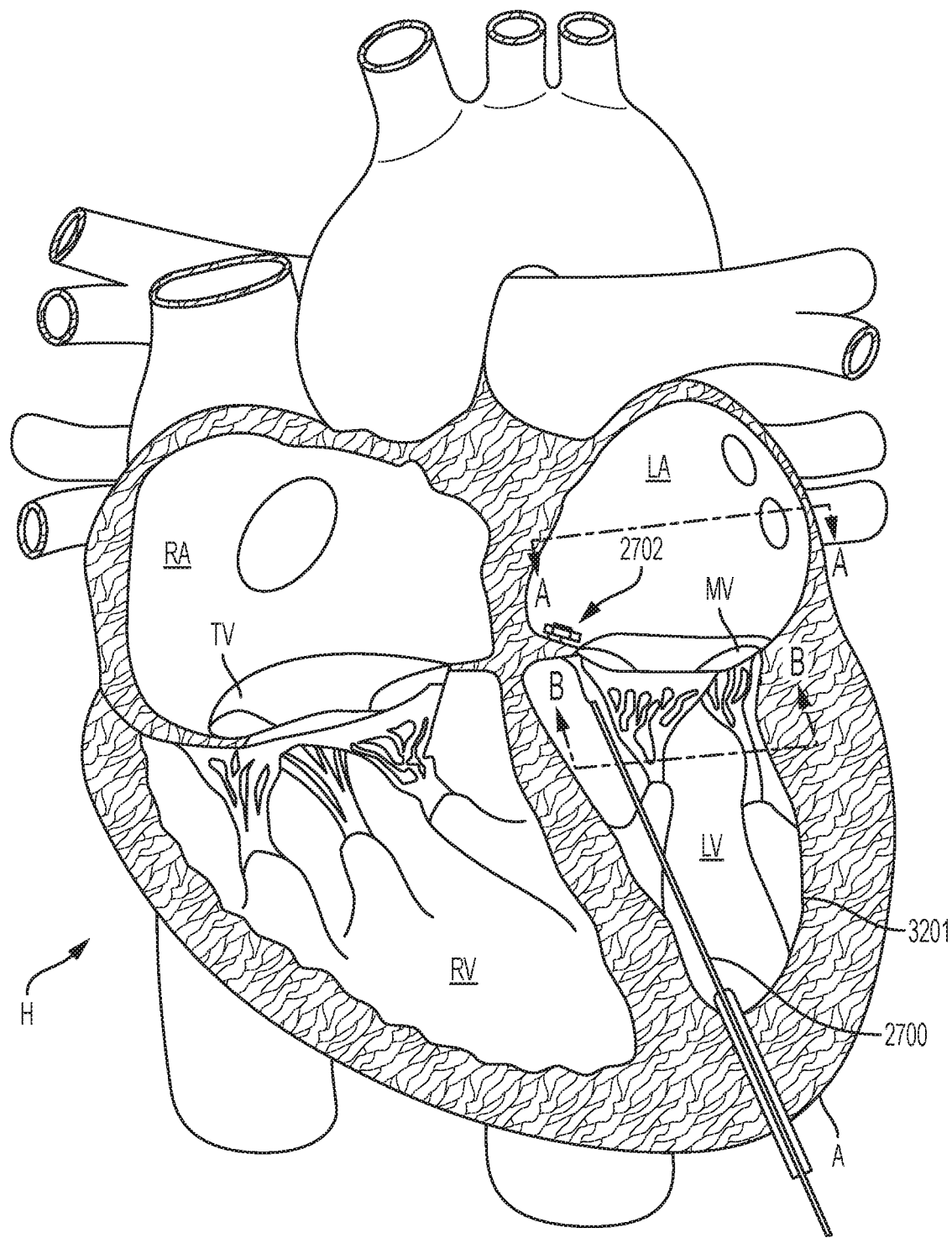
FIG. 32 is a cutaway view of the human heart showing the exemplary embodiment of the valve repair device of FIG. 27 engaging the mitral valve through the apex of the heart.

Referring to FIG. 32, the valve repair device 2700 enters the left ventricle LV through the apex A of the heart H. After the valve repair device 2700 enters the left ventricle LV, the repair device engages the mitral valve MV. The valve repair device 2700 is configured to attach a pledget 2702 to the mitral valve MV. That is, similar to the exemplary procedure shown in FIGS. 30 and 31, the valve repair device 2700 is configured to engage the annulus of the mitral valve MV from the left ventricle LV, penetrate the annulus, and attach a pledget 2702 to the annulus in the left atrium LA. The valve repair device 2700 may take any suitable form that is capable of entering the left ventricle LV through the apex A of the heart H and attaching a pledget 2702 to the mitral valve. For example, in addition to the features of the valve repair device 2700 described with reference to FIGS. 27-31, the valve repair device 2700 may include the features of the devices described in U.S. Pat. No. 7,635,386 and U.S. Patent Application Publication No. 2014/0114404 A1, which are hereby incorporated by reference in their entireties. The pledget 2702 may take any suitable form that is capable of being deployed against heart tissue, such as the annulus of a heart valve, and providing support for a suture that extends through the heart valve tissue, such as, for example, any form described in the present application. While the pledgets 2702 are illustrated as being deployed on only one side of the heart tissue, in other embodiments, pledgets can be provided on both sides of the heart tissue to provide reinforcement for the suture 2816 on both sides of the tissue.

Figure 33A:
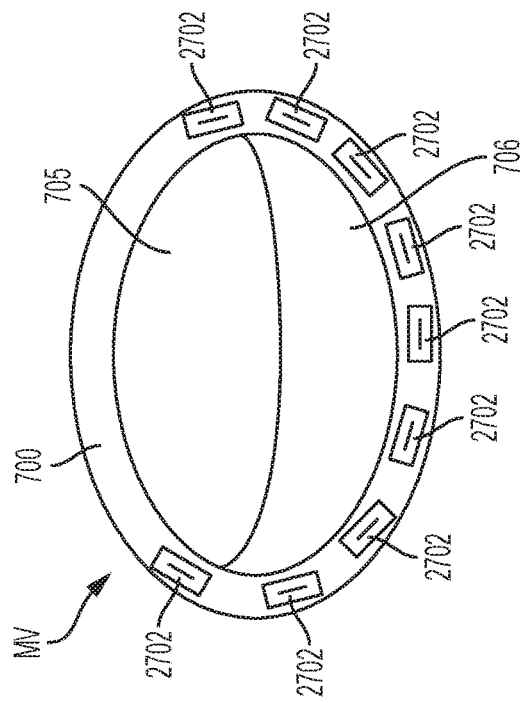
FIGS. 33A and 33C illustrate the mitral valve shown from the direction represented by line A-A FIG. 32 during an exemplary process for repairing a first portion of the mitral valve using the exemplary valve repair device of FIG. 32.
Figure 33C:
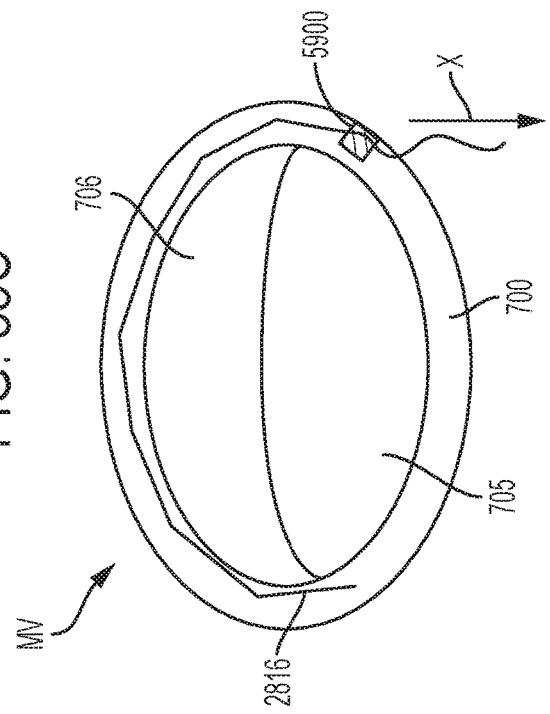

The exemplary mitral annuloplasty procedure includes attaching two or more pledgets 2702 to the annulus 700, in which the two or more pledgets are connected by a suture 2816. In addition, the exemplary procedure includes tensioning the suture 2816 (and, as a result, the two or more pledgets 2702) to reduce the size of the annulus, and, subsequently, fixing the suture once a desired reduction of the size of the annulus is achieved. The suture 2816 can be made of an ePTFE suture, a braid of suture, or any other suitable material. FIGS. 33A and 33C illustrate the mitral valve MV from the perspective of line A-A shown in FIG. 32 (e.g., illustrating the mitral valve MV from the left atrium LA), and FIGS. 33B and 33D illustrate the mitral valve MV from the perspective of line B-B shown in FIG. 32 (e.g., illustrating the mitral valve MV from the left ventricle LV).

Figure 33B:
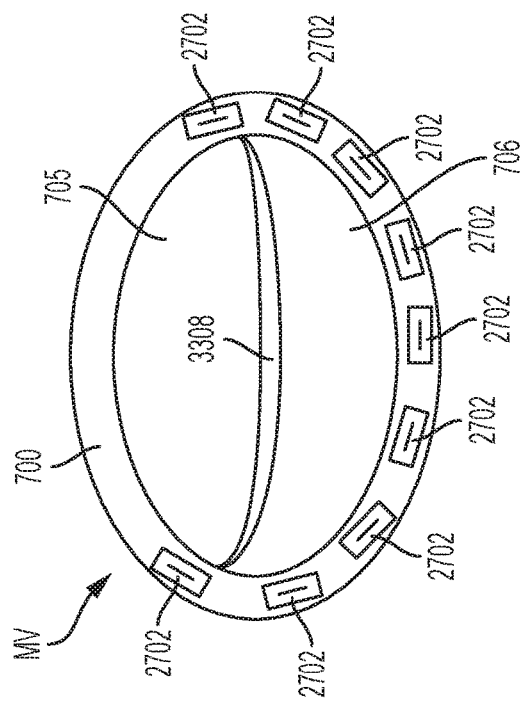
FIGS. 33B and 33D illustrate the mitral valve shown from the direction represented by line B-B FIG. 32 during an exemplary process for repairing a first portion of the mitral valve using the exemplary valve repair device of Figure.

Referring to FIGS. 33A and 33B, in a first step of the exemplary mitral annuloplasty procedure, the valve device 2700 attaches the two or more pledgets 2702 to the annulus 700. In the illustrated embodiment, the device 2700 attaches nine pledgets 2702 to the annulus 700. In alternative embodiments, between 2 pledgets and 20 pledgets can be attached to the annulus 700, such as between 4 pledgets and 18 pledgets, such as between 6 pledgets and 16 pledgets, such as between 8 pledgets and 14 pledgets, such as between 10 pledgets and 12 pledgets, such as 11 pledgets. In certain embodiments, the device 2700 can attach more than 20 pledgets to the annulus. In an exemplary procedure, the device 2700 attaches twelve pledgets 2702 to the annulus 700. Referring to FIG. 33A, each of the pledgets 2702 are attached to the annulus 700 in the left atrium LA. Referring to FIG. 33B, each of the pledgets 2702 are attached to the annulus 700 by a suture 2816, such that providing a pulling force to the excess portion 3118 of the suture 2816 will cause the pledgets 2702 to reduce the size of the annulus 700.

Figure 33D:
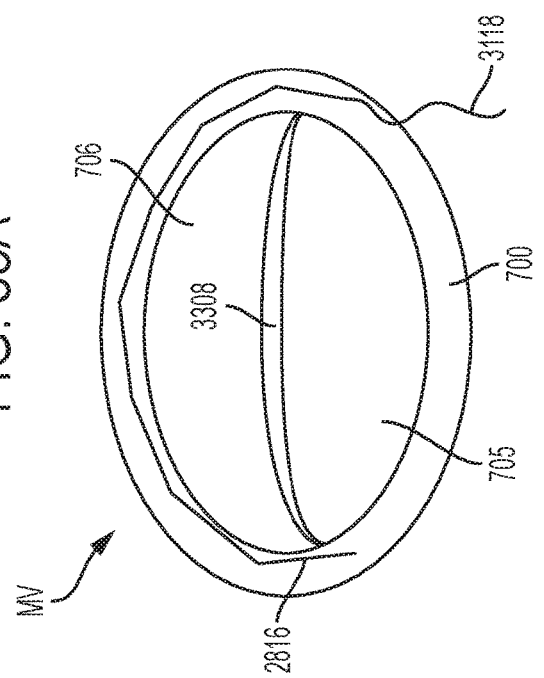

Referring to FIGS. 33C and 33D, in a second step of the exemplary mitral annuloplasty procedure, a force is applied to the excess portion 3118 of the suture 2816 in the direction X (FIG. 33D) to create a cinching effect on the annulus 700. The force applied to the suture 2816 causes a reduction in size of the annulus 700, which causes the anterior leaflet 705 and the posterior leaflet 706 to coapt (e.g., the force causes the gap 3308 to close, as shown in FIGS. 33C and 33D). Once the anterior leaflet 705 and the posterior leaflet 706 properly coapt, the suture 2816 is fixed such that the size of the annulus remains in the reduced state. In one example, the suture 2816 can be fixed to an interior wall 3201 (FIG. 32) of the left ventricle LV. For example, the suture 2816 can be fixed on an interior wall 3201 near the location of insertion by the valve repair device 2700 (or other tensioning device) through the apex A so that suture 2816 is conveniently accessible by the valve repair device (or other tensioning device) if the amount of force applied on the suture 2816 needs to be altered to reduce or expand the size of the annulus. In alternative examples, the suture 2816 can be fixed on any other location of the interior wall 3201 of the left ventricle LV that is accessible by the valve repair device 2700 (or other tensioning device), or the suture may be fixed by an anchor 5900 that is seated against the valve annulus on the ventricular side, opposite the last pledget 2702 in the series.

Adjacent pledgets 2702 can be placed any distance apart from each other that allows the pledgets 2702 to be tensioned to repair at least a portion of the mitral valve MV. In certain exemplary procedures, the adjacent pledgets 2702 may be positioned at different distances apart from each other as compared to other adjacent pledgets. In certain embodiments, the pledgets 2702 are placed between one trigone (not shown) and another trigone.

The removal of the gap 3308 between the anterior leaflet 705 and the posterior leaflet 706 prevents regurgitation of blood from the left ventricle LV to the left atrium LA through the mitral valve MV. The suture 2816 can be tensioned and fixed by the valve repair device 2700 or a separate tensioning device (not shown). If a separate tensioning device is used, the tensioning device enters the left ventricle LV through the apex A of the heart H to engage the suture 2816.

Referring to FIGS. 34 and 35A-35D, another exemplary procedure for mitral annuloplasty is shown using the exemplary valve repair device 3400. The valve repair device 3400 has the same features as the valve repair device 2700 (FIGS. 27-31), except that it is configured to enter the left atrium LA through the atrial septum of the heart H. For example, in addition to the features of the valve repair device 2700, the valve repair device 3400 may include the features of the devices described in U.S. Pat. No. 7,635,386 and U.S. Patent Application Publication No. 2014/0114404 A1, which are hereby incorporated by reference in their entireties. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 3508 in FIGS. 35A-35D), which could lead to regurgitation of blood through the mitral valve. The exemplary mitral annuloplasty procedure provides annular support to the mitral valve by reducing the size of the annulus, which allows the leaflets to properly coapt.

Figure 34:
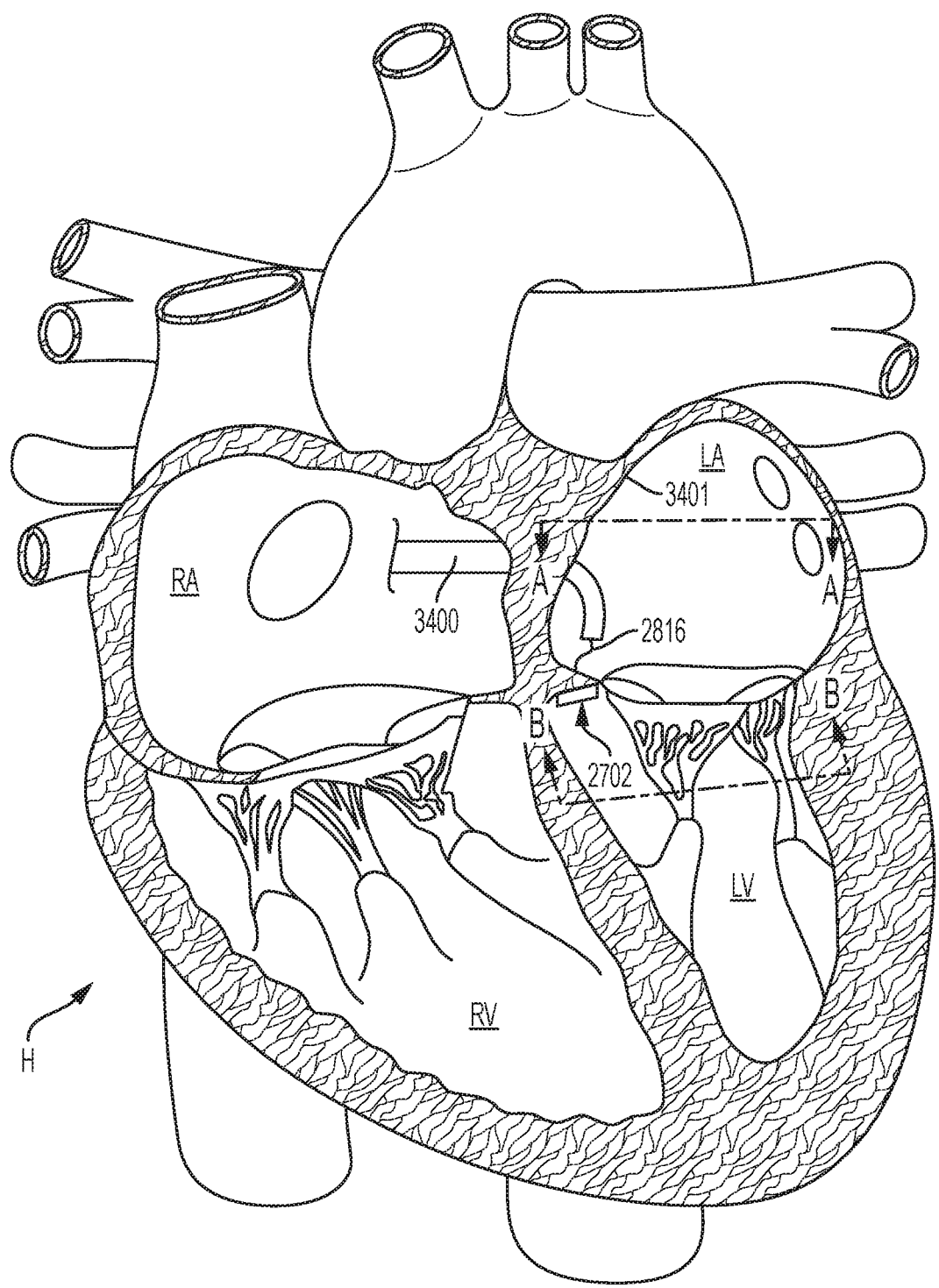
FIG. 34 is a cutaway view of the human heart showing an exemplary embodiment of a valve repair device engaging the mitral valve through the atrial septum of the heart.

Referring to FIG. 34, the valve repair device 3400 enters the left atrium LA through the atrial septum of the heart H. After the valve repair device 3400 enters the left atrium LA, the repair device 3400 engages the mitral valve MV. The valve repair device 3400 is configured to attach a pledget 2702 to the mitral valve MV. That is, similar to the exemplary procedure shown in FIGS. 30 and 31, the valve repair device 3400 is configured to engage the annulus of the mitral valve MV from the left atrium LA, penetrate the annulus, and attach a pledget 2702 to the annulus in the left ventricle LV. The pledget 2702 may take any suitable form that is capable of providing annular support to the mitral valve, such as, for example, any form described in the present application.

Figure 35C:
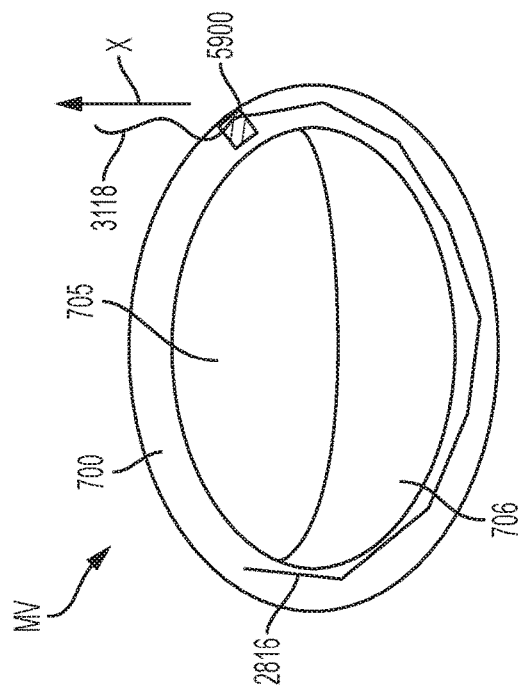
FIGS. 35A and 35C illustrate the mitral valve shown from the direction represented by line A-A FIG. 34 during an exemplary process for repairing a first portion of the mitral valve using the exemplary valve repair device of FIG. 34.

The exemplary mitral annuloplasty procedure includes attaching two or more pledgets 2702 to the annulus 700, in which the two or more pledgets are connected by a suture 2816. In addition, the exemplary procedure includes tensioning the suture 2816 (and, as a result, the two or more pledgets 2702) to reduce the size of the annulus, and, subsequently, fixing the suture once a desired reduction of the size of the annulus is achieved. The suture 2816 can be made of an ePTFE suture, a braid of suture, or any other suitable material. FIGS. 35A and 35C illustrate the mitral valve MV from the perspective of line A-A shown in FIG. 34 (e.g., illustrating the mitral valve MV from the left atrium LA), and FIGS. 35B and 35D illustrate the mitral valve MV from the perspective of line B-B shown in FIG. 34 (e.g., illustrating the mitral valve MV from the left ventricle LV).

Figure 35D:
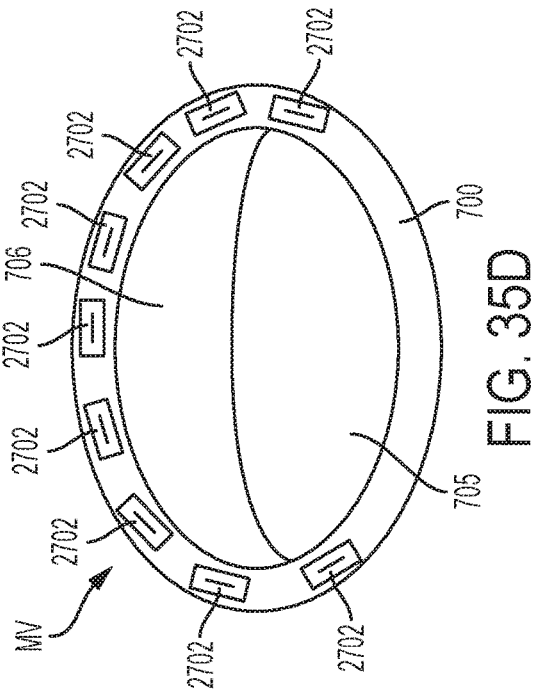
FIGS. 35B and 35D illustrate the mitral valve shown from the direction represented by line B-B FIG. 34 during an exemplary process for repairing a first portion of the mitral valve using the exemplary valve repair device of FIG. 34.
Figure 35A:
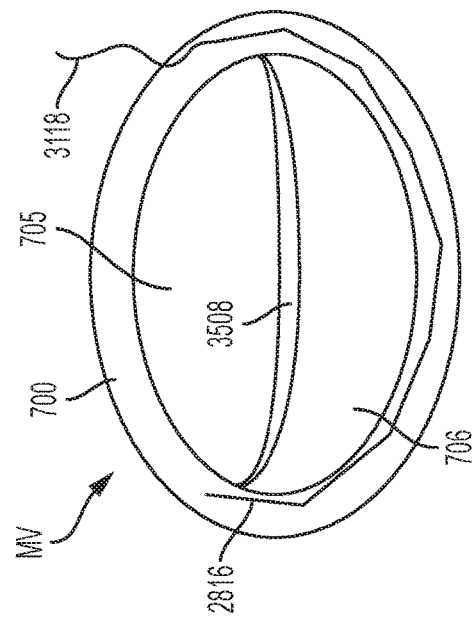
Figure 35B:
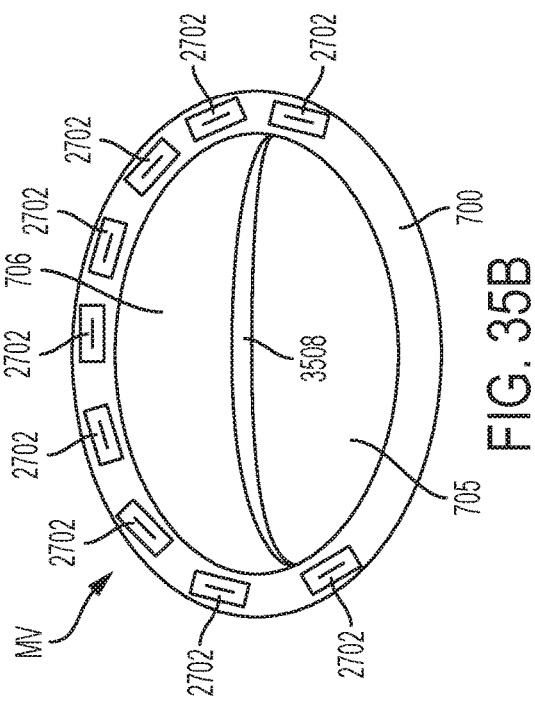

Referring to FIGS. 35A and 35B, in a first step of the exemplary mitral annuloplasty procedure, the valve device 3400 attaches the two or more pledgets 2702 to the annulus 700. In the illustrated embodiment, the device 3400 attaches nine pledgets 2702 to the annulus 700. In alternative embodiments, between 2 pledgets and 20 pledgets can be attached to the annulus 700, such as between 4 pledgets and 18 pledgets, such as between 6 pledgets and 16 pledgets, such as between 8 pledgets and 14 pledgets, such as between 10 pledgets and 12 pledgets, such as 11 pledgets. In certain embodiments, the device 3400 can attach more than 20 pledgets to the annulus. In an exemplary procedure, the device 3400 attaches twelve pledgets 2702 to the annulus 700. Referring to FIG. 35B, each of the pledgets 2702 are attached to the annulus 700 in the left atrium LA. Referring to FIG. 35A, each of the pledgets 2702 are attached to the annulus 700 by a suture 2816, such that providing a pulling force to the excess portion 3118 of the suture 2816 will cause the pledgets 2702 to reduce the size of the annulus 700.

Referring to FIGS. 35C and 35D, in a second step of the exemplary mitral annuloplasty procedure, a force is applied to the excess portion 3118 of the suture 2816 in the direction X (FIG. 35C) to create a cinching effect on the annulus 700. The force applied to the suture 2816 causes a reduction in size of the annulus 700, which causes the anterior leaflet 705 and the posterior leaflet 706 to coapt (e.g., the force causes the gap 3508 to close, as shown in FIGS. 35C and 35D). Once the anterior leaflet 705 and the posterior leaflet 706 properly coapt, the suture 2816 is fixed such that the size of the annulus remains in the reduced state. In one example, the suture 2816 can be fixed to an interior wall 3401 (FIG. 34) of the left atrium LA. For example, the suture 2816 can be fixed on an interior wall 3401 near the location of insertion by the valve repair device 3400 (or other tensioning device) through the atrial septum so that suture 2816 is conveniently accessible by the valve repair device (or other tensioning device) if the amount of force applied on the suture 2816 needs to be altered to reduce or expand the size of the annulus. In alternative examples, the suture 2816 can be fixed on any other location of the interior wall 3401 of the left atrium LA that is accessible by the valve repair device 3400 (or other tensioning device), or the suture may be fixed by an anchor 5900 that is seated against the valve annulus on the atrial side, opposite the last pledget 2702 in the series.

Adjacent pledgets 2702 can be placed any distance apart from each other that allows the pledgets 2702 to be tensioned to repair at least a portion of the mitral valve MV. In certain exemplary procedures, the adjacent pledgets 2702 may be positioned at different distances apart from each other as compared to other adjacent pledgets. In certain embodiments, the pledgets 2702 are placed between one trigone (not shown) and another trigone.

The removal of the gap 3508 between the anterior leaflet 705 and the posterior leaflet 706 prevents regurgitation of blood from the left ventricle LV to the left atrium LA through the mitral valve MV. The suture 2816 can be tensioned and fixed by the valve repair device 3400 or a separate tensioning device (not shown). If a separate tensioning device is used, the tensioning device enters the left atrium LA through the atrial septum of the heart H to engage the suture 2816.

Referring to FIG. 16A, in certain embodiments, the exemplary procedure for mitral annuloplasty shown in FIGS. 34 and 35A-35D can be completed with a transatrial procedure using valve repair device 1600'. Referring to FIG. 16A, the valve repair device 1600' enters the left atrium LA through an outer wall of the heart H. After the valve repair device 1600' enters the left atrium LA, the repair device engages the mitral valve MV. The valve repair device 1600' is configured to attach one or more pledgets 2702 to the mitral valve MV. The valve repair device 1600' may take any suitable form that is capable of entering the left atrium LA through an outer wall of the heart H and attaching one or more pledgets to the mitral valve. For example, in addition to the features of the valve repair device 2700, the valve repair device 1600' can include the features of the devices described in U.S. Pat. No. 7,635,386 and U.S. Patent Application Publication No. 2014/0114404 A1, which are hereby incorporated by reference in their entireties. For example, the valve repair device 1600' can take the form of the devices described in U.S. Pat. No. 7,635,386 and U.S. Patent Application Publication No. 2014/0114404 A1, which are hereby incorporated by reference in their entireties.

While the example provided above (in FIGS. 33A-33D and 35A-35D) include using two or more pledgets 2702 connected by a suture 2816 to close the gap 3308, 3508 between the anterior leaflet 705 and the posterior leaflet 706, it should be understood that any number of pledgets connected by a suture can be used. In certain situations, only one sequence of pledgets connected by a suture can be required to close the gap 3308, 3508. In other situations, more than one sequence of pledgets connected by one or more sutures can be used to close the gap 3308, 3508. The pledgets can be attached to any location on the annulus 700 in order to cause the anterior leaflet 705 and the posterior leaflet 706 to properly coapt.

While the valve repair devices 2700, 3400, 1600' and the exemplary annuloplasty procedures provided above are described with reference to repairing the mitral valve MV, it should be understood that the valve repair devices and the concepts used in the exemplary mitral annuloplasty procedures can be used to repair any native valve. For example, the valve repair devices 2700, 3400, 1600' and the concepts of the exemplary annuloplasty procedures described above can be used to repair the aortic valve AV, the tricuspid valve TV, and the pulmonary valve PV.

Figure 36:
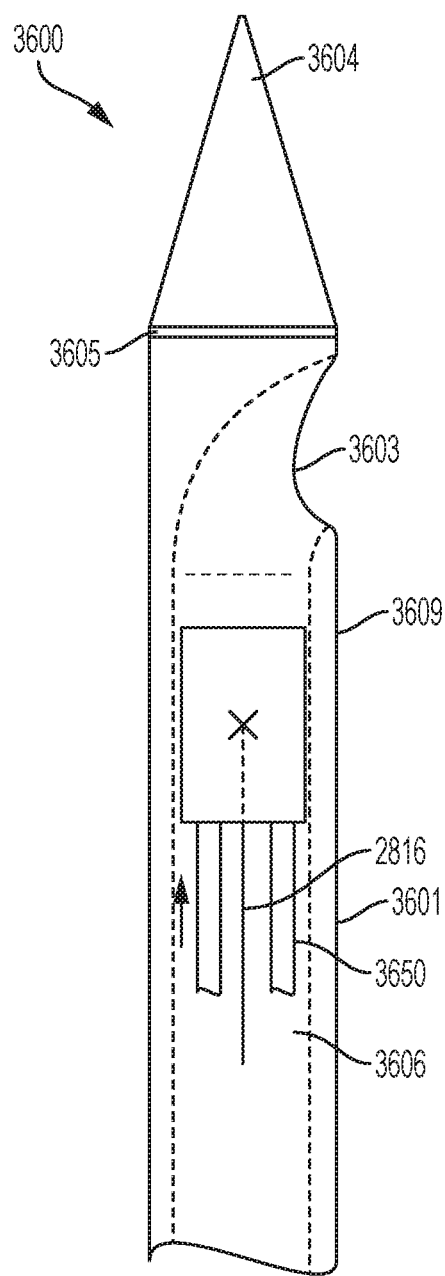
FIG. 36 is another exemplary embodiment of a valve repair device.

Referring to FIG. 36, another exemplary valve repair device 3600 for repairing the mitral valve includes a delivery member 3601 and an advancement member 3650. The advancement member 3650 is disposed in the delivery member 3601 with one or more pledgets 2702. The advancement member 3650 is configured to push 3650 one or more pledgets 2702 through an outlet 3603 of the delivery member 3601. An optional puncturing member 3604 is attached to the end 3605 of the delivery member 3601 of the valve repair device 3600. The puncturing member 3604 is configured to puncture a tissue member (e.g., the annulus of the mitral valve, the leaflets of the mitral valve, etc.). The puncturing member 3604 can be, for example, a solid tapered tip, a needle, or the like. The outlet 3603 is located proximal to the puncturing member 3604 and in a side surface 3609 of the delivery member 3601. It is advantageous to have a valve repair device 3600 with a puncturing member 3604 that is separated from the outlet 3603 of the delivery member 3601 because the puncturing member 3604 can be configured to more accurately puncture a tissue member.

The valve repair device 3600 is configured to deploy one or more pledgets 2702 (by the advancement member) out of the outlet 3603 of the delivery member 3601 and attach the pledgets to a tissue member. In the illustrated embodiment, the pledgets 2702 (FIGS. 38E and 38F) are attached to each other by a suture 2816 (FIGS. 38E and 38F). The pledgets 2702 can be configured to be crimped and compressed to occupy less space in the shaft 3606 of the of the delivery member 3601. Upon being deployed through the outlet 3603 of the delivery member 3601, the pledgets 2702 are optionally configured to expand or return to an unconstrained shape.

Figure 37B:
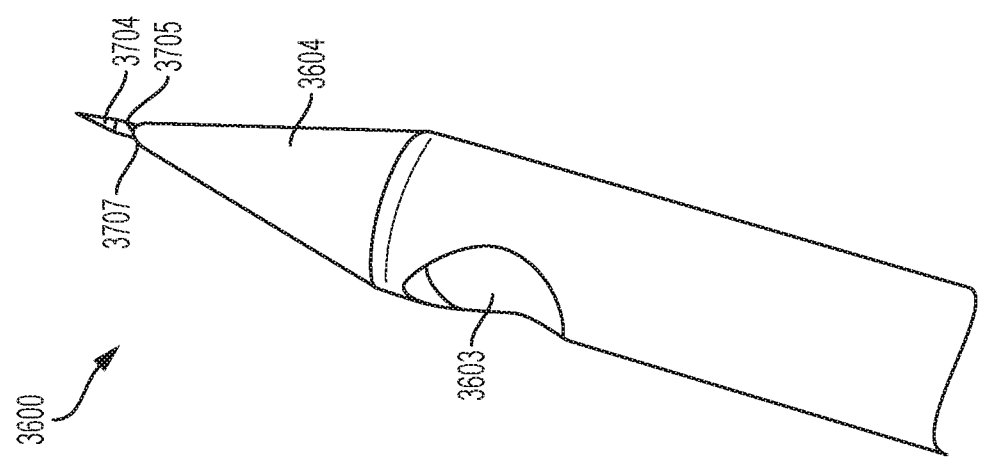
FIGS. 37A-37B illustrate another exemplary embodiment of a valve repair device.
Figure 37A:
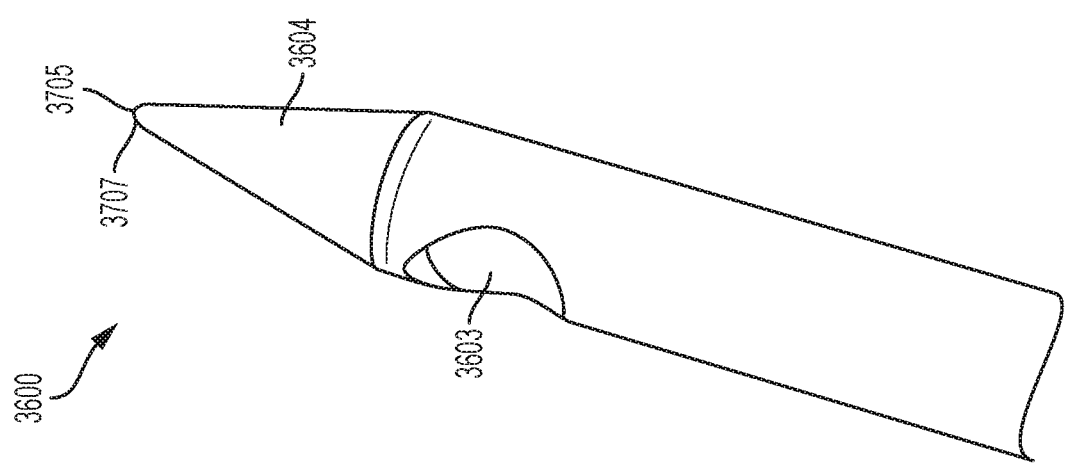

Referring to FIGS. 37A and 37B, in certain embodiments, the puncturing member 3604 of the valve repair device 3600 includes an extendable and retractable blade or a sharp point 3704. Referring to FIG. 37A, the puncturing member 3604 may include an opening 3705, and the blade or sharp point 3704 may be housed in the puncturing member 3604 and configured to exit the opening 3705 of the puncturing member 3604 as desired. Referring to FIG. 38A, the device 3600 can be controlled such that, when desired, the blade or sharp point 3704 is extended through the opening 3705. For example, the blade or sharp point 3704 is spring-loaded and extended by releasing the spring. The tip 3707 of the puncturing member 3604 can be blunt when the blade is in a disengaged state (as shown in FIG. 37A).

FIGS. 38A-38F illustrate the exemplary valve repair device 3600 with the retractable blade or sharp point 3704 attaching a pledget 2702 to a tissue member 3801 (e.g., the annulus of the mitral valve, the leaflets of the mitral valve, etc.). In one exemplary embodiment, the valve repair device includes a device for holding the tissue as the sharp point 3704 is extended. For example, a suction device can be used. One such suction device is disclosed in U.S. Provisional Application No. 62/326,609. FIG. 38A illustrates the device 3600 prior to engaging the tissue member 3801. FIG. 38B illustrates the device engaging a first side 3802 of the tissue member 3801. The tip 3707 (FIGS. 37A and 37B) of the puncturing member 3604 is the first member of the device 3600 to engage the tissue member 3801. If the tip 3707 of the puncturing member 3604 is blunt, the tip 3707 can be moved around while engaging the tissue member 3801 without causing trauma the tissue member 3801, which allows for the proper location for puncturing the tissue member 3801 to be found without puncturing the tissue member in an undesired location. Referring to FIG. 38C, once the proper location for puncturing the tissue member is found, the blade or sharp point 3704 can be ejected from the puncturing member 3604 to puncture the tissue member. Referring to FIG. 38D, after the tissue member 3801 is punctured by the blade or sharp point 3704, the device 3600 is moved through the tissue member such that the opening 3603 of the device moves from the first side 3802 of the tissue member to the second side 3803 of the tissue member. Any time after puncturing the tissue member 3801, the blade or sharp point 3704 may be retracted through the opening 3705 (FIGS. 37A and 37B) of the puncturing member 3604. Referring to FIG. 38E, when the opening 3603 is on the second side 3803 of the tissue member 3801, the device 3600 deploys a pledget 2702 attached to a suture 2816. Referring to FIG. 38F, after deploying the pledget 2702, the device 3600 is moved from the second side 3803 of the tissue member 3801 back to the first side 3802 of the tissue member such that a return portion 3820 of the suture 2816 extends from the pledget 2702 on the second side 3803 of the tissue member 3801, through the tissue member 3801, and extends past the first side 3802 of the tissue member 3801. After the device 3600 is moved back through the tissue member 3801, the pledget 2702 is attached to the second side 3803 of the tissue member 3801.

While FIGS. 38A-38F show the device 3600 attaching a single pledget 2702 to a tissue member 3801, it should be understood that the device 3600 can be used in the procedures shown in FIGS. 30 through 35A-35D. In addition, the features of device 3600 (FIGS. 36 through 38A-38F) and device 2700 (FIG. 27 through FIGS. 35A-35D) can be used in any other procedure disclosed in the present application.

Figure 39:
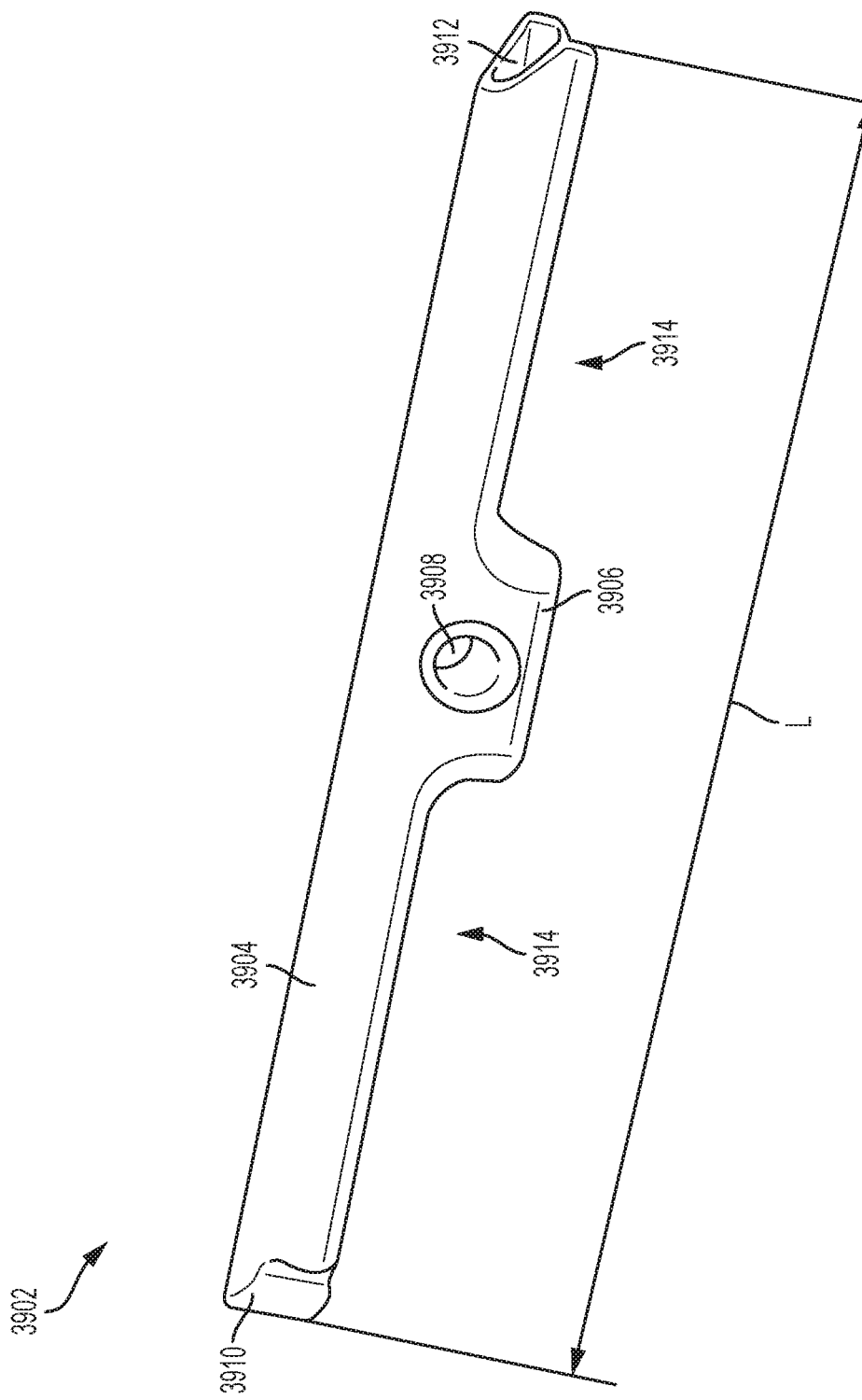
FIG. 39 illustrates another exemplary embodiment of an attachment member.

Referring to FIG. 39, another exemplary embodiment of an attachment member 3902 that may be used to repair the mitral valve includes a main body portion 3904, a tab portion 3906, and an aperture 3908. The attachment member 3902 is configured to be deployed by a valve repair device 4000 (e.g., the valve repair device 4000 shown in FIGS. 40A and 40B, the valve repair device 4300 shown in FIG. 43, etc.) and attached to a tissue member (e.g., the annulus of the mitral valve, the leaflets of the mitral valve, etc.) in order to apply a force to the tissue member. The main body 3904 is configured to engage the tissue member when the attachment member 3902 is attached to the tissue member. In certain embodiments, the main body 3904 has a round cross section. In these embodiments, the diameter of the main body can be, for example, between about 0.5 mm and about 2.5 mm, such as between about 0.75 mm and about 2 mm, such as between about 1 mm and about 2 mm, such as about 1.5 mm. In an exemplary embodiment, the diameter of the main body is about 1.1 mm. In some other embodiments, the main body 3904 has a flat surface, and the attachment member 3902 is configured such that the flat surface engages the tissue member when the attachment member is attached to the tissue member. The main body 3904 of the attachment member 3902 may have any suitable length L. For example, the length L can be between about 4 mm and about 10 mm, such as between about 5 mm and about 9 mm, such as between about 6 mm and about 8 mm, such as about 7 mm. In one embodiment, the length L is about 7.6 mm. The tab portion 3906 is configured such that, when the attachment member 3902 is attached to a tissue member, the attachment member 3902 provides a substantially even load distribution. The aperture 3908 is configured to attach the attachment member 3902 to a suture (e.g., the suture 4016 shown in FIGS. 40A and 40B). The attachment members 3902 can be made of, for example, implantable polymers such as PET, PTFE, etc. In additional embodiments, the attachment members 3902 can be made from implantable metals, implantable ceramics, or other suitable implant-grade materials.

Referring to FIGS. 40A and 40B, another exemplary embodiment of a valve repair device 4000 for repairing the mitral valve includes a delivery member 4001 and an advancement member 4002. The advancement member 4002 is configured to move one or more attachment members 3902, such that the attachment members can be deployed through an outlet 4003 of the delivery member 4001. The delivery member 4001 of the valve repair device 4000 includes a puncturing member 4004 that is configured to puncture a tissue member (e.g., the annulus of the mitral valve, the leaflets of the mitral valve, etc.). The delivery member 4001 can be a hollow needle, any of the puncturing devices disclosed herein, or any other suitable device. The attachment members 3902 are attached to each other by a suture 4016.

Referring to FIGS. 39 and 40A-40B, in certain embodiments, the attachment members 3902 include a tongue portion 3910 and a groove portion 3912. The tongue portion 3910 and groove portion 3912 are configured such that the tongue portion 3910 of one attachment member engages the groove portion 3912 of an adjacent attachment member. For example, as shown in FIGS. 40A and 40B, when the attachment members 3902 are stacked within the repair device 4000, the attachment members engage adjacent attachment members. During this engagement, the tongue portions 3910 of the attachment members 3902 engage the groove member 3912 of adjacent attachment members.

Still referring to FIGS. 39 and 40A-40B, in certain embodiments, the attachment members 3902 have recesses 3914 located on each end of the tab portion 3906. The recesses 3914 are configured to provide space for the suture 4016 when the attachment members 3902 and the suture 4016 are in the repair device 4000. For example, referring to FIGS. 40A and 40B, the recesses 3914 of adjacent attachment members 3902 are aligned such that an open space 4020 exists between the tab portions 3906 of adjacent attachment members 3902, and the suture 4016 is disposed in this open space prior to being deployed by the device 4000.

Referring to FIGS. 40A and 40B, the advancement member 4002 is configured to engage and move one or more attachment members 3902 through the outlet 4003 of the delivery member 4001. In the illustrated embodiment, the advancement member 4002 is a pusher that engages the last attachment member 3902 in a sequence of stacked attachment members in order to push the attachment members 3902 out of the outlet 4003. Referring to FIG. 40A, the illustrated sequence of attachment members 3902 includes four attachment members, and each of the four attachment members remain in the delivery portion 4001 of the device 4000 (e.g., none of the attachment members have been moved out of the outlet 4003). Referring to FIG. 40B, one of the attachment members 3902 has been pushed out of the outlet 4003. That is, a force is created by the advancement member 4002 in the X direction, which causes an attachment member 3902 to move out of the outlet 4003 of the device 4000. As shown in the illustrated embodiment, the advancement member 4002 can be configured to engage with the attachment members 3902. For example, the advancement member has an engagement surface 4022 and an extended portion 4024. The engagement surface 4022 engages the main body 3904 (FIG. 39) of the attachment member 3902, and the extended portion fits into the recess 3914 (FIG. 39) of the attachment member 3902. While, in the illustrated embodiment, the advancement member 4002 is shown as being a pusher, it should be understood that the advancement member 4002 can take any suitable form that is capable of moving the attachment members 3902 through the delivery member 4001 and out of the outlet 4003.

Still referring to FIGS. 40A and 40B, the device 4000 can be configured such that there is an interference between the attachment members 3902 and the delivery member 4001 that prevents the attachment members from pre-deploying. That is, the device 4000 can be configured such that the attachment members 3902 are prevented from exiting the outlet 4003 unless an additional force (such as a force provided by the advancement member 4002) causes the attachment members 3902 to exit the outlet 4003. In the illustrated embodiment, the device 4000 includes a protruding member 4026 that engages the attachment members 3902 prior to deployment. The force applied by the advancement member 4002 to the attachment members 3902 is sufficient to move the attachment members 3902 past the protruding member 4026 and out of the outlet 4003 of the device 4000.

In certain embodiments, the device 4000 is configured to deploy the attachment members 3902 such that the attachment members rotate upon being deployed. For example, the delivery portion 4001 of the device 4000 may have an arched (or declining) surface 4028 that causes the attachment members 3902 to move in alignment with the arched surface 4028. The arched surface 4028 can extend to the outlet 4003 of the device 4000. Referring to FIGS. 40A and 40B, as an attachment member 3902 is being moved to the outlet 4003 of the device 4000, a first end 4030 of the main body portion 3904 (FIG. 39) of the attachment member 3902 engages the arched surface 4028, which causes a first end 4030 of the attachment member to move in alignment with the arched surface 4028. As the attachment member 3902 continues to move toward the outlet 4003, the tab portion 3906 engages the protruding member 4026, which causes the attachment member 3902 to rotate as it exits the outlet 4003. The arched surface 4028 of the device 4000 is configured to allow for the attachment member 3902 to exit the outlet 4003 upon being moved by the advancement member 4002. In certain embodiments, the arched surface 4028 acts as a spring door such that, when the advancement member 4002 moves an attachment member 3902 to engage the arches surface 4028, the arched surface 4028 deflects to an open position to allow the attachment member 4002 to exit the outlet 4003. The arched surface 4028 moves in a direction Y between its original position to the open position.

The device 4000 can be configured such that the puncturing member 4004 is retractable. That is, the puncturing member 4004 is housed in the device 4000 such that it is not capable of puncturing a tissue member until the puncturing member 4004 is moved into an engageable position (as shown in FIGS. 40A and 40B). For example, referring to FIGS. 40A and 40B, the device 4000 has a housing 4032, and the puncturing member 4004 is movable in the directions D so that the puncturing member 4004 can be moved in and out of the housing 4032. When the puncturing member 4004 is in the housing 4032, the device 4000 can be moved, for example, through a patient's heart without causing trauma to any tissue member within the patient's heart. Once the device 4000 is located in a position to puncture a tissue member, the puncturing member 4004 can be moved out of the housing 4032 to engage the tissue member.

Referring to FIGS. 41 and 42A-42D, another exemplary procedure for mitral annuloplasty is shown using the exemplary valve repair device 4000 (FIGS. 40A and 40B). The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 4208 in FIGS. 42A-42D), which could lead to regurgitation of blood through the mitral valve. The exemplary mitral annuloplasty procedure provides annular support to the mitral valve by reducing the size of the annulus, which allows the leaflets to properly coapt.

Figure 41:
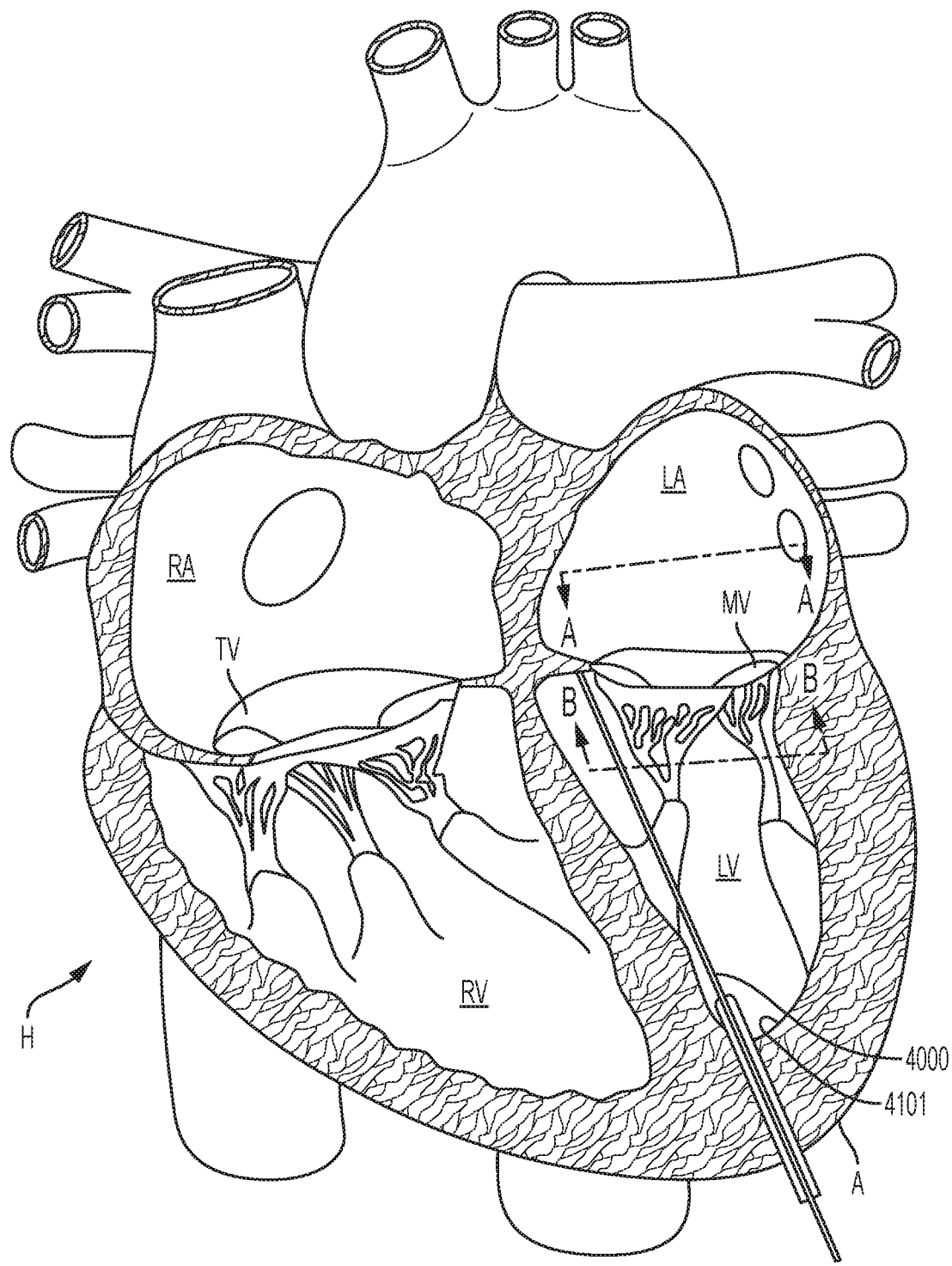
FIG. 41 is a cutaway view of the human heart showing the exemplary embodiment of the valve repair device of FIGS. 40A-40B engaging the annulus of the mitral valve through the apex of the heart.

Referring to FIG. 41, the valve repair device 4000 enters the left ventricle LV through the apex A of the heart H. After the valve repair device 4000 enters the left ventricle LV, the repair device engages the mitral valve MV. The valve repair device 4000 is configured to attach one or more attachment members 3902 to the mitral valve MV (as shown in FIGS. 42A-42D). That is, similar to the exemplary procedure shown in FIGS. 30 and 31, the valve repair device 4000 is configured to engage the annulus of the mitral valve MV from the left ventricle LV, penetrate the annulus, and attach an attachment member 3902 to the annulus in the left atrium LA. The valve repair device 4000 may take any suitable form that is capable of entering the left ventricle LV through the apex A of the heart H and attaching an attachment member 3902 to the mitral valve. For example, in addition to the features of the valve repair device 4000 described with reference to FIGS. 40A and 40B, the valve repair device 4000 may include the features of the devices described in U.S. Pat. No. 7,635,386 and U.S. Patent Application Publication No. 2014/0114404 A1, which are hereby incorporated by reference in their entireties. The attachment member 3902 may take any suitable form that is capable of providing annular support to the mitral valve, such as, for example, any form described in the present application.

Figure 42A:
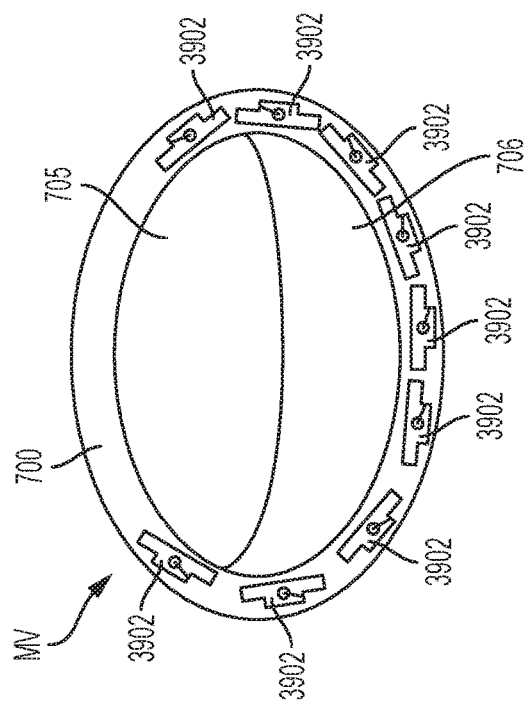
FIGS. 42A and 42C illustrate the mitral valve shown from either the perspective shown by line A-A FIG. 41 during an exemplary process for repairing the mitral valve using the exemplary valve repair device of FIGS. 40A-40B and the exemplary attachment member of FIG. 39.

The exemplary mitral annuloplasty procedure includes attaching two or more attachment members 3902 to the annulus 700, in which the two or more attachment members 3902 are linked by a suture 4016. The attachment members 3902 can be linked in a wide variety of different ways. For example, the attachment members 3902 can be inked in any of the ways the attachment members 2502 and 2702 can be linked, as described above. In addition, the exemplary procedure includes tensioning the suture 4016 (and, as a result, the two or more attachment members 3902) to reduce the size of the annulus, and, subsequently, fixing the suture once a desired reduction of the size of the annulus is achieved. The suture 4016 can be made of an ePTFE suture, a braid of suture, or any other suitable material. FIGS. 42A and 42C illustrate the mitral valve MV from the perspective of line A-A shown in FIG. 41 (e.g., illustrating the mitral valve MV from the left atrium LA), and FIGS. 42B and 42D illustrate the mitral valve MV from the perspective of line B-B shown in FIG. 41 (e.g., illustrating the mitral valve MV from the left ventricle LV).

Figure 42B:
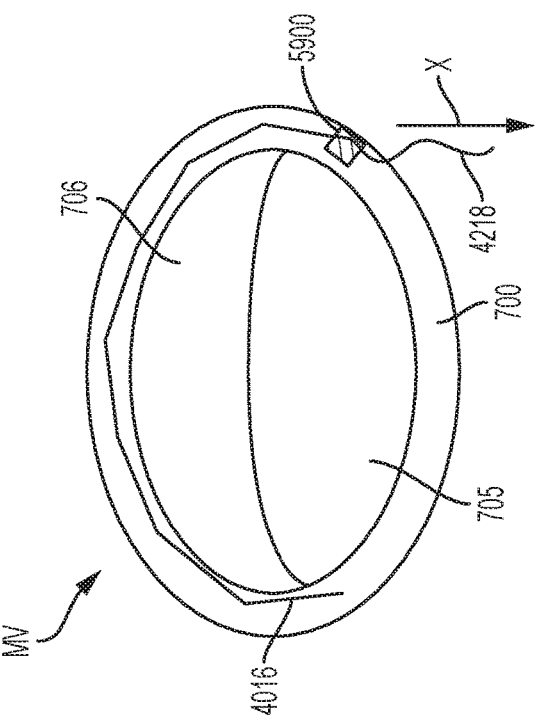
FIGS. 42B and 42D illustrate the mitral valve shown from either the perspective shown by line B-B FIG. 41 during an exemplary process for repairing the mitral valve using the exemplary valve repair device of FIGS. 40A-40B and the exemplary attachment member of FIG. 39.
Figure 42C:
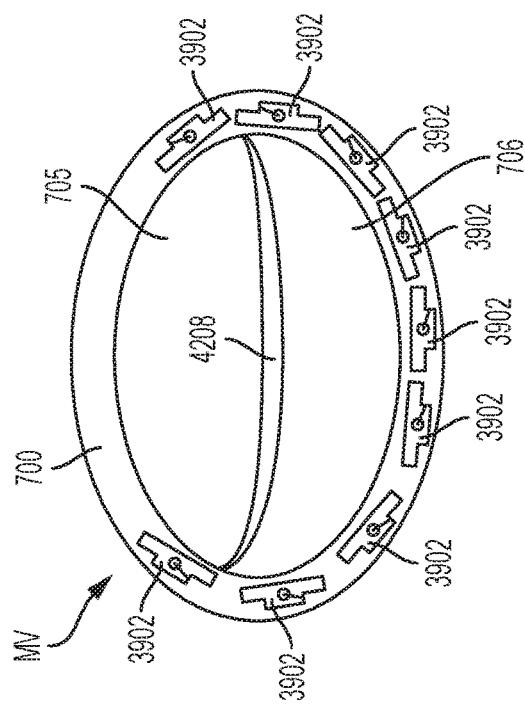

Referring to FIGS. 42A and 42B, in a first step of the exemplary mitral annuloplasty procedure, the valve repair device 4000 attaches the two or more attachment members 3902 to the annulus 700. In the illustrated embodiment, the device 4000 attaches nine attachment members 3902 to the annulus 700. In alternative embodiments, between 2 attachment members and 20 attachment members can be attached to the annulus 700, such as between 4 attachment members and 18 attachment members, such as between 6 attachment members and 16 attachment members, such as between 8 attachment members and 14 attachment members, such as between 10 attachment members and 12 attachment members, such as 11 attachment members. In certain embodiments, the device 4000 can attach more than 20 attachment members to the annulus. In an exemplary procedure, the device 2700 attaches twelve attachment members 3902 to the annulus 700. Referring to FIG. 42A, each of the attachment members 3902 are attached to the annulus 700 in the left atrium LA. Referring to FIG. 42B, each of the attachment members 3902 are attached to the annulus 700 by a suture 4016, such that providing a pulling force to the excess portion 4218 of the suture 4016 will cause the attachment members 3902 to reduce the size of the annulus 700.

Figure 42D:
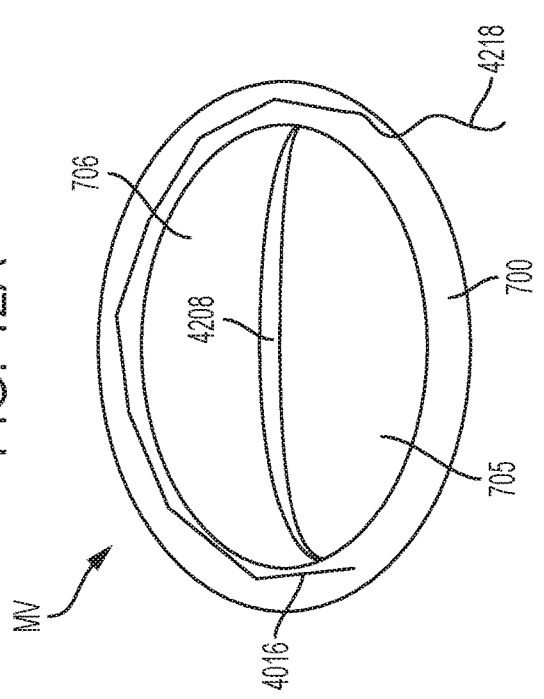

Referring to FIGS. 42C and 42D, in a second step of the exemplary mitral annuloplasty procedure, a force is applied to the excess portion 4218 of the suture 4016 in the direction X (FIG. 42D) to create a cinching effect on the annulus 700. The force applied to the suture 4016 causes a reduction in size of the annulus 700, which causes the anterior leaflet 705 and the posterior leaflet 706 to coapt (e.g., the force causes the gap 4208 to close, as shown in FIGS. 42C and 42D). Once the anterior leaflet 705 and the posterior leaflet 706 properly coapt, the suture 4016 is fixed such that the size of the annulus remains in the reduced state. In one example, the suture 4016 can be fixed to an interior wall 4101 (FIG. 41) of the left ventricle LV. For example, the suture 4016 can be fixed on an interior wall 4101 near the location of insertion by the valve repair device 4300 (or other tensioning device) through the apex A so that suture 4016 is conveniently accessible by the valve repair device (or other tensioning device) if the amount of force applied on the suture 4016 needs to be altered to reduce or expand the size of the annulus. In alternative examples, the suture 4016 can be fixed on any other location of the interior wall 4101 of the left ventricle LV that is accessible by the valve repair device 4000 (or other tensioning device), or the suture may be fixed by an anchor 5900 that is seated against the valve annulus on the ventricular side, opposite the last attachment member 3902 in the series.

Adjacent attachment members 3902 can be placed any distance apart from each other that allows the attachment members 3902 to be tensioned to repair at least a portion of the mitral valve MV. In certain exemplary procedures, the adjacent attachment members 3902 may be positioned at different distances apart from each other as compared to other adjacent attachment members. The distance between adjacent attachment members 3902 can, for example, be between about 1 mm and about 20 mm, such as between about 4 mm and about 12 mm, such as between about 6 mm and about 10 mm, such as about 8 mm. In certain embodiments, the adjacent attachment members 3902 at the ends of a group of attachment members are a smaller distance apart than the other adjacent attachment members in the group of attachment members. In this embodiment, the distance between the adjacent attachment members 3902 at the ends of the group of attachment members is between about 1 mm and about 2 mm. In certain embodiments, the attachment members 3902 are placed between one trigone (not shown) and another trigone (not shown). In some embodiments, the spacing between adjacent attachment members 3902 proximate the trigones is smaller than the distance between the other adjacent attachment members. In these embodiments, the distance between the adjacent advancement members 3902 proximate the trigones are between about 1 mm and about 2 mm.

The removal of the gap 4208 between the anterior leaflet 705 and the posterior leaflet 706 prevents regurgitation of blood from the left ventricle LV to the left atrium LA through the mitral valve MV. The suture 4016 can be tensioned and fixed by the valve repair device 4000 or a separate tensioning device (not shown). If a separate tensioning device is used, the tensioning device enters the left ventricle LV through the apex A of the heart H to engage the suture 4016.

Referring to FIGS. 43 and 44A-44D, another exemplary procedure for mitral annuloplasty is shown using the exemplary valve repair device 4300. The valve repair device 4300 has the same features as the valve repair device 4000 (FIGS. 40A and 40B), except that it is configured to enter the left atrium LA through the atrial septum of the heart H. For example, in addition to the features of the valve repair device 4000, the valve repair device 4300 may include the features of the devices described in U.S. Pat. No. 7,635,386 and U.S. Patent Application Publication No. 2014/0114404 A1, which are hereby incorporated by reference in their entireties. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 4408 in FIGS. 44A-44D), which could lead to regurgitation of blood through the mitral valve. The exemplary mitral annuloplasty procedure provides annular support to the mitral valve by reducing the size of the annulus, which allows the leaflets to properly coapt.

Figure 43:
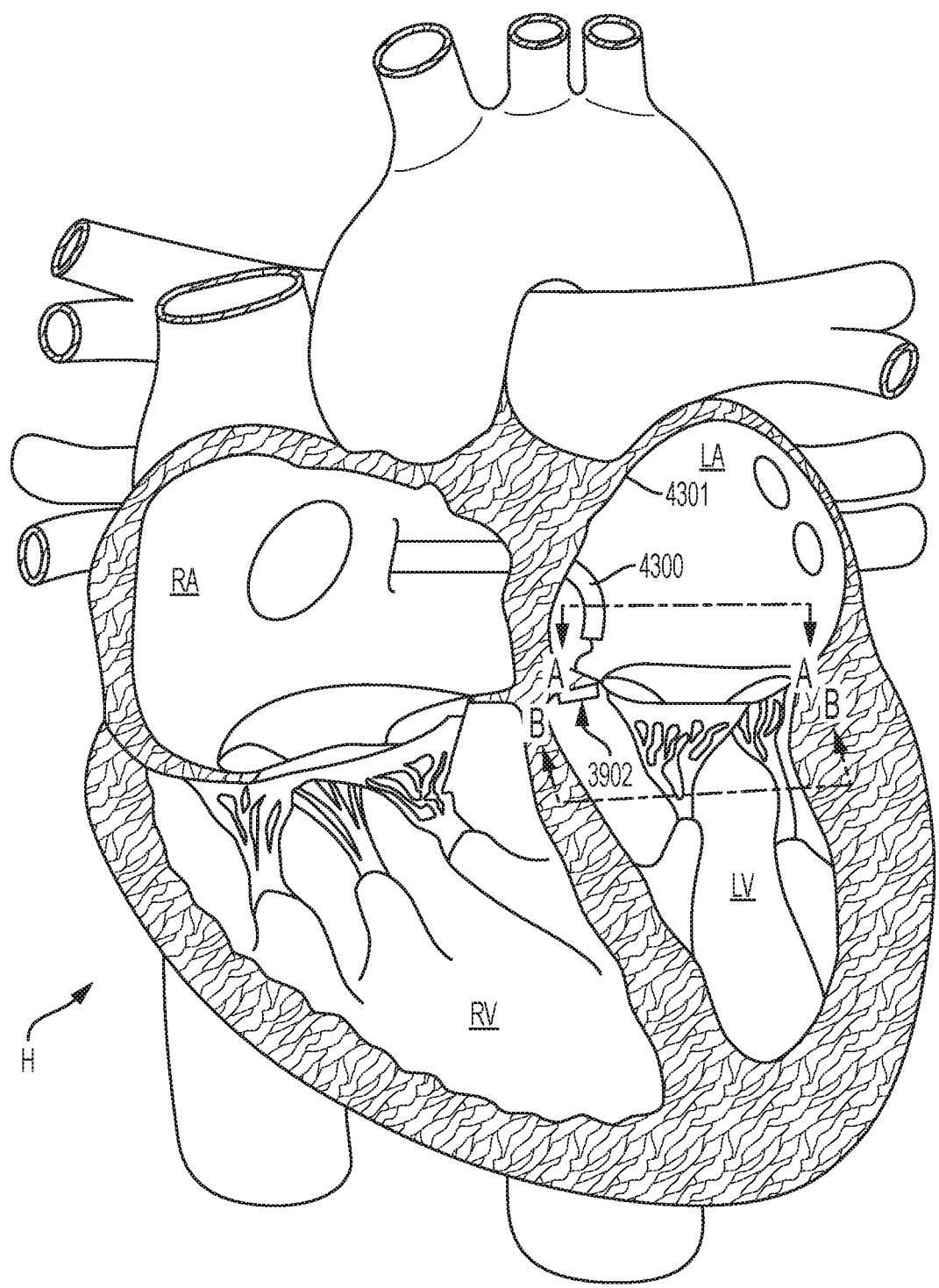
FIG. 43 is a cutaway view of the human heart showing another exemplary embodiment of a valve repair device engaging the annulus of the mitral valve through the apex of the heart and attaching the exemplary attachment member of FIG. 39 to the annulus.

Referring to FIG. 43, the valve repair device 4300 enters the left atrium LA through the atrial septum of the heart H. After the valve repair device 4300 enters the left atrium LA, the repair device 4300 engages the mitral valve MV. The valve repair device 4300 is configured to attach an attachment member 3902 to the mitral valve MV. That is, similar to the exemplary procedure shown in FIGS. 30 and 31, the valve repair device 4300 is configured to engage the annulus of the mitral valve MV from the left atrium LA, penetrate the annulus, and attach an attachment member 3902 to the annulus in the left ventricle LV. The attachment member 3902 may take any suitable form that is capable of providing annular support to the mitral valve, such as, for example, any form described in the present application.

Figure 44C:
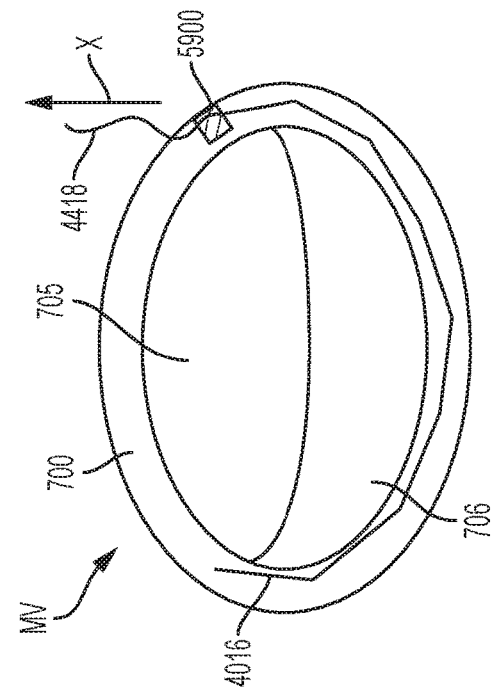
FIGS. 44A and 44C illustrate the mitral valve shown from either the perspective shown by line A-A in FIG. 43 during an exemplary process for repairing the mitral valve using the exemplary valve repair device of FIG. 43 and the exemplary attachment member of FIG. 39.

The exemplary mitral annuloplasty procedure includes attaching two or more attachment members 3902 to the annulus 700, in which the two or more attachment members 3902 are linked by a suture 4016. In addition, the exemplary procedure includes tensioning the suture 4016 (and, as a result, the two or more attachment members 3902) to reduce the size of the annulus, and, subsequently, fixing the suture once a desired reduction of the size of the annulus is achieved. The suture 4016 can be made of an ePTFE suture, a braid of suture, or any other suitable material. FIGS. 44A and 44C illustrate the mitral valve MV from the perspective of line A-A shown in FIG. 43 (e.g., illustrating the mitral valve MV from the left atrium LA), and FIGS. 44B and 44D illustrate the mitral valve MV from the perspective of line B-B shown in FIG. 43 (e.g., illustrating the mitral valve MV from the left ventricle LV).

Figure 44D:
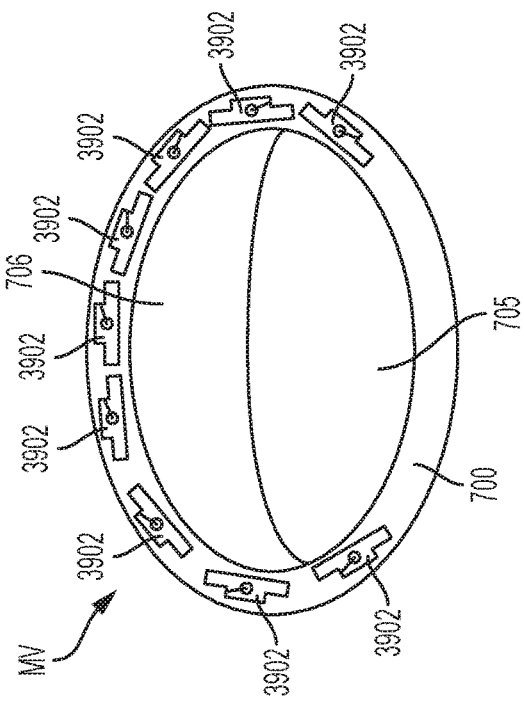
FIGS. 44B and 44D illustrate the mitral valve shown from either the perspective shown by line B-B in FIG. 43 during an exemplary process for repairing the mitral valve using the exemplary valve repair device of FIG. 43 and the exemplary attachment member of FIG. 39.
Figure 44A:
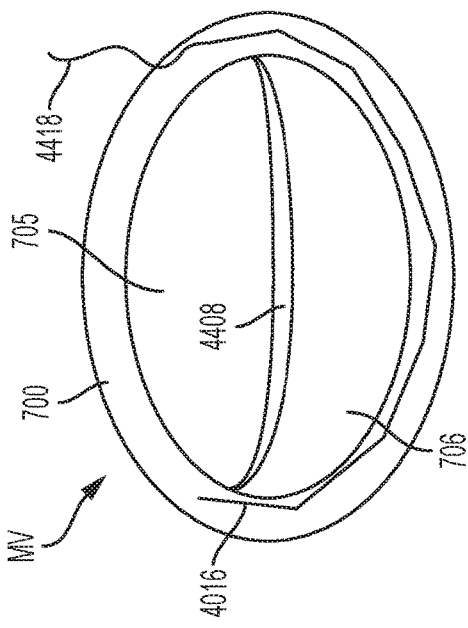
Figure 44B:
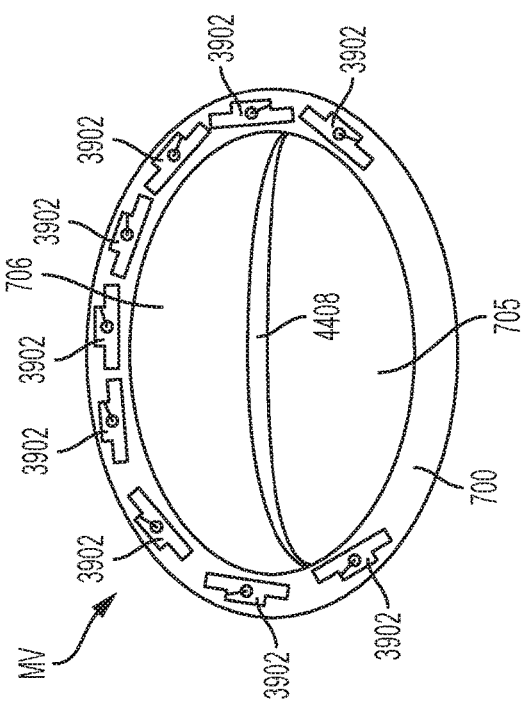

Referring to FIGS. 44A and 44B, in a first step of the exemplary mitral annuloplasty procedure, the valve device 4300 attaches the two or more attachment members 3902 to the annulus 700. In the illustrated embodiment, the device 4300 attaches nine attachment members 3902 to the annulus 700. In alternative embodiments, between 2 attachment members and 20 attachment members can be attached to the annulus 700, such as between 4 attachment members and 18 attachment members, such as between 6 attachment members and 16 attachment members, such as between 8 attachment members and 14 attachment members, such as between 10 attachment members and 12 attachment members, such as 11 attachment members. In certain embodiments, the device 4300 can attach more than 20 attachment members 3902 to the annulus. In an exemplary procedure, the device 4300 attaches twelve attachment members 3902 to the annulus 700. Referring to FIG. 44B, each of the attachment members 3902 are attached to the annulus 700 in the left ventricle LV. Referring to FIG. 44A, each of the attachment members 3902 are attached to the annulus 700 by a suture 4016, such that providing a pulling force to the excess portion 4418 of the suture 4016 will cause the attachment members 3902 to reduce the size of the annulus 700.

Referring to FIGS. 44C and 44D, in a second step of the exemplary mitral annuloplasty procedure, a force is applied to the excess portion 4418 of the suture 4016 in the direction X (FIG. 44C) to create a cinching effect on the annulus 700. The force applied to the suture 4016 causes a reduction in size of the annulus 700, which causes the anterior leaflet 705 and the posterior leaflet 706 to coapt (e.g., the force causes the gap 4408 to close, as shown in FIGS. 44C and 44D). Once the anterior leaflet 705 and the posterior leaflet 706 properly coapt, the suture 4016 is fixed such that the size of the annulus remains in the reduced state. In one example, the suture 4016 can be fixed to an interior wall 4301 (FIG. 43) of the left atrium LA. For example, the suture 4016 can be fixed on an interior wall 4301 near the location of insertion by the valve repair device 4300 (or other tensioning device) through the atrial septum so that suture 4016 is conveniently accessible by the valve repair device (or other tensioning device) if the amount of force applied on the suture 4016 needs to be altered to reduce or expand the circumference of the annulus. In alternative examples, the suture 4016 can be fixed on any other location of the interior wall 4301 of the left atrium LA that is accessible by the valve repair device 4300 (or other tensioning device), or the suture may be fixed by an anchor 5900 that is seated against the valve annulus on the atrial side, opposite the last attachment member 3902 in the series.

Adjacent attachment members 3902 can be placed any distance apart from each other that allows the attachment members 3902 to be tensioned to repair at least a portion of the mitral valve MV. In certain exemplary procedures, the adjacent attachment members 3902 may be positioned at different distances apart from each other as compared to other adjacent attachment members. The distance between adjacent attachment members 3902 can, for example, be between about 1 mm and about 20 mm, such as between about 4 mm and about 12 mm, such as between about 6 mm and about 10 mm, such as about 8 mm. In certain embodiments, the adjacent attachment members 3902 at the ends of a group of attachment members are a smaller distance apart than the other adjacent attachment members in the group of attachment members. In this embodiment, the distance between the adjacent attachment members 3902 at the ends of the group of attachment members is between about 1 mm and about 2 mm. In certain embodiments, the attachment members 3902 are placed between one trigone (not shown) and another trigone (not shown). In some embodiments, the spacing between adjacent attachment members 3902 proximate the trigones is smaller than the distance between the other adjacent attachment members. In these embodiments, the distance between the adjacent advancement members 3902 proximate the trigones are between about 1 mm and about 2 mm.

The removal of the gap 4408 between the anterior leaflet 705 and the posterior leaflet 706 prevents regurgitation of blood from the left ventricle LV to the left atrium LA through the mitral valve MV. The suture 4016 can be tensioned and fixed by the valve repair device 4300 or a separate tensioning device (not shown). If a separate tensioning device is used, the tensioning device enters the left atrium LA through the atrial septum of the heart H to engage the suture 4016.

Referring to FIG. 16A, in certain embodiments, the exemplary procedure for mitral annuloplasty shown in FIGS. 43 and 44A-44D can be completed with a transatrial procedure using valve repair device 1600'. Referring to FIG. 16A, the valve repair device 1600' enters the left atrium LA through an outer wall of the heart H. After the valve repair device 1600' enters the left atrium LA, the repair device engages the mitral valve MV. The valve repair device 1600' is configured to attach one or more attachment members (e.g., any of the attachment members described in the present application) to the mitral valve MV. The valve repair device 1600' may take any suitable form that is capable of entering the left atrium LA through an outer wall of the heart H and attaching one or more attachment members to the mitral valve. For example, the valve repair device 1600' can take the form of the devices described in U.S. Pat. No. 7,635,386 and U.S. Patent Application Publication No. 2014/0114404 A1, which are hereby incorporated by reference in their entireties.

While the example provided above (in FIGS. 42A-42D and 44A-44D) include using two or more attachment members 3902 linked by a suture 4016 to close the gap 4208, 4408 between the anterior leaflet 705 and the posterior leaflet 706, it should be understood that any number of attachment members 3902 linked by a suture can be used. In certain situations, only one sequence of attachment members 3902 linked by a suture can be required to close the gap 4208, 4408. In other situations, more than one sequence of attachment members 3902 linked by one or more sutures can be used to close the gap 4208, 4408. The attachment members 3902 can be attached to any location on the annulus 700 in order to cause the anterior leaflet 705 and the posterior leaflet 706 to properly coapt.

While the valve repair devices 4000, 4300, 1600' and the exemplary annuloplasty procedures provided above are described with reference to repairing the mitral valve MV, it should be understood that the valve repair devices and the concepts used in the exemplary mitral annuloplasty procedures can be used to repair any native valve. For example, the valve repair devices 4000, 4300, 1600' and the concepts of the exemplary annuloplasty procedures described above can be used to repair the aortic valve AV, the tricuspid valve TV, and the pulmonary valve PV.

Figure 45A:
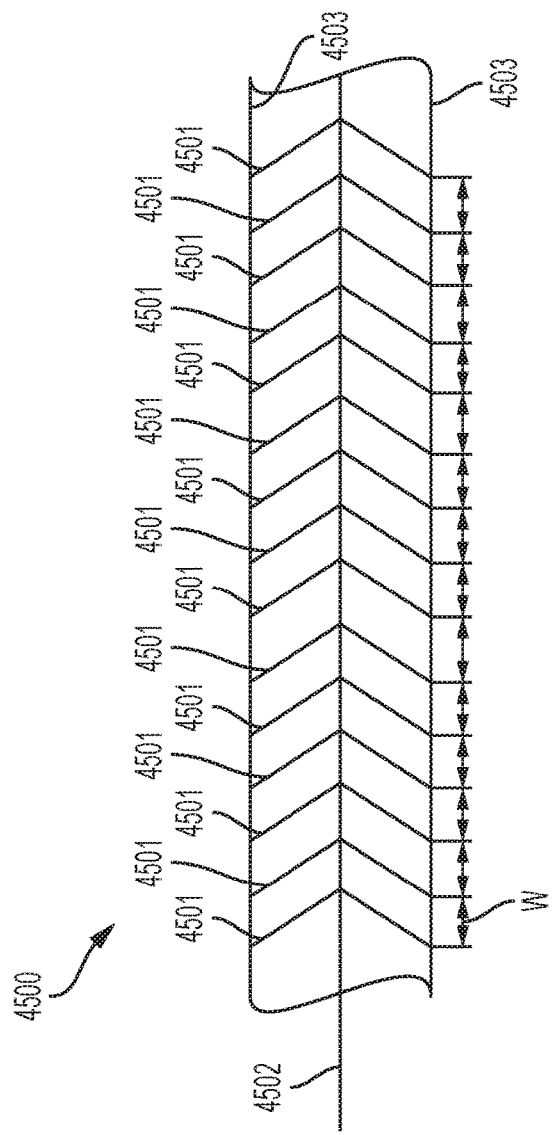
FIGS. 45A-45B illustrate an exemplary embodiment of an annuloplasty band.
Figure 45B:
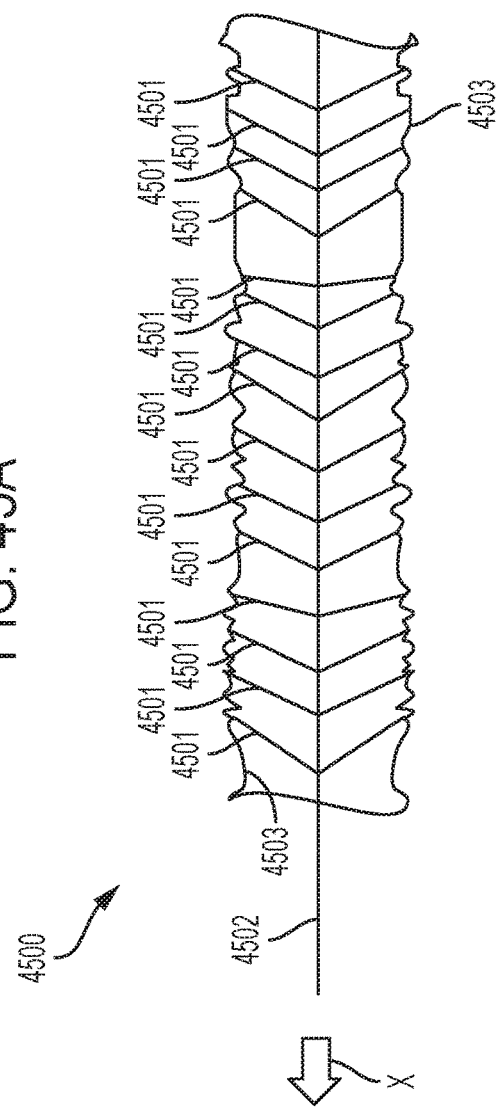

Referring to FIGS. 45A-45B, an exemplary embodiment of an annuloplasty band 4500 includes a plurality of adjustable chords 4501, a main chord 4502, and a cover 4503. Referring to FIG. 45A, the adjustable chords 4501 branch from the main chord 4502 at evenly spaced increments having a width W. The width may be, for example, between about 0.5 mm and about 1.5 mm, such as between about 0.75 mm and about 1.25 mm, such as about 1 mm. In an alternative embodiment, the adjustable chords may be unevenly spaced apart. Referring to FIG. 45B, upon applying a force in the direction X to the main chord 4502 causes the adjustable chords 4501 to tighten or shorten the annuloplasty band 4500. That is, applying a force in the direction X to the main chord causes a cinching effect of the annuloplasty band 4500.

Figure 46A:
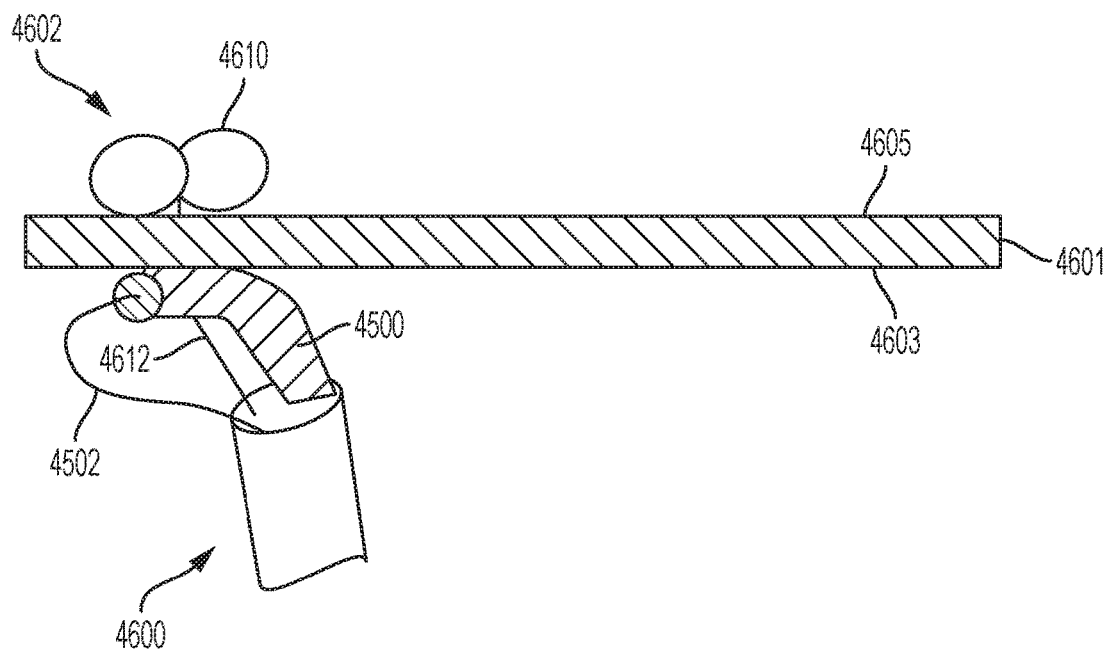
FIGS. 46A-46B illustrate an exemplary embodiment of a valve repair device attaching the exemplary embodiment of the annuloplasty band of FIGS. 45A-45B to a tissue member.
Figure 46B:
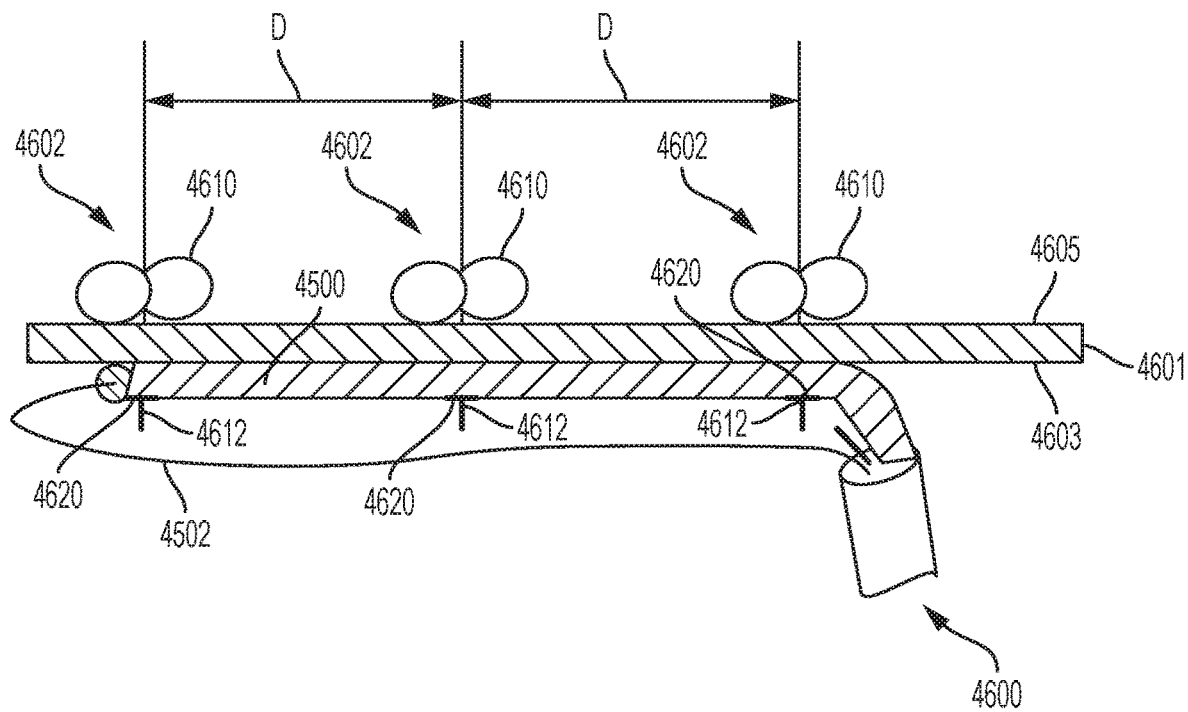

Referring to FIGS. 46A and 46B, an exemplary embodiment of a valve repair device 4600 is shown attaching the annuloplasty band 4500 of FIGS. 45A-45B to a tissue member 4601 (e.g., the annulus of the mitral valve, the annulus of the tricuspid valve, etc.). The valve repair device 4600 is configured to attach the annuloplasty band 4500 to the tissue member by an attachment member 4602. In the illustrated embodiment, the attachment member 4602 includes a securing portion 4610 and a suture portion 4612 (e.g., similar to the attachment member 602 having a securing portion 710 and the suture portion 712 shown in FIGS. 5 through 19E). In the illustrated embodiment, the securing portion 4610 of the attachment member 4602 is a knot. The securing portion 4610 is configured to prevent the attachment member 4602 from being removed from the tissue member and/or the annuloplasty band 4500 when a force is applied to the suture portion 4612. In alternative embodiments, the attachment member 4602 may take any suitable form that is capable of attaching the annuloplasty band 4500 to the tissue member, such as, for example, any form described in the present application.

In the illustrated example, the valve repair device 4600 is configured to both incrementally deploy the annuloplasty band 4500 against the tissue member 4601 and deploy the attachment members 4602. In another exemplary embodiment, two separate devices are used to deploy the annuloplasty band 4500 and the attachment members 4502. In the illustrated embodiment, the main chord 4502 of the annuloplasty band 4500 is connected to the device 4600. After the annuloplasty band 4500 is attached to the tissue member 4601, the device 4600 can be used to apply a force to the main chord 4502 to cause a cinching effect of the annuloplasty band 4500 and, as a result, the tissue member 4801. The annuloplasty band 4500 can be deployed by any suitable means, such as, for example, by the means used by the devices disclosed in U.S. Pat. Nos. 8,518,107, 8,911,494, 9,402,732, U.S. Patent Application Publication No. 2016/008132 A1, and U.S. Patent Application Publication No. 2014/0309661 A1, which are hereby incorporated by reference in their entireties. The device 4600 is configured to attach an attachment member 4602 to the tissue member 4601 by deploying the securing portion 4610 of the attachment member 4602 through the annuloplasty band 4500 and through the tissue member 4601, such that the suture portion 4612 of the attachment member extends from the securing portion 4610 through tissue member 4601 and through the annuloplasty band 4500. The device 4600 can take any suitable form that is capable of attaching the annuloplasty band 4500 to the tissue member 4601 by an attachment member 4602. For example, the attachment member portion of the device 4600 can take the form of the devices described in U.S. Pat. No. 7,635,386 and U.S. Patent Application Publication No. 2014/0114404 A1, which are hereby incorporated by reference in their entireties. The device 4600 can deploy the attachment members 4602 in any of the manners that any of the attachment members or pledgets described herein are deployed.

Referring to FIG. 46A, a first portion of the annuloplasty band 4500 is deployed from the device 4600 such that the portion of the band 4500 is abutting a first side 4603 of the tissue member 4601. In addition, the main chord 4502 of the band 4500 is shown extending from the band 4500 to the band portion of the repair device 4600. Still referring to FIG. 46A, after the portion of the band 4500 is abutting the tissue member 4601, the device 4600 deploys an attachment member 4602 through the band 4500 and the tissue member 4601, such that the securing portion 4610 of the attachment member 4602 is attached to a second side 4605 of the tissue member 4601, and such that the suture portion 4612 of the attachment member extends from the securing portion 4610 through the tissue member 4601 and the band 4500. As shown in FIG. 46A, after the device 4600 attaches the securing portion 4610 of the attachment member 4602 to the second side 4605 of the tissue member 4601, the suture portion 4612 remains attached to the device 4600. Once the attachment member 4602 attaches the portion of the annuloplasty band 4500 to the tissue member 4601, the device 4500 is configured to cut the suture portion 4612 of the attachment member 4602, such that the suture portion 4612 extends below band 4500. In other exemplary embodiments, the suture portion 4612 is not cut.

Referring to FIG. 46B, the device 4600 is configured to continue deploying the annuloplasty band 4500 until the entire band is abutting the tissue member 4601. In addition, the device 4600 is configured to attach the band 4500 to the tissue member 4601 by attaching one or more attachment members through the band 4500 and the tissue member 4601. FIG. 46B illustrates a portion of the band 4500 connected to the tissue member 4601 by three attachment members 4602. The attachment member 4602 is locked in position by attaching an anchor 4620 to each suture portion 4612. The anchor 4620 may take any suitable form that is capable of securing an attachment member 4602 to the band 4500 and tissue member 4601. For example, the anchor 4620 can take any of the forms described in the present application (See, for example, FIGS. 59-61). In certain embodiments, the suture portions 4612 of adjacent attachment members are tensioned together using a single anchor (e.g., similar to the cinching of sutures 712 of the pairs of attachment members 602 disclosed in FIGS. 5 through 10A-10F). In yet another exemplary embodiment, the suture is not cut between attachment members and an anchor 4620 is provided only after the last attachment member 4602 is deployed (See FIGS. 33A-33D and 44A-44D)

After the annuloplasty band 4500 is attached to the tissue member 4601 by one or more attachment members 4602, a pulling force is applied to the main chord 4502 of the band 4500, which causes a cinching effect on the band 4500. The cinching of the band 4500 causes the attachment member 4602 to provide a force on the tissue member 4601, such that the cinching effect occurs with the tissue member 4601. Once the tissue member 4601 is reduced by a desired amount, the main chord 4502 of the band is fixed to keep the tissue member in the desired reduced state.

The attachment members 4602 can be disposed such that the distance D between each of the attachment members 4602 is the same or different. In exemplary procedures, the distance D can be between about 3 mm and about 30 mm, such as between about 8 mm and about 25 mm, such as between about 13 mm and about 20 mm, such as about 15 mm. In certain embodiments, the distance D is between about 5 mm and about 15 mm, such as between about 8 mm and about 12 mm, such as about 10 mm. If an even load distribution is desired, the distance D between each of the attachment members 4602 should be substantially the same. If an uneven load is desired, the distance D between each of the attachment members 4602 can be different. In one exemplary embodiment, the distance D between the attachment members 4602 disposed at the ends of the annuloplasty band 4500 is smaller than the distance D between the attachment members disposed on the middle portion of the annuloplasty band.

Referring to FIGS. 47 and 48A-48D, another exemplary procedure for mitral annuloplasty is shown using the exemplary valve repair device 4600 (FIGS. 46A and 46B). The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 4808 in FIGS. 48A-48D), which could lead to regurgitation of blood through the mitral valve. The exemplary mitral annuloplasty procedure provides annular support to the mitral valve by reducing the size of the annulus, which allows the leaflets to properly coapt.

Figure 47:
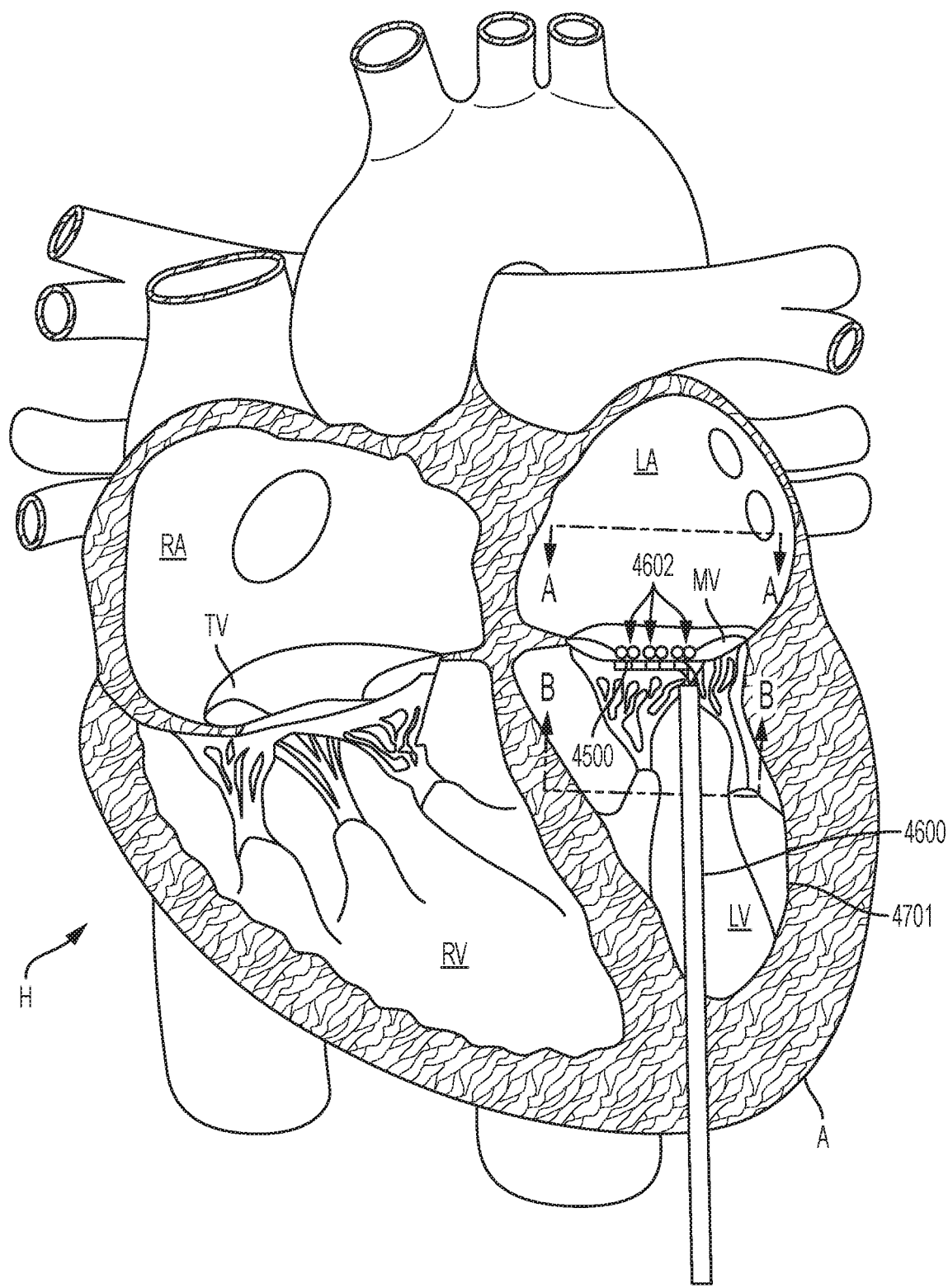
FIG. 47 is a cutaway view of the human heart showing the exemplary embodiment of the valve repair device of FIGS. 46A-46B engaging the annulus of the mitral valve through the apex of the heart and attaching the exemplary embodiment of the annuloplasty ring shown in FIGS. 45A and 45B to the annulus.

Referring to FIG. 47, the valve repair device 4600 enters the left ventricle LV through the apex A of the heart H. After the valve repair device 4600 enters the left ventricle LV, the repair device engages the mitral valve MV. The valve repair device 4300 is configured to attach an annuloplasty band 4500 to the mitral valve MV by one or more attachment members 4602 (as shown in FIGS. 48A-48D). The valve repair device 4600 may take any suitable form that is capable of entering the left ventricle LV through the apex A of the heart H and attaching an annuloplasty band 4500 to the mitral valve MV by one or more attachment members 4602, such as, for example, any form described in the present application. The attachment member 4602 may take any suitable form that is capable of attaching the annuloplasty band 4500 to the mitral valve, such as, for example, any form described in the present application.

Figure 48C:
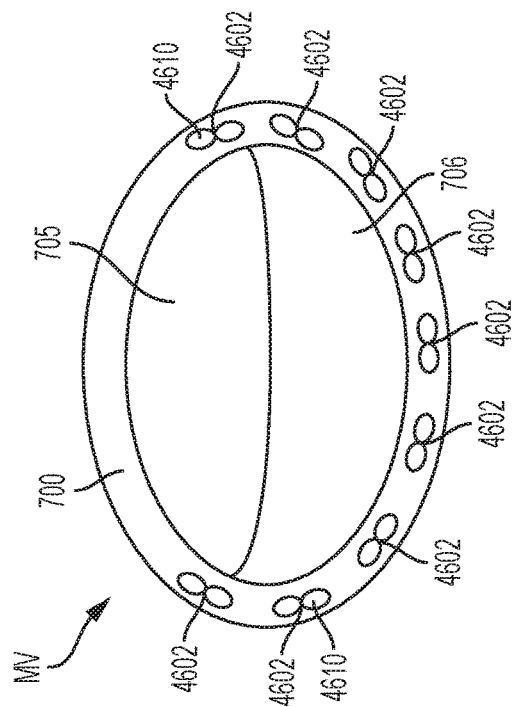
FIGS. 48A and 48C illustrate the mitral valve shown from the perspective shown by line A-A in FIG. 47 during an exemplary process for repairing the mitral valve using the exemplary valve repair device of FIGS. 46A-46B and the exemplary annuloplasty band of FIGS. 45A-45B.

The exemplary mitral annuloplasty procedure includes attaching the annuloplasty band 4500 to the annulus 700 of the mitral valve with one or more attachment members 4602. In addition, the exemplary procedure includes tensioning a main chord 4502 (FIGS. 45A-45B) of the band 4500 (and, as a result, the one or more attachment members 4602) to reduce the size of the annulus, and, subsequently, fixing the main chord 4502 of the band 4500 once a desired reduction of the size of the annulus is achieved. That is, similar to the exemplary procedure shown in FIGS. 46A and 46B, the valve repair device 4500 is configured to engage the annulus of the mitral valve MV from the left ventricle LV, attach an annuloplasty band 4500 to the annulus by one or more attachment members 4602, and applying a force to the main chord 4502 of the band 4500 to reduce the size of the annulus. The main chord 4502 can be made of an ePTFE suture, a braid of suture, or any other suitable material. FIGS. 48A and 48C illustrate the mitral valve MV from the perspective of line A-A shown in FIG. 47 (e.g., illustrating the mitral valve MV from the left atrium LA), and FIGS. 48B and 48D illustrate the mitral valve MV from the perspective of line B-B shown in FIG. 47 (e.g., illustrating the mitral valve MV from the left ventricle LV).

Figure 48D:
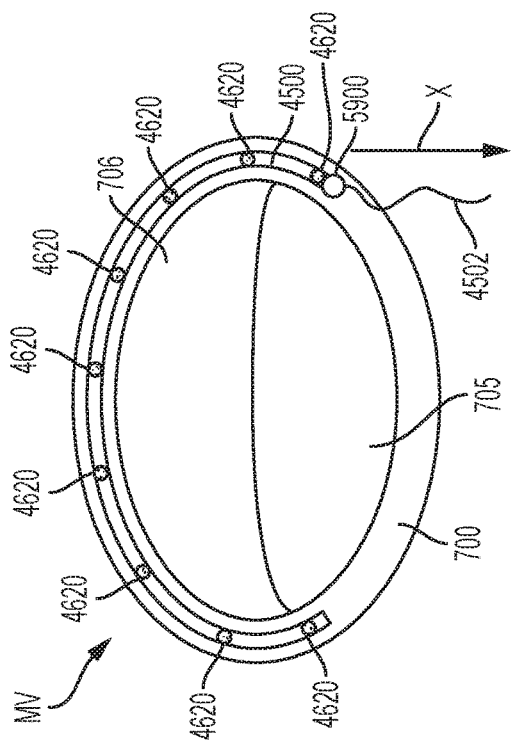
FIGS. 48B and 48D illustrate the mitral valve shown from the perspective shown by line B-B in FIG. 47 during an exemplary process for repairing the mitral valve using the exemplary valve repair device of FIGS. 46A-46B and the exemplary annuloplasty band of FIGS. 45A-45B.
Figure 48A:
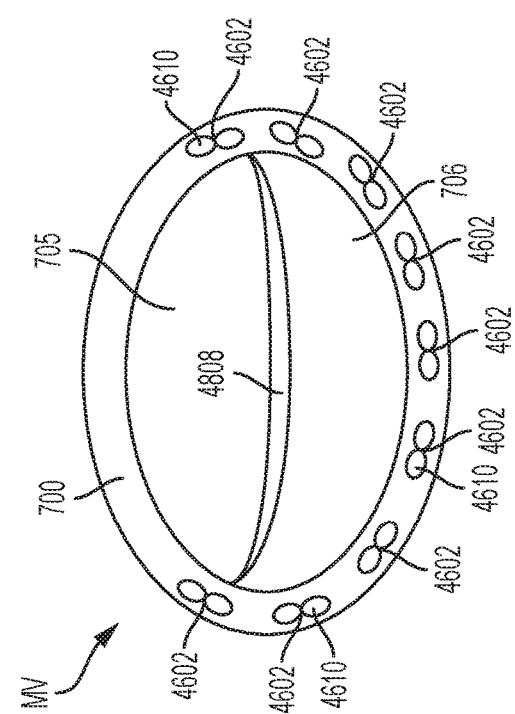
Figure 48B:
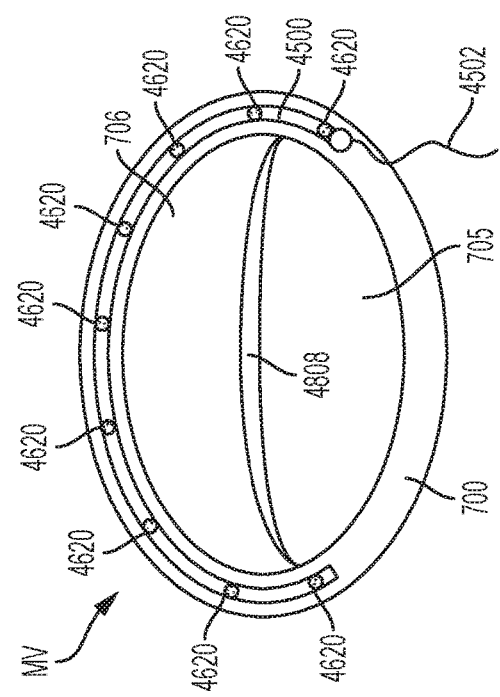

Referring to FIGS. 48A and 48B, in a first step of the exemplary mitral annuloplasty procedure, the valve device 4600 attaches the annuloplasty band 4500 to the annulus 700 by two or more attachment members 4602. In the illustrated embodiment, the device 4000 attaches the band 4500 to the annulus 700 with nine attachment members 4602. In alternative embodiments, between 2 attachment members and 20 attachment members can be used, such as between 4 attachment members and 18 attachment members, such as between 6 attachment members and 16 attachment members, such as between 8 attachment members and 14 attachment members, such as between 10 attachment members and 12 attachment members, such as 11 attachment members. In certain embodiments, the device 4600 can attach the band 4500 to the annulus 700 by more than 20 attachment members. Referring to FIG. 48A, the securing portions 4610 (FIGS. 46A-46B) of the attachment members 4602 extend into the left atrium LA. Referring to FIG. 48B, the annuloplasty band 4500 is attached to the annulus 700 in the left ventricle LV, and the attachment members 4602 are locked to the annulus 700 and the band 4500 by anchors 4620. In addition, the band 4500 is attached to the annulus such that providing a pulling force to the main chord 4502 of the band 4500 will cause the band 4500 and attachment members 4602 to reduce the size of the annulus 700.

Referring to FIGS. 48C and 48D, in a second step of the exemplary mitral annuloplasty procedure, a force is applied to the main chord 4502 of the band 4500 in the direction X (FIG. 48D) to create a cinching effect on the annulus 700. The force applied to the main chord 4502 causes a reduction in size of the annulus 700, which causes the anterior leaflet 705 and the posterior leaflet 706 to coapt (e.g., the force causes the gap 4808 to close, as shown in FIGS. 48C and 48D). The proper coaptation between the anterior leaflet 705 and the posterior leaflet 706 prevents regurgitation of blood from the left ventricle LV to the left atrium LA through the mitral valve MV. Once the anterior leaflet 705 and the posterior leaflet 706 properly coapt, the main chord 4502 is fixed such that the size of the annulus remains in the reduced state. In one example, the main chord 4502 can be fixed to an interior wall 4701 (FIG. 47) of the left ventricle LV. For example, the main chord 4502 can be fixed on an interior wall 4701 near the location of insertion by the valve repair device 4600 through the apex A so that main chord 4502 is conveniently accessible by the valve repair device if the amount of force applied on the main chord 4502 needs to be altered to reduce or expand the size of the annulus. In alternative examples, the main chord 4502 can be fixed on any other location of the interior wall 4701 of the left ventricle LV that is accessible by the valve repair device 4600, or the suture may be fixed to the end of the band 4500 by an anchor 5900 (See, for example, FIGS. 61A-61C).

Adjacent attachment members 4602 can be placed any distance apart from each other that allows the attachment members 4602 to attach the annuloplasty band 4500 to the annulus 700 and be tensioned to repair at least a portion of the mitral valve MV. In certain exemplary procedures, the adjacent attachment members 4602 can be positioned at different distances apart from each other as compared to other adjacent attachment members.

Referring to FIGS. 49 and 50A-50D, another exemplary procedure for mitral annuloplasty is shown using the exemplary valve repair device 4900. The mitral annuloplasty procedure is used to correct a dysfunctional mitral valve MV. The valve repair device 4900 has the same features as the valve repair device 4600 (FIGS. 46A and 46B), except that it is configured to enter the left atrium LA through the atrial septum of the heart H. For example, in addition to the features of the valve repair device 4600, the valve repair device 4900 may include the features of the devices described in U.S. Pat. No. 7,635,386 and U.S. Patent Application Publication No. 2014/0114404 A1, which are hereby incorporated by reference in their entireties. The mitral annuloplasty procedure is used to correct a dysfunctional mitral valve MV. As described above, in certain situations, the anterior leaflet 705 and the posterior leaflet 706 of the mitral valve MV may not coapt (e.g., see mitral valve MV having gap 5008 in FIGS. 50A-50D), which could lead to regurgitation of blood through the mitral valve. The exemplary mitral annuloplasty procedure provides annular support to the mitral valve by reducing the size of the annulus, which allows the leaflets to properly coapt.

Figure 49:
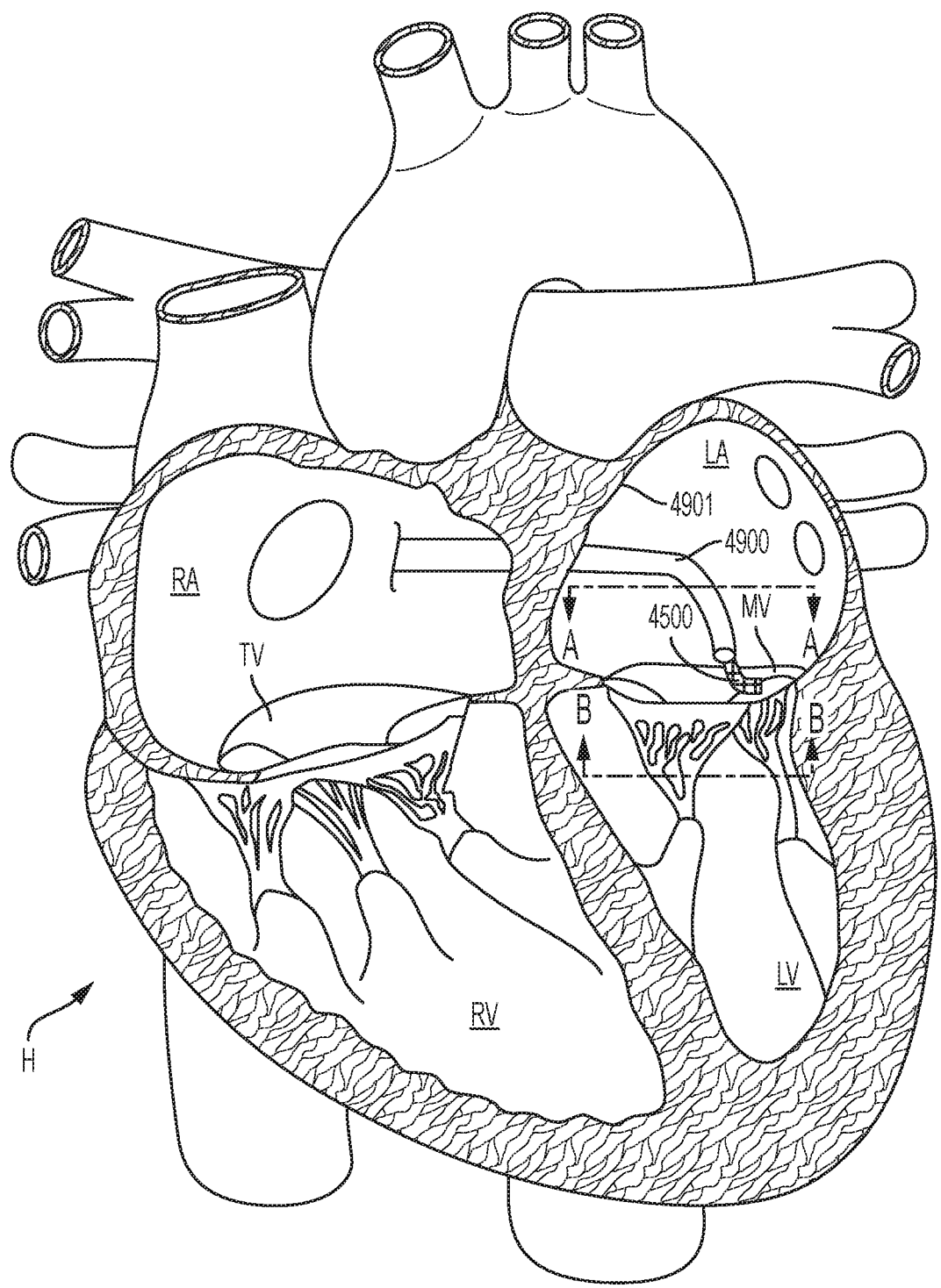
FIG. 49 is a cutaway view of the human heart showing another exemplary embodiment of the valve repair device engaging the annulus of the mitral valve through the apex of the heart and attaching the exemplary embodiment of the annuloplasty ring shown in FIGS. 45A and 45B to the annulus.

Referring to FIG. 49, the valve repair device 4900 enters the left atrium LA through the atrial septum of the heart H. After the valve repair device 4900 enters the left atrium LA, the repair device engages the mitral valve MV. The valve repair device 4900 is configured to attach an annuloplasty band 4500 to the mitral valve MV by one or more attachment members 4602 (as shown in FIGS. 50A-50D). The attachment member 4602 may take any suitable form that is capable of attaching the annuloplasty band 4500 to the mitral valve, such as, for example, any form described in the present application.

Figure 50A:
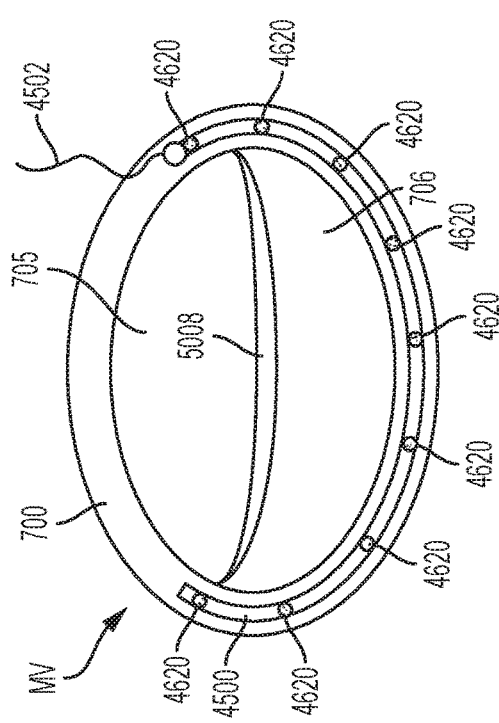
FIGS. 50A and 50C illustrate the mitral valve shown from either the perspective shown by line A-A in FIG. 49 during an exemplary process for repairing the mitral valve using the exemplary valve repair device of FIG. 49 and the exemplary annuloplasty band of FIGS. 45A-45B.

The exemplary mitral annuloplasty procedure includes attaching the annuloplasty band 4500 to the annulus 700 of the mitral valve with one or more attachment members 4602. In addition, the exemplary procedure includes tensioning a main chord 4502 (FIGS. 45A-45B) of the band 4500 (and, as a result, the one or more attachment members 4602) to reduce the size of the annulus, and, subsequently, fixing the main chord 4502 of the band 4500 once a desired reduction of the size of the annulus is achieved. That is, similar to the exemplary procedure shown in FIGS. 46A and 46B, the valve repair device 4900 is configured to engage the annulus of the mitral valve MV from the left atrium LA, attach an annuloplasty band 4500 to the annulus by one or more attachment members 4602, and applying a force to the main chord 4502 of the band 4500 to reduce the size of the annulus. The chord 4502 can be made of an ePTFE suture, a braid of suture, or any other suitable material. FIGS. 50A and 50C illustrate the mitral valve MV from the perspective of line A-A shown in FIG. 49 (e.g., illustrating the mitral valve MV from the left atrium LA), and FIGS. 50B and 50D illustrate the mitral valve MV from the perspective of line B-B shown in FIG. 49 (e.g., illustrating the mitral valve MV from the left ventricle LV).

Figure 50B:
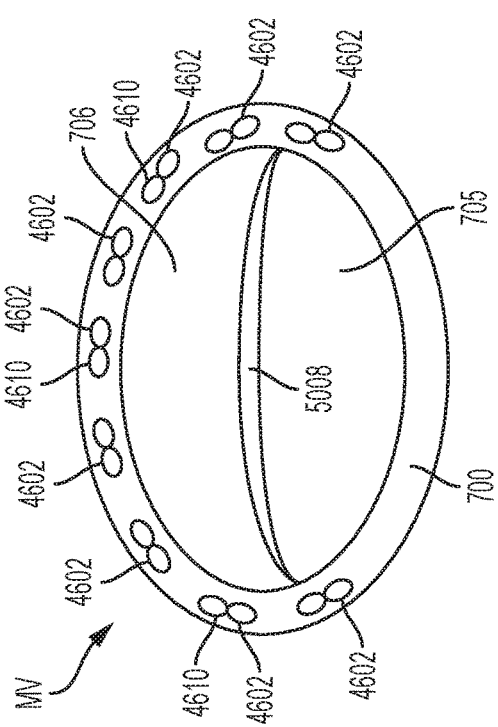
FIGS. 50B and 50D illustrate the mitral valve shown from either the perspective shown by line B-B in FIG. 49 during an exemplary process for repairing the mitral valve using the exemplary valve repair device of FIG. 49 and the exemplary annuloplasty band of FIGS. 45A-45B.
Figure 50C:
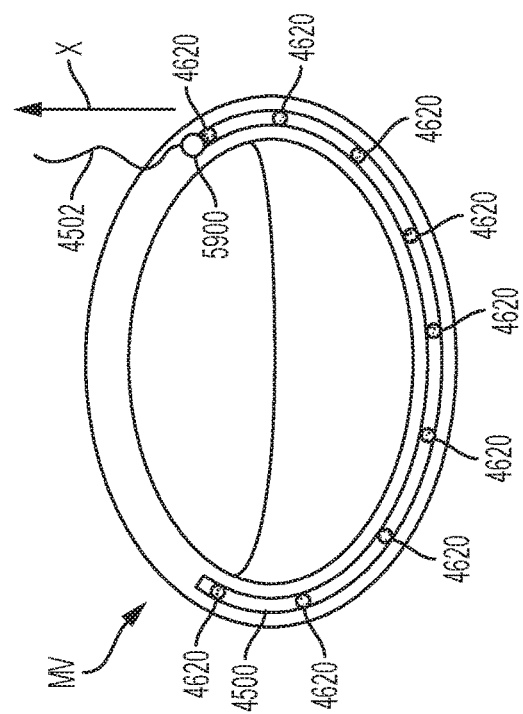

Referring to FIGS. 50A and 50B, in a first step of the exemplary mitral annuloplasty procedure, the valve device 4900 attaches the annuloplasty band 4500 to the annulus 700 by two or more attachment members 4602. In the illustrated embodiment, the device 4900 attaches the band 4500 to the annulus 700 with nine attachment members 4602. In alternative embodiments, between 2 attachment members and 20 attachment members can be used, such as between 4 attachment members and 18 attachment members, such as between 6 attachment members and 16 attachment members, such as between 8 attachment members and 14 attachment members, such as between 10 attachment members and 12 attachment members, such as 11 attachment members. In certain embodiments, the device 4900 can attach the band 4500 to the annulus 700 by more than 20 attachment members. Referring to FIG. 50B, the securing portions 4610 (FIGS. 46A-46B) of the attachment members 4602 extend into the left atrium LA. Referring to FIG. 50A, the annuloplasty band 4500 is attached to the annulus 700 in the left ventricle LV, and the attachment members 4602 are locked to the annulus 700 and the band 4500 by anchors 4620. In addition, the band 4500 is attached to the annulus such that providing a pulling force to the main chord 4502 of the band 4500 will cause the band 4500 and attachment members 4602 to reduce the size of the annulus 700.

Figure 50D:
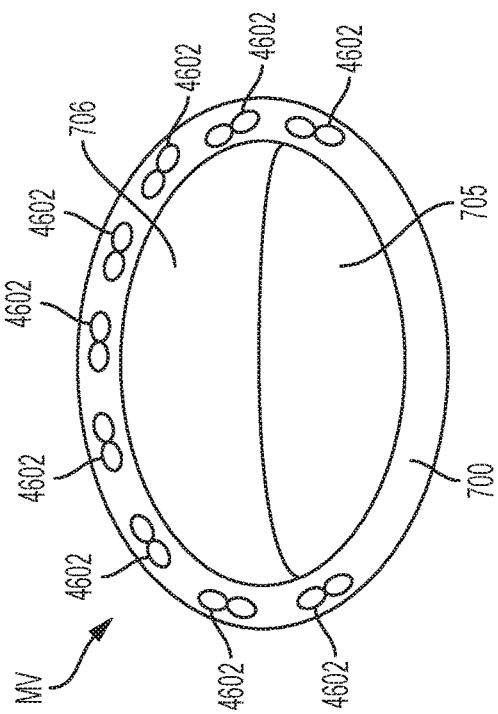

Referring to FIGS. 50C and 50D, in a second step of the exemplary mitral annuloplasty procedure, a force is applied to the main chord 4502 of the band 4500 in the direction X (FIG. 50C) to create a cinching effect on the annulus 700. The force applied to the main chord 4502 causes a reduction in size of the annulus 700, which causes the anterior leaflet 705 and the posterior leaflet 706 to coapt (e.g., the force causes the gap 5008 to close, as shown in FIGS. 50C and 50D). The proper coaptation between the anterior leaflet 705 and the posterior leaflet 706 prevents regurgitation of blood from the left ventricle LV to the left atrium LA through the mitral valve MV. Once the anterior leaflet 705 and the posterior leaflet 706 properly coapt, the main chord 4502 is fixed such that the size of the annulus remains in the reduced state. In one example, the main chord 4502 can be fixed to an interior wall 4901 (FIG. 49) of the left atrium LA. For example, the main chord 4502 can be fixed on an interior wall 4901 near the location of insertion by the valve repair device 4900 through the atrial septum so that main chord 4502 is conveniently accessible by the valve repair device if the amount of force applied on the main chord 4502 needs to be altered to reduce or expand the size of the annulus. In alternative examples, the main chord 4502 can be fixed on any other location of the interior wall 4901 of the left atrium LA that is accessible by the valve repair device 4900, or the suture may be fixed to the end of the band 4500 by an anchor 5900 (See, for example, FIGS. 61A-61C).

Adjacent attachment members 4602 can be placed any distance apart from each other that allows the attachment members 4602 to attach the annuloplasty band 4500 to the annulus 700 and be tensioned to repair at least a portion of the mitral valve MV. In certain exemplary procedures, the adjacent attachment members 4602 can be positioned at different distances apart from each other as compared to other adjacent attachment members.

Referring to FIG. 16A, in certain embodiments, the exemplary procedure for mitral annuloplasty shown in FIGS. 49 and 50A-50D can be completed with a transatrial procedure using valve repair device 1600'. Referring to FIG. 16A, the valve repair device 1600' enters the left atrium LA through an outer wall of the heart H. After the valve repair device 1600' enters the left atrium LA, the repair device engages the mitral valve MV. The valve repair device 1600' is configured to attach an annuloplasty band 4500 to the mitral valve MV by one or more attachment members 4602 (as shown in FIGS. 50A-50D). The attachment member 4602 may take any suitable form that is capable of attaching the annuloplasty band 4500 to the mitral valve, such as, for example, any form described in the present application. The valve repair device 1600' may take any suitable form that is capable of entering the left atrium LA through an outer wall of the heart H and attaching the annuloplasty band 4500 to the mitral valve by one or more attachment members. For example, the valve repair device 1600' can take the form of the devices described in U.S. Pat. No. 7,635,386 and U.S. Patent Application Publication No. 2014/0114404 A1, which are hereby incorporated by reference in their entireties.

While the valve repair devices 4600, 4900, 1600' and the exemplary annuloplasty procedures provided above are described with reference to repairing the mitral valve MV, it should be understood that the valve repair devices and the concepts used in the exemplary mitral annuloplasty procedures can be used to repair any native valve. For example, the valve repair devices 4600, 4900, 1600' and the concepts of the exemplary annuloplasty procedures described above can be used to repair the aortic valve AV, the tricuspid valve TV, and the pulmonary valve PV.

Figure 51A:
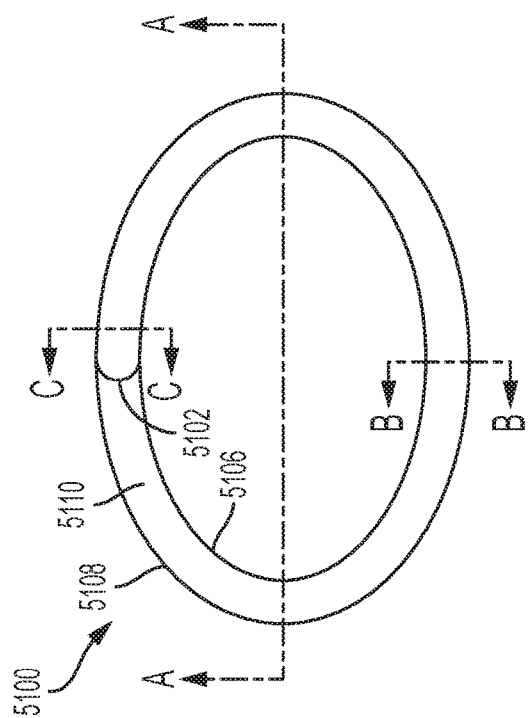
FIGS. 51A-51C illustrate another exemplary embodiment of an annuloplasty band.
Figure 51B:
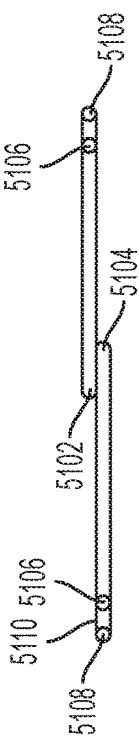
Figure 51C:
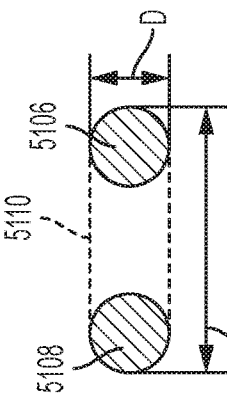

Referring to FIGS. 51A-51C, another exemplary embodiment of an annuloplasty band 5100 includes a first end 5102 and a second end 5104. The band 5100 is capable of being configured so that the band 5100 matches the shape of the annulus of the patient. That is, referring to FIG. 51A, the band 5100 has an original shape that matches the annulus of the patient. The band 5100 is made of an elastic material that allows the band to be placed through a small tube (e.g., a tube of a valve repair device) that causes the band to take the form of the tube, and the band 5100 is configured to return to its original shape upon being deployed out of the small tube. For example, the band 5100 can be made of Nitinol or another shape memory alloy. In the illustrated embodiment, the band 5100 includes an inner wire 5106, an outer wire 5108, and a cover 5110 that extends over the inner wire and the outer wire. The inner wire 5106 and the outer wire 5108 can be made of a metal material, such as, for example, Nitinol or another shape memory alloy. The cover 5110 can be made out of, for example, a knit cloth, a woven cloth, PTFE, ePTFE, etc.

FIG. 51B is a cross-sectional view of the band 5100 shown from the perspective of lines A-A. Referring to FIG. 51B, in certain embodiments, the first end 5102 and the second end 5104 of the band 5100 overlap when the band 5100 when the band is in its original shape. FIG. 51C is a cross-sectional view of the band 5100 shown from the perspective of lines B-B.

Figure 52A:
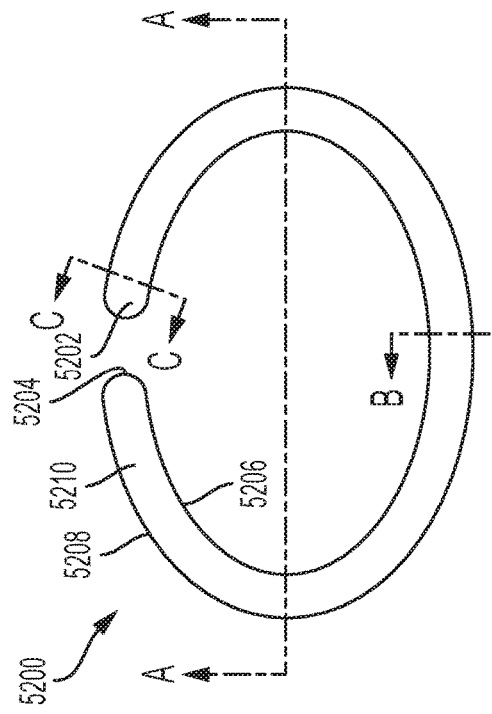
FIGS. 52A-52C illustrate another exemplary embodiment of an annuloplasty band.
Figure 52B:
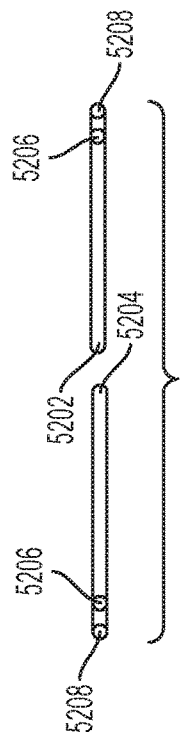
Figure 52C:
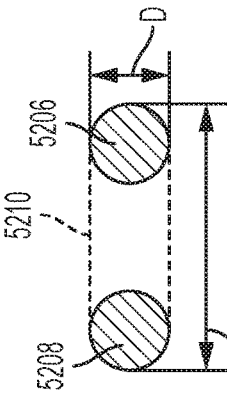

Referring to FIGS. 52A-52C, another exemplary embodiment of an annuloplasty band 5200 includes a first end 5202 and a second end 5204. The band 5200 is capable of being configured so that the band 5200 matches at least a portion of the shape of the annulus of the patient. That is, referring to the embodiment illustrated in FIG. 52A, the band 5200 has an original shape that substantially matches the annulus of the patient's mitral valve. In alternative embodiments, the original shape of the band 5200 can match a portion of the shape of the annulus of the patient (e.g., the band 5200 can match only half of the patient's annulus). The band 5200 is made of an elastic material that allows the band to be placed through a small tube (e.g., a tube of a valve repair device) that causes the band to take the form of the tube, and the band 5200 is configured to return to its original shape upon being deployed out of the small tube. For example, the band 5200 can be made of Nitinol or another shape memory alloy. In the illustrated embodiment, the band 5200 includes an inner wire 5206, an outer wire 5208, and a cover 5210 that extends over the inner wire and the outer wire. The inner wire 5206 and the outer wire 5208 can be made of a metal material, such as, for example, Nitinol. The cover 5210 can be made out of, for example, a knit fabric, a woven cloth, PTFE, ePTFE, etc.

FIG. 52B is a cross-sectional view of the band 5200 shown from the perspective of lines A-A. Referring to FIG. 52B, in certain embodiments, the first end 5102 and the second end 5104 of the band 5100 do not overlap when the band 5200 when the band is in its original shape. FIG. 52C is a cross-sectional view of the band 5200 shown from the perspective of lines B-B.

Referring to FIGS. 53-58, another exemplary procedure for mitral annuloplasty is shown using an exemplary embodiment of a valve repair device 5300. The mitral annuloplasty procedure is used to correct a dysfunctional mitral valve MV. As described above, in certain situations, the anterior leaflet and the posterior leaflet of the mitral valve MV may not coapt, which could lead to regurgitation of blood through the mitral valve. The exemplary mitral annuloplasty procedure provides annular support to the mitral valve by reducing the size of the annulus, which allows the leaflets to properly coapt.

Figure 53:
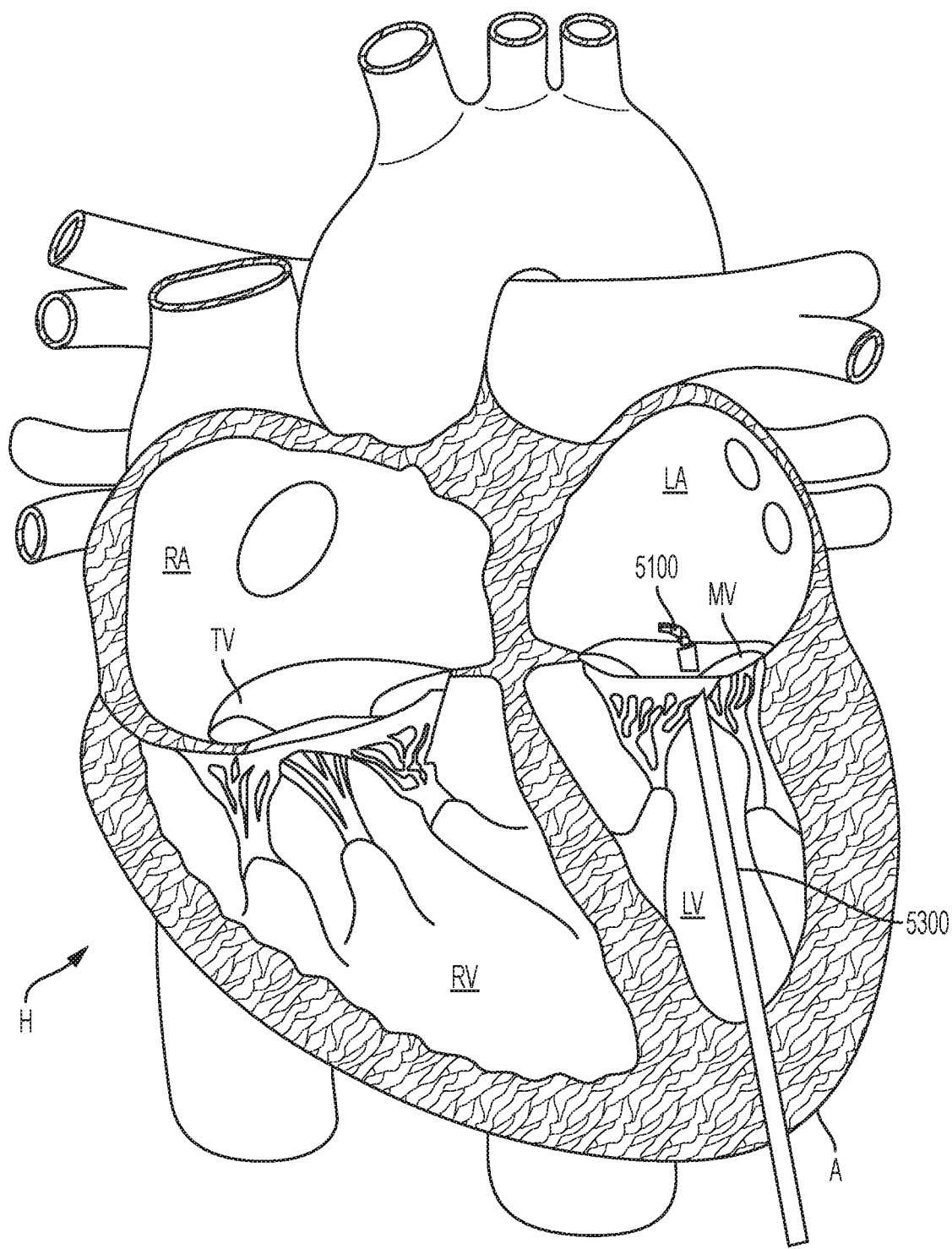
FIG. 53 is a cutaway view of the human heart showing another exemplary embodiment of a valve repair device engaging the annulus of the mitral valve through the apex of the heart and attaching the exemplary annuloplasty band of FIGS. 51A-51C to the annulus.
Figure 54:
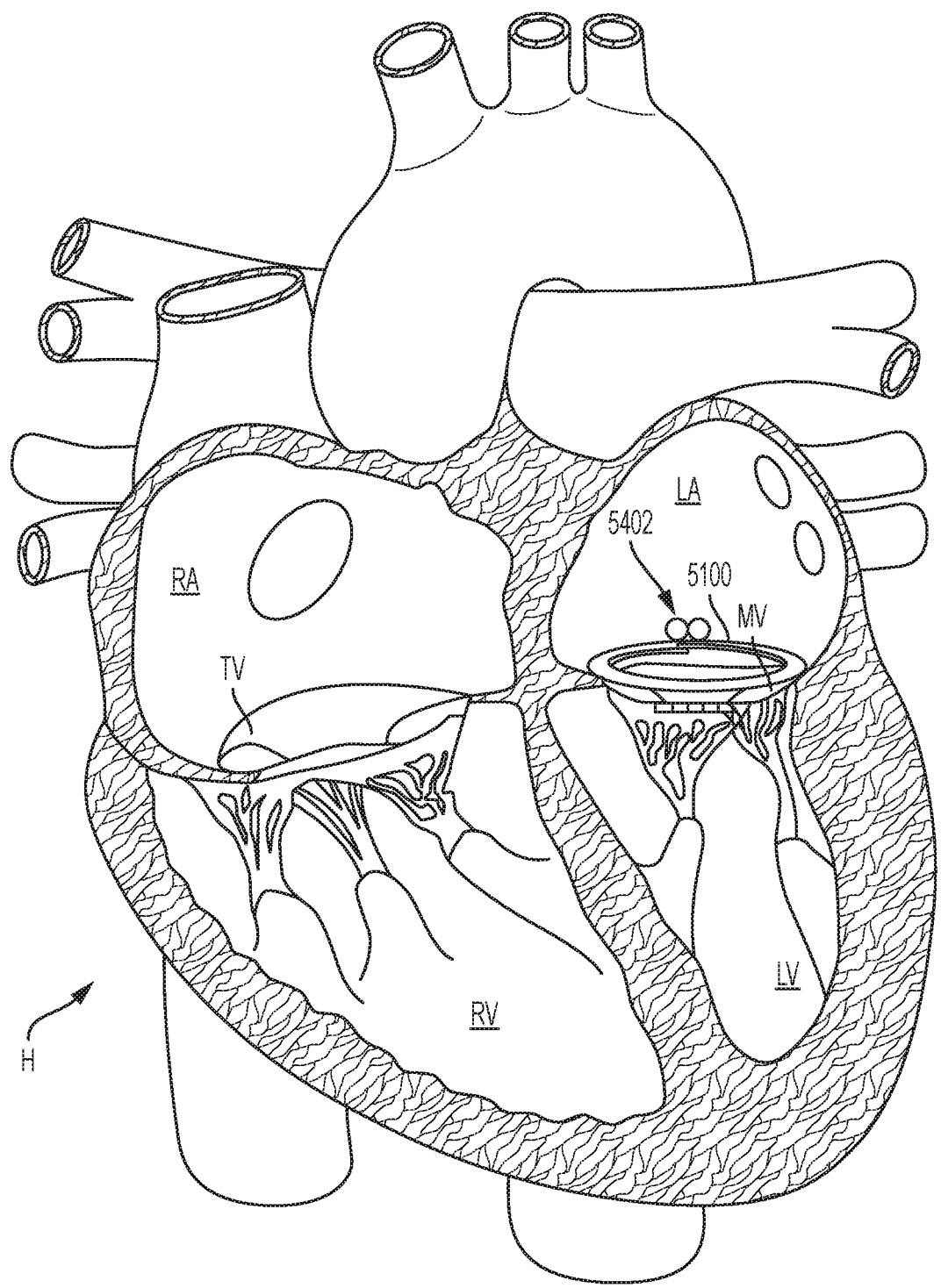
FIG. 54 is a cutaway view of the human heart after the exemplary annuloplasty band of FIGS. 51A-51C is attached to the annulus of the mitral valve.

Referring to FIGS. 53 and 54, the valve repair device 5300 enters the left ventricle LV through the apex A of the heart H. After the valve repair device 5300 enters the left ventricle LV, the repair device engages the mitral valve MV. The valve repair device 5300 is configured to attach the exemplary annuloplasty band 5100 shown in FIGS. 51A-51C to the mitral valve MV by one or more attachment members 5402 (FIG. 54). In an alternative procedure, the device 5300 is configured to attach the exemplary annuloplasty band 5200 shown in FIGS. 52A-52C to the mitral valve by one or more attachment members. The valve repair device 5300 may take any suitable form that is capable of entering the left ventricle LV through the apex A of the heart H and attaching an annuloplasty band 5100 (or, alternatively, annuloplasty band 5200) to the mitral valve MV by one or more attachment members 5402. For example, the device 5300 may take a similar form to the device 4600 shown in FIGS. 46A and 46B, or the form of any device described in the present application. The attachment member 5402 may take any suitable form that is capable of attaching the annuloplasty band 5100 (or band 5200) to the mitral valve, such as, for example, any form described in the present application.

The exemplary mitral annuloplasty procedure includes attaching the annuloplasty band 5100 to the annulus of the mitral valve MV with one or more attachment members 5402. The band 5100 (or band 5200) is deployed by the valve repair device 5300 such that the band is abutting the annulus. The band 5100 is maintained on the annulus by a holding tool (not shown) of the device 5300 to allow the device 5300 to attach the one or more attachment members to the band 5100 and the annulus. In an alternative procedure, a separate holding tool (e.g., a holding tool that is not a part of the device 5300) is used to maintain the band 5100 on the annulus. The holding tool of the device 5300 (or the separate holding tool) can be, for example, an L-shaped tool, a vacuum tool, a suction tool, a lanyard, etc. In certain procedures, the band 5100 (or band 5200) is maintained on the annulus by friction.

As described above, the annuloplasty band 5100 (and annuloplasty band 5200) is made of an elastic material and/or a shape memory material that is configured to return to its original shape upon being deployed by the device 5300. The original shape of the band 5100 is made such that, when the band is attached to the annulus, the band has a shaping effect on the annulus, which corrects the size and/or shape of the annulus. Referring to FIG. 54, the annuloplasty band 5100 (or annuloplasty band 5200) is attached to a top surface of the annulus. In an alternative embodiment, the annuloplasty band can be attached to a bottom surface of the annulus.

Referring to FIGS. 55-58, the annuloplasty band 5100 (FIGS. 51A-51C and 55-56) or the annuloplasty band 5200 (FIGS. 52A-52C and 57-58) is shown after it is attached to the annulus 700 by an exemplary embodiment of an attachment member 5402. The attachment member 5402 includes an atrial portion 5510 that attaches above the top surface 5501 of the annulus 700 and extends into the left atrium LA. In addition, the attachment member 5402 includes a ventricular portion 5512 below the bottom surface 5503 of the annulus 700 and extends into the left ventricle. In certain embodiments, the attachment member 5402 can be similar to the attachment member 2102 shown in FIGS. 21-24. In the illustrated embodiment, the atrial portion 5510 and the ventricular portion 5512 of the attachment member 5402 are knots that are connected by a suture portion 5516. The atrial portion 5510 is configured to prevent the attachment member 5402 from being removed from the annulus 700 when a force is applied to the ventricular portion 5512, and the ventricular portion 5512 is configured to prevent the attachment member 5402 from being removed from the annulus when a force is applied to the atrial portion 5510. The attachment members 5402 attach the annuloplasty band 5100, 5200 to the annulus 700 by a valve repair device 5300, which may take any suitable form, such as, for example, any form described in the present application. The valve repair device 5300 may enter the left atrium LA or the left ventricle LV, such as, for example, by any means provided in the present application, in order to attach the attachment members 5402 to the band 5100, 5200 and the annulus 700.

Figure 55:
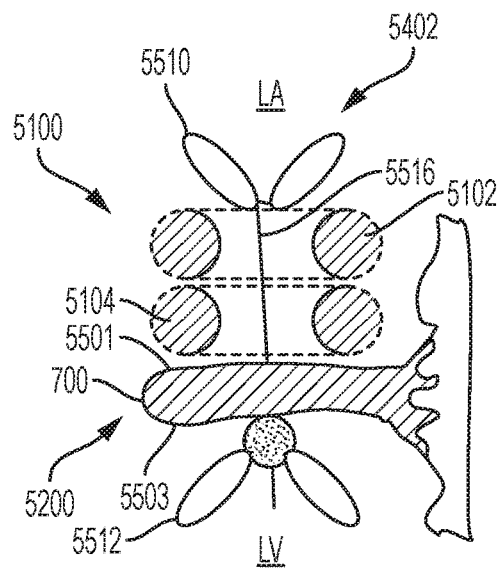
FIG. 55 is a cross-sectional view of an exemplary attachment between the exemplary annuloplasty band of FIGS. 51A-51C and the annulus, in which the annuloplasty band is placed on a top surface of the annulus.
Figure 56:
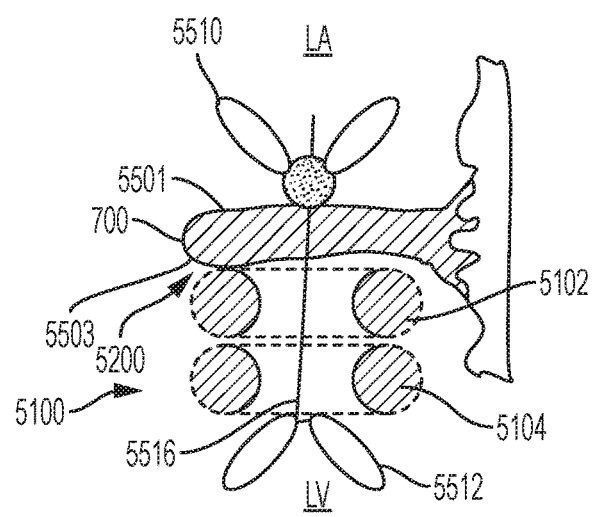
FIG. 56 is a cross-sectional view of an exemplary attachment between the exemplary annuloplasty band of FIGS. 51A-51C and the annulus, in which the annuloplasty band is placed on a bottom surface of the annulus.

FIGS. 55 and 56 illustrate the annuloplasty band 5100 (FIGS. 51A-51C) shown from the perspective of line C-C (FIG. 51A) after the band 5100 is attached to the annulus 700 by an attachment member 5402. That is, the first end 5102 of the band 5100 is overlapped with the second end 5104 of the band 5100, and an attachment member 5402 is attaching the first end 5102 and second end 5104 of the band 5100 to the annulus 700 in order to secure the band 5100 to the annulus 700. Referring to FIG. 55, the band 5100 is attached to the top surface 5501 of the annulus 700. Referring to FIG. 56, the band 5100 is attached to the bottom surface 5503 of the annulus 700. While the band 5100 is described as being attached to the annulus 700 at the first end 5102 and the second end 5104 of the band 5100, in certain embodiments, one or more attachment members 5402 are also attached throughout the remainder of the band 5100 in order to secure the band 5100 to the annulus 700.

Figure 57:
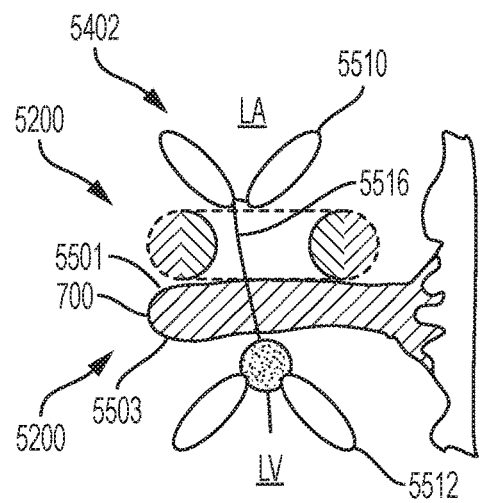
FIG. 57 is a cross-sectional view of an exemplary attachment between the exemplary annuloplasty band of FIGS. 52A-52C and the annulus, in which the annuloplasty band is placed on a top surface of the annulus.
Figure 58:
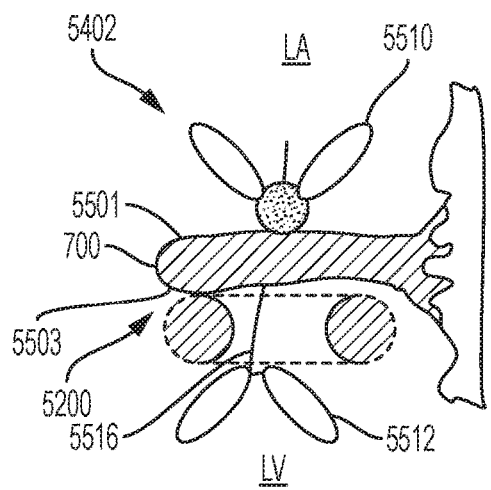
FIG. 58 is a cross-sectional view of an exemplary attachment between the exemplary annuloplasty band of FIGS. 52A-52C and the annulus, in which the annuloplasty band is placed on a bottom surface of the annulus.

FIGS. 57 and 58 illustrate the annuloplasty band 5200 (FIGS. 52A-52C) shown from the perspective of line C-C (FIG. 52A) after the band 5200 is attached to the annulus 700 by an attachment member 5402. That is, the first end 5202 of the band 5200 is attached to the annulus 700 by an attachment member 5402 in order to secure the band 5200 to the annulus 700. In addition, although not shown in the illustrated embodiment, the second end 5204 of the band 5200 is attached to the annulus by another attachment member 5402. Referring to FIG. 57, the band 5200 is attached to the top surface 5501 of the annulus 700. Referring to FIG. 58, the band 5200 is attached to the bottom surface 5503 of the annulus 700. While the band 5200 is described as being attached to the annulus 700 at the first end 5202 and the second end 5204 of the band 5200, in certain embodiments, one or more attachment members 5402 are also attached throughout the remainder of the band 5200 in order to secure the band 5200 to the annulus 700.

The shapes of the annuloplasty bands 5100, 5200 can optionally be adjusted after they have been attached to an annulus. For example, the bands 5100, 5200 may include a chord 4502 (See FIGS. 45A-45B) that is used to change the size and/or shape of the band 5100, 5200 and attached annulus. In other exemplary embodiments, the annuloplasty bands 5100, 5200 include other mechanisms for changing the shape and/or size of the annulus 700.

In alternative embodiments, the annuloplasty bands 5100, 5200 are attached by attachment members 5402 that require an anchor member to be secured to the annulus 700. For example, the attachment member 5402 can include a securing portion (not shown) and a suture portion (not shown), such as, for example, the attachment member 602 shown in FIGS. 5 through 19A-19F; an attachment member having a securing portion, a suture portion, and a ring (e.g., see FIGS. 63A-63B and 64); a T-shaped attachment member (e.g., see FIGS. 61A-61B and 62), or any other embodiment of an attachment member that requires an anchor member to be secured to the annulus 700. The anchor member can take any suitable form that is capable of securing the attachment member 5402 to the annulus 700, such as, for example, any form described in U.S. Pat. No. 9,078,645, which is herein incorporated by reference in its entirety or any of the anchors disclosed in this application.

Figure 59B:
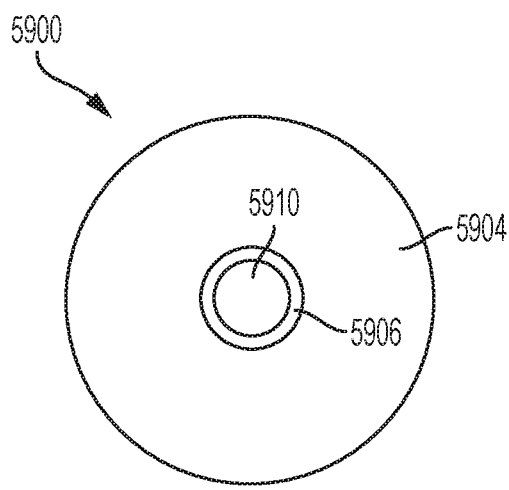
FIG. 59A-59C illustrate an exemplary embodiment of an anchor member.
Figure 59A:
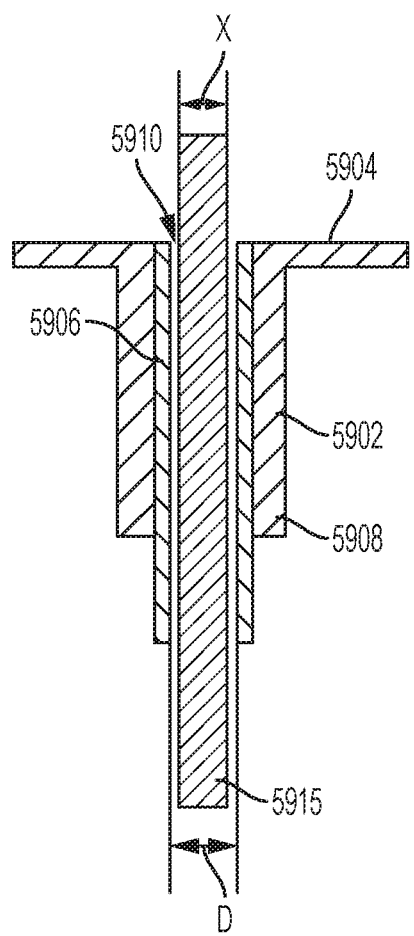
Figure 59C:
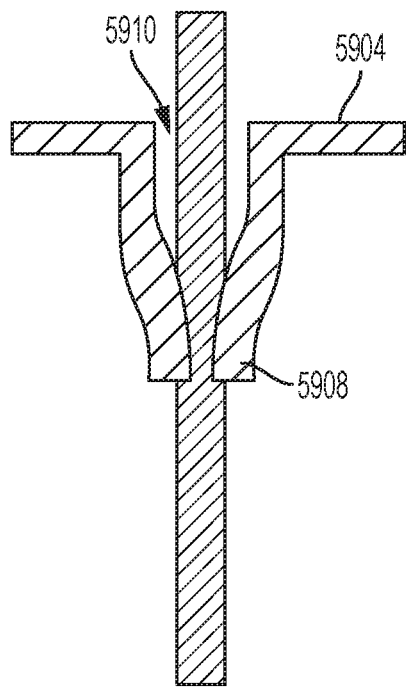

Referring to FIGS. 59A-59B and 60, another exemplary embodiment of an anchor member 5900 includes a compression portion 5902, an abutment portion 5904, a placement member 5906, and an opening 5910 that extends through the abutment portion 5904 and the compression portion 5902. The opening 5910 is configured to receive a suture portion 5915 of an attachment member. The compression portion 5902 is configured to compress the suture portion 5906 of an attachment member to prevent the attachment member from moving. The placement member 5906 is configured to expand the compression portion 5902 so that the opening 5910 has a larger diameter D than the diameter X of the suture portion 5915. The placement member 5906 allows the anchor member 5900 to be moved along the suture portion 5915 so that the anchor member 5900 can be placed in a desired location on the suture portion 5915. Once the anchor member 5900 is placed in a desired location, the placement member 5906 can be removed from the anchor member 5900, which causes at least a portion of the compression member 5902 to compress such that the diameter D of at least a portion of the opening 5910 is less than the diameter X of the suture portion 5915. That is, the compression portion 5902 is made of an elastic material or a shape memory material, such as, for example, plastic, steel, shape memory alloy material, such as Nitinol, any combination of these materials, and the like. The compression portion 5902 is made so that it has an original shape (e.g., the shape of the compression portion 5902 that is shown in FIG. 59C). The original shape of the compression portion 5902 makes at least a portion of the opening 5910 have a smaller diameter D than the diameter X of the suture portion 5915. The placement member 5906 is configured to expand the compression portion 5902 such that the entire opening 5910 has a diameter D that is larger than the diameter X of the suture portion 5915, which allows the anchor member 5900 to be moved up and down the suture portion 5915. For example, the placement member 5906 may be a cylindrical sleeve. Upon removing the placement member 5906, the compression portion 5902 moves back to its original shape, which causes at least a portion of the compression portion 5902 to compress and secure the suture portion 5915 in a desired position/location with respect to the compression portion 5902. Referring to FIG. 59C, in the illustrated embodiment, the anchor member 5900 is configured such that a lower portion 5908 of the compression portion 5902 is configured to compress the suture portion 5915. In alternative embodiments, any other portion of the compression portion may be used to compress the suture portion 5915, or the entire compression portion 5902 can compress the suture 5915. The abutment portion 5904 is configured to abut against an object that the attachment member is attached to, such as, for example, the annulus, an annuloplasty band, or any other object that the attachment member is attached to. The anchor member 5900 can be made of, for example, plastic, metal, steel, shape memory alloys, combinations of these materials, and the like. The placement member 5906 can be removed by holding the anchor in place and pulling the placement member 5906 or holding the placement member in place and advancing the anchor.

FIGS. 60A-60C illustrate the exemplary anchor member 5900 attaching an exemplary embodiment of an attachment member 5402 to a tissue member 6001 (e.g., the annulus of the mitral valve, the annulus of the tricuspid valve, etc.). In the illustrated embodiment, the attachment member 5402 is a T-shaped attachment member that includes a securing portion 6010 and a suture portion 6015. The securing portion 6010 abuts a second side 6003 of the tissue member 6001, and the suture portion extends through the tissue member 6001 to a first side 6002 of the tissue member 6001. After the attachment member 5402 is attached to the tissue member 6001, the attachment member 5402 is secured to the tissue member 6001 by the anchor member 5900. Referring to FIG. 60A, the anchor member 5900 is moved along the suture portion 6015 with the placement member 5906 maintaining the opening 5910 in an expanded state. Referring to FIG. 60B, the anchor member 5900 is placed in a desired location in which the abutment portion 5904 of the anchor member 5900 is abutting the first side 6002 of the tissue member 6001. Referring to FIG. 60C, after the anchor member 5900 is placed in a desired location, the placement member 5906 is removed, which causes a lower portion 5908 of the compression portion to compress against the suture portion 6015. The compression by the compression portion 5902 on the suture portion 6015 secures the attachment member 5402 to the tissue member 6001.

FIGS. 61A-61C illustrate the exemplary anchor member 5900 attaching an exemplary embodiment of an attachment member 5402 to a tissue member 6101 (e.g., the annulus of the mitral valve, the annulus of the tricuspid valve, etc.). In the illustrated embodiment, the attachment member 5402 includes a first securing portion 6110, a second securing portion 6111, a suture portion 6115, and a ring 6112. The suture portion 6115 is fixed to the first securing portion 6110. The first securing portion 6110 abuts a second side 6103 of the tissue member 6101, and the suture portion 6115 extends through the tissue member 6101 to a first side 6102 of the tissue member 6101. The second securing portion 6111 is slideably coupled to the suture portion 6115 by the ring 6112. The second securing portion 6111 and ring 6112 is located on a first side 6102 of the tissue member 6101. After the attachment member 5402 is attached to the tissue member 6101, the attachment member 5402 is secured to the tissue member 6101 by the anchor member 5900. Referring to FIG. 61A, the anchor member 5900 is moved along the suture portion 6115 with the placement member 5906 maintaining the opening 5910 in an expanded state. Referring to FIG. 61B, the anchor member 5900 is placed in a desired location in which the abutment portion 5904 of the anchor member 5900 is abutting the second securing portion 6111, which causes the second securing portion 6111 to compress the ring 6112 against the first side 6102 of the tissue member 6101. Referring to FIG. 61C, after the anchor member 5900 is placed in a desired location, the placement member 5906 is removed, which causes a lower portion 5908 of the compression portion to compress against the suture portion 6115. The compression by the compression portion 5902 on the suture portion 6115 secures the attachment member 5402 to the tissue member 6101.

Figure 63:
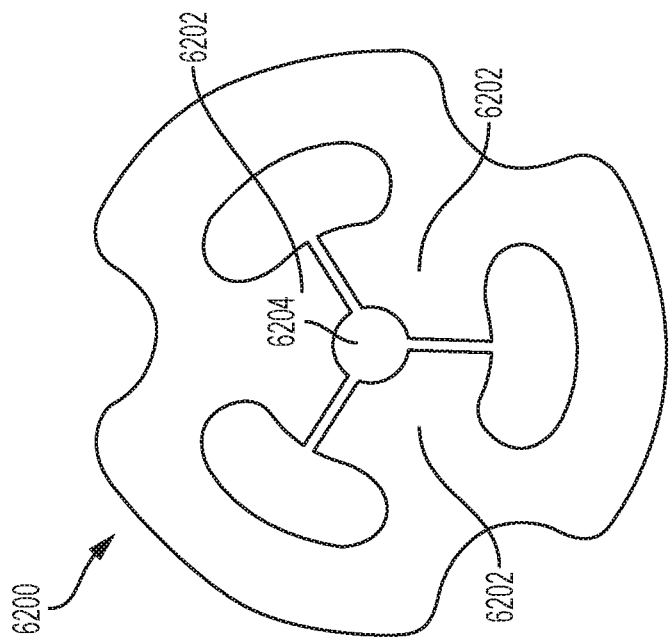
FIG. 62-63 illustrate another exemplary embodiment of an anchor member.
Figure 62:
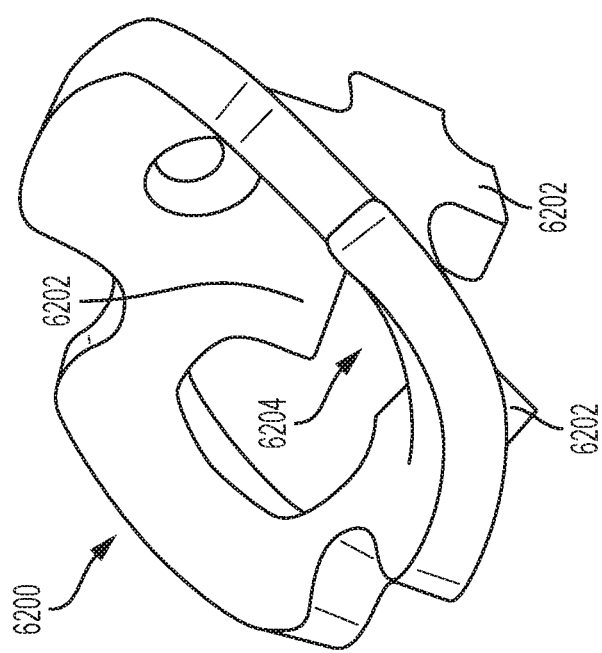

Referring to FIGS. 62 and 63, another exemplary embodiment of an anchor member 6200 includes three or more flap members 6202. The illustrated embodiment shows an anchor member 6220 that has three flap members 6202. In alternative embodiments, the anchor member 6200 can have four flap members, five flap members, etc. The flap members 6202 are deflectable, such that each of the flap members 6202 can move from an open position (FIG. 62) to a closed position (FIG. 63). For example, a set shape of the flap members can be the closed position and the flap members can be help in the open position by a placement member. When the placement member is removed, the flap members can spring back toward the closed position from the open position.

An opening 6204 is provided at a center location between the flap members 6202. When one or more of the flap members 6202 are in the open position, the opening 6204 is configured such that the anchor member 6200 can be moved along a suture portion of an attachment member. When all of the flap members 6202 are in the closed position, the opening 6204 is configured to compress the suture portion of an attachment member such that the suture portion is constrained in a radial direction. The anchor member 6200 is deployed in the open position and moved to a desired location on a suture portion of an attachment member. Once the anchor member 6200 is in the desired position, the flap members 6202 are simultaneously moved from the open position to the closed position. The flap members 6202 provide a force in the radial direction to secure the attachment member to a tissue member (e.g., to secure the attachment member to the annulus of the mitral valve). Alternatively, the flap members 6202 can be moved from the open position to the closed position in a sequential order or random order. During this alternative procedure, a tortuous path is created with multiple holding points on the suture portion of the attachment member, which will increase the holding force on suture portions that have higher surface lubricities. The holding forces applied by the anchor member 6202, in effect, create a tourniquet around the suture portion. The anchor can be made from a wide variety of different materials. For example, the anchor member 6202 can be made from plastic, metal, such as steel, shape memory alloys, such as Nitinol, any combination of these materials, and the like. The anchor member can be deployed by any suitable device, such as, for example, any of the valve repair devices disclosed in the present application.

The anchor members 5900, 6200, as well as any other anchor members described in the present application, can be used to secure any of the attachment members described in the present application, and can be used in any of the procedures described in the present application. The anchor members 5900, 6200 can also be used in a wide variety of additional procedures. For example, the anchor members 5900, 6200 can be used in any procedure that involves approximating a tissue member. In addition, the anchor members 5900, 6200 can be used in any application that involves anchoring a suture member in a desired position. The anchor members 5900, 6200 can also be used with any type of suture member, such as, for example, any suture member described in the present application. The anchor members 5900, 6200 can be used in various applications for repairing or replacing native heart valves.

Referring to FIGS. 64A-64E and 65A-65C, in certain embodiments, the anchor member 6200 can be used with a protecting member 6400, 6500. The protecting member 6400, 6500 is configured to prevent friction between the anchor member 6200 and tissue 6403 (e.g., the annulus of the mitral valve), which prevents damage to the tissue. The protecting member 6400, 6500 also prevents surface damage to a suture portion 6405 of an attachment member (e.g., any of the attachment members described in the present application) as the attachment member is being held by the anchor member 6200.

Figure 64A:
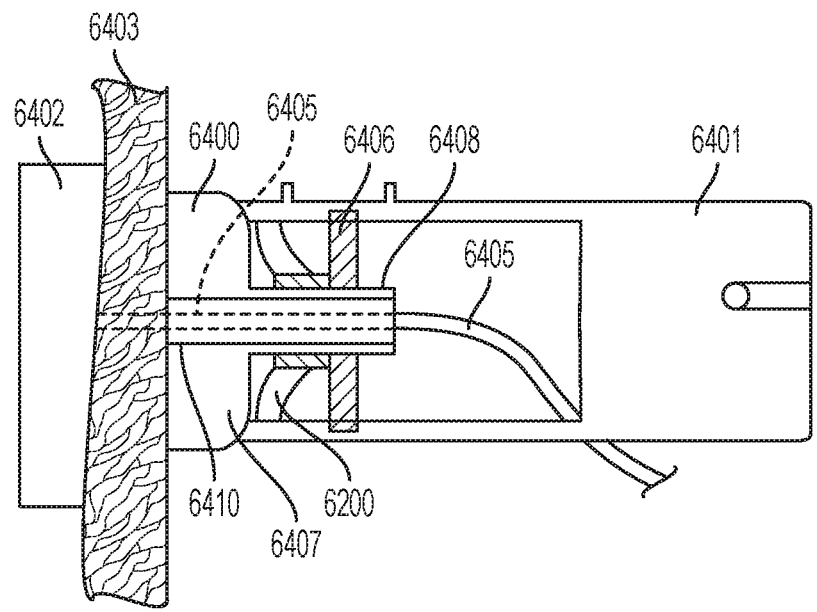
FIGS. 64A-64E illustrate an exemplary embodiment of a protecting member and an anchor member used for securing an attachment member to a tissue.

Referring to FIG. 64A, an exemplary embodiment of a device 6401 is shown securing an attachment member 6402 (e.g., any attachment member described in the present application), a protecting member 6400, and an anchor member 6200 to tissue 6403. The protecting member 6400 includes a first portion 6407, a second portion 6408, and a channel 6410 that extends through the first portion and the second portion. After an attachment member 6402 is placed in a desired position, the device 6401 is used to place the protecting member 6400 on the suture portion 6405 such that the suture portion extends through the channel 6410 and the protecting member can be moved along the suture portion 6405. That is, the channel 6410 of the protecting member 6400 is configured such that the protecting member can be moved along the suture portion 6405. The first portion 6407 of the protecting member 6400 is configured to engage the tissue 6403 in order to prevent potential damage to the tissue. The second portion 6408 of the protecting member 6400 is configured to be engaged by the anchor member 6200 to fix the protecting member in a desired location on the suture portion 6405. In certain embodiments, the protecting member 6400 is made from a compressive material that is able to be adequately compressed to retain the protecting member at a desired location on the suture portion 6405. For example, the protecting member 6400 is made from a material such that, when the anchor member engages the second portion 6408 of the protecting member, the anchor member 6200 compresses the channel 6410 such that the protecting member 6400 is prevented from moving along the suture portion 6405.

Figure 64B:
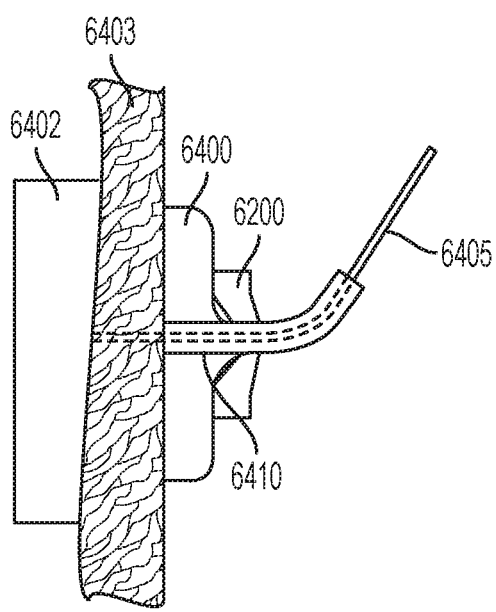

The device 6401 includes a placement member 6406 that is configured to maintain the anchor member 6200 in an open position as the device 6401 moves the anchor member and protecting member 6400 along the suture portion 6405 to a desired position (e.g., a position in which the protecting member is abutting the tissue 6403). Once the anchor member 6200 and the protecting member 6400 are in the desired position, the device 6401 allows a user to remove the placement member 6406 from engagement with the anchor member 6200 such that the anchor member is deployed from the device 6401 and moved from the open position to the closed position. Referring to FIG. 64B, the anchor member 6200 is shown in the closed position and engaging the second portion 6408 of the protecting member 6400 such that the protecting member is maintained in a desired position.

Figure 64C:
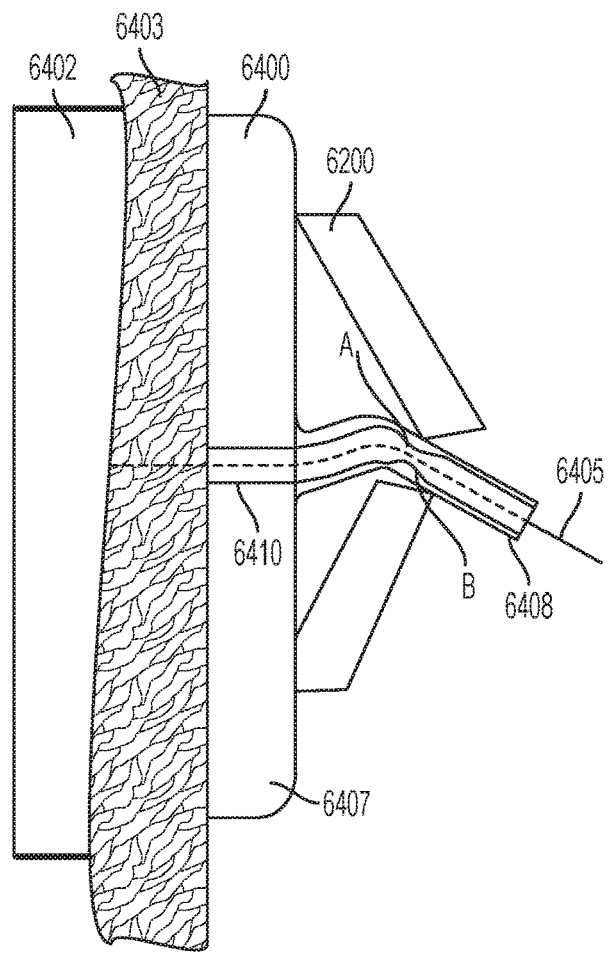
Figure 64D:
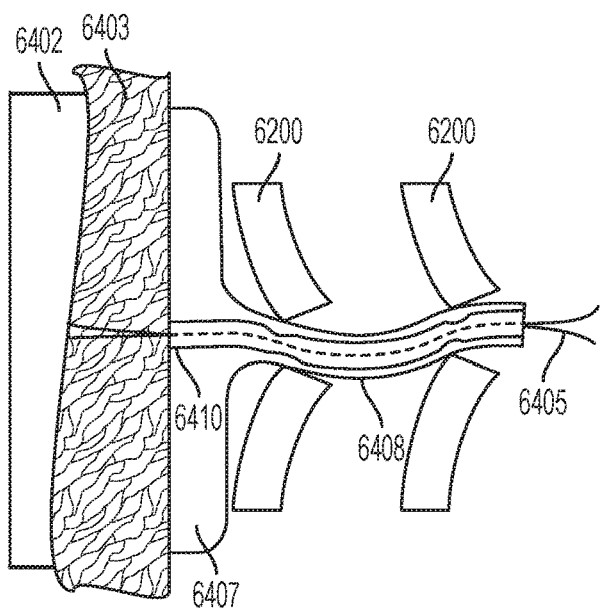

Referring to FIG. 64C, the anchor member 6200 is shown engaging the second portion 6408 of the protecting member 6400 such that a tortuous path is created with multiple holding points A, B on the suture portion 6405 of the attachment member 6402. The tortuous path increases the holding force on suture portions that have higher surface lubricities. Referring to FIG. 64D, in certain embodiments, two anchor members 6200 can be used to maintain the protecting member 6400 in a desired location on the suture portion 6405 of the attachment member 6402.

Figure 64E:
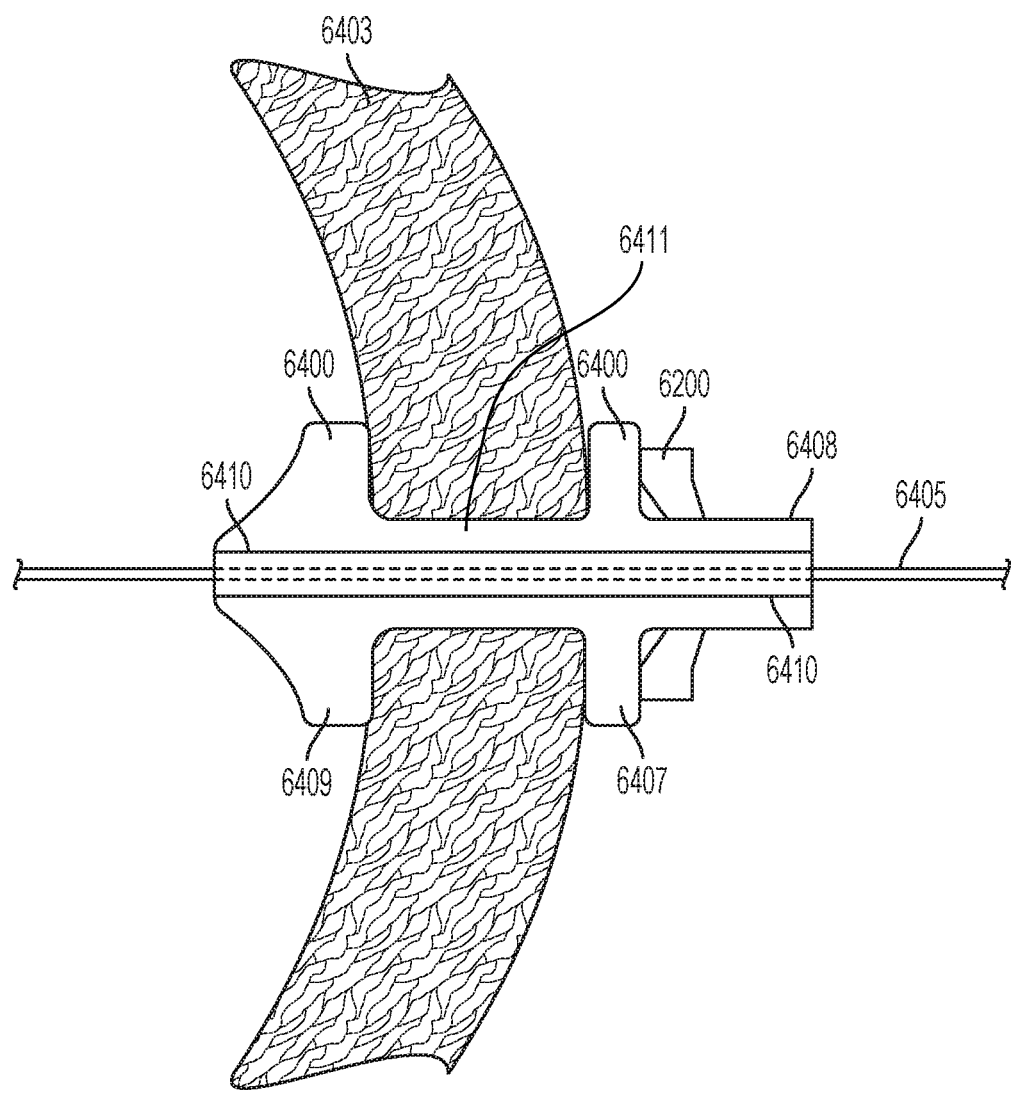

Referring to FIG. 64E, in some embodiments, the protecting member 6400 is configured to span a tissue wall 6403. That is, the protecting member 6400 may include a spanning portion 6411 that extends through the tissue wall and a third portion 6409 that is configured to engage the side of the tissue wall 6403 that is opposite the side of the tissue wall that the first portion 6407 engages. The spanning portion 6411 protects the tissue wall from abrasion or other damage by the suture. The third portion 6409 and the first portion 6407 "sandwich" the tissue wall 6403 to prevent relative movement between the protecting member and the tissue wall 6403.

Figure 65A:
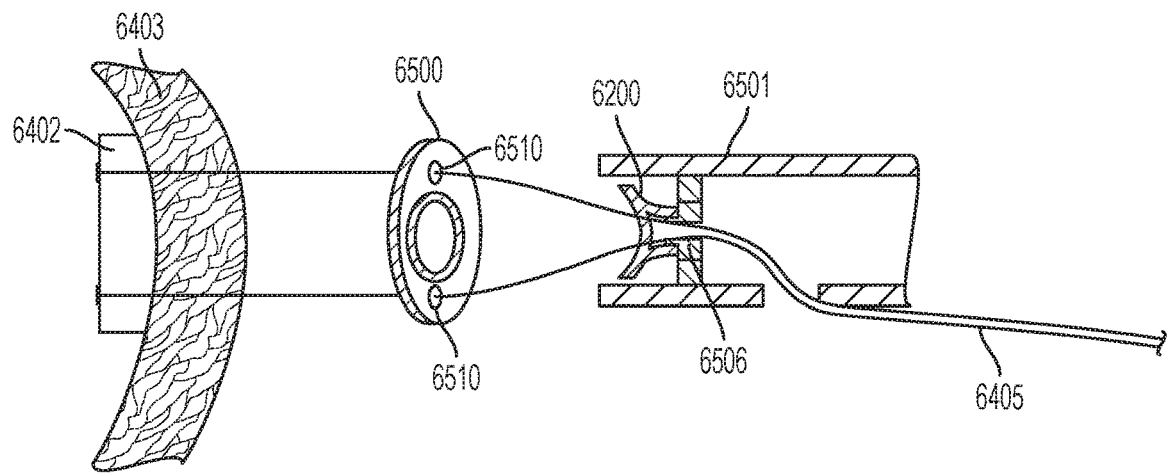
FIGS. 65A-65C illustrate another exemplary embodiment of a protecting member and an anchor member for securing an attachment member to tissue.
Figure 65B:
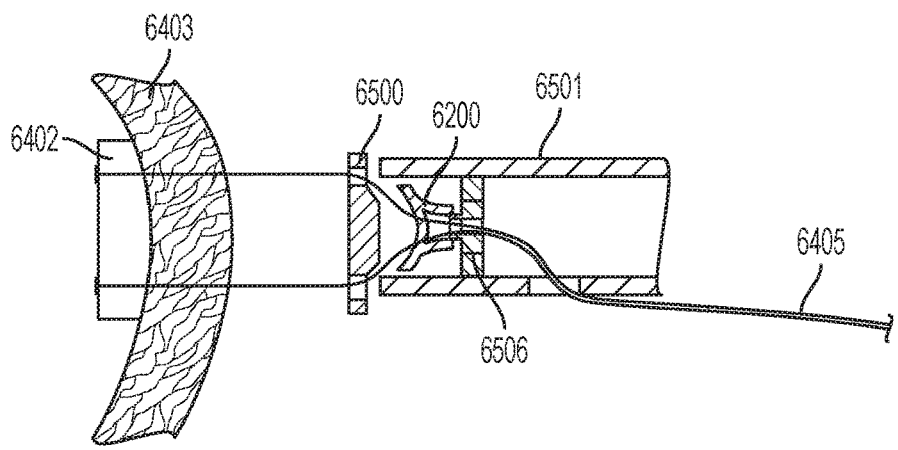

Referring to FIGS. 65A and 65B, an exemplary embodiment of a device 6501 is shown securing an attachment member 6402 (e.g., any attachment member described in the present application), another exemplary embodiment of a protecting member 6500, and an anchor member 6200 to a tissue member 6403. After an attachment member 6402 is placed in a desired position, the device 6501 is used to place the protecting member 6500 on the suture portion 6405 such that the suture portion extends through one or more apertures 6510 and the protecting member can be moved along the suture portion 6405. That is, the protecting member 6500 has one or more apertures 6510 that are configured to allow the protecting member to be moved along the suture portion 6405. In the illustrated embodiment, the protecting member 6500 has two apertures 6510. In alternative embodiments, the protecting member 6500 may have three apertures, four apertures, five apertures, etc. In some embodiments, side slots (not shown) can be incorporated into the apertures 6510 such that the protecting member 6500 can be installed on sutures with conventional knots or with alternative anchor members (e.g., any anchor member described in the present application. The protecting member 6500 is configured to redirect the tension on the suture portion 6405 away from the anchor member 6200 and onto the protecting member 6500. The protecting member 6500 can be designed with various support forms to assist in redirecting the tension on the suture portion. In certain embodiments, the protecting member 6500 is made from a lubricious material (e.g., ePTFE or the like) such that movement of the protecting member over the suture portion 6405 will not damage the suture portion.

Figure 65C:
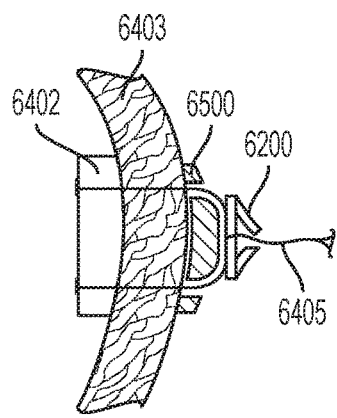

The device 6501 includes a placement member 6506 that is configured to maintain the anchor member 6200 in an open position as the device 6501 moves the anchor member and protecting member 6500 along the suture portion 6405 to a desired position (e.g., a position in which the protecting member is abutting the tissue member 6403). Once the anchor member 6200 and the protecting member 6500 are in the desired position, the device 6501 allows a user to remove the placement member 6506 from engagement with the anchor member 6200 such that the anchor member is deployed from the device 6501 and moved from the open position to the closed position. Referring to FIG. 65C, the anchor member 6200 is shown in the closed position and engaging the suture portion 6405 such that the protecting member 6500 is maintained in a desired position.

While the protecting members 6400, 6500 are shown being used with anchor member 6200, it should be understood that the protecting members 6400, 6500 can be used with any suitable anchor member. For example, the protecting members 6400 can be used with any anchor member described in the present application.

Figure 66:
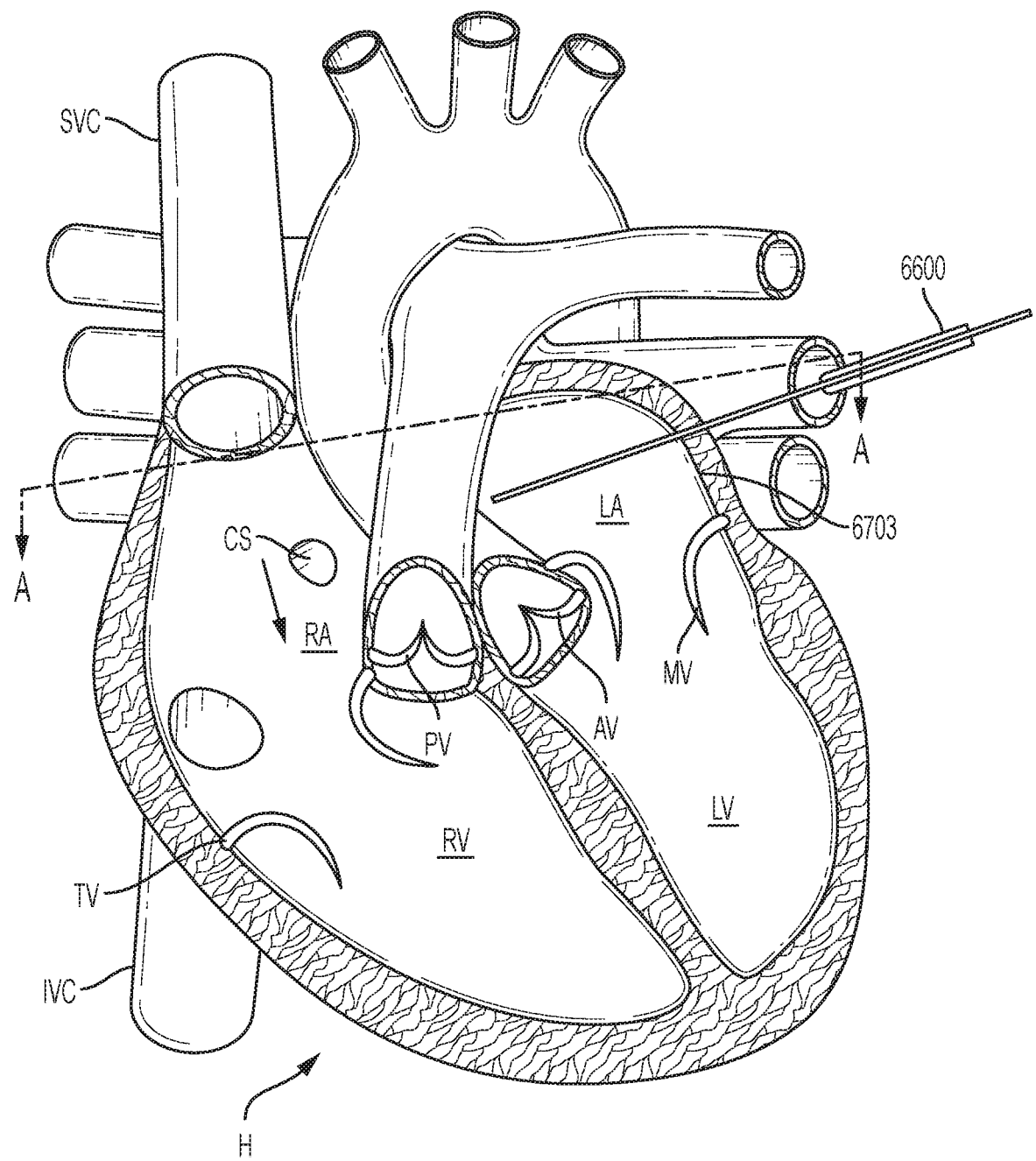
FIG. 66 is a cutaway view of the human heart showing an exemplary embodiment of a valve repair device entering the left atrium through an outer wall of the heart.
Figure 67A:
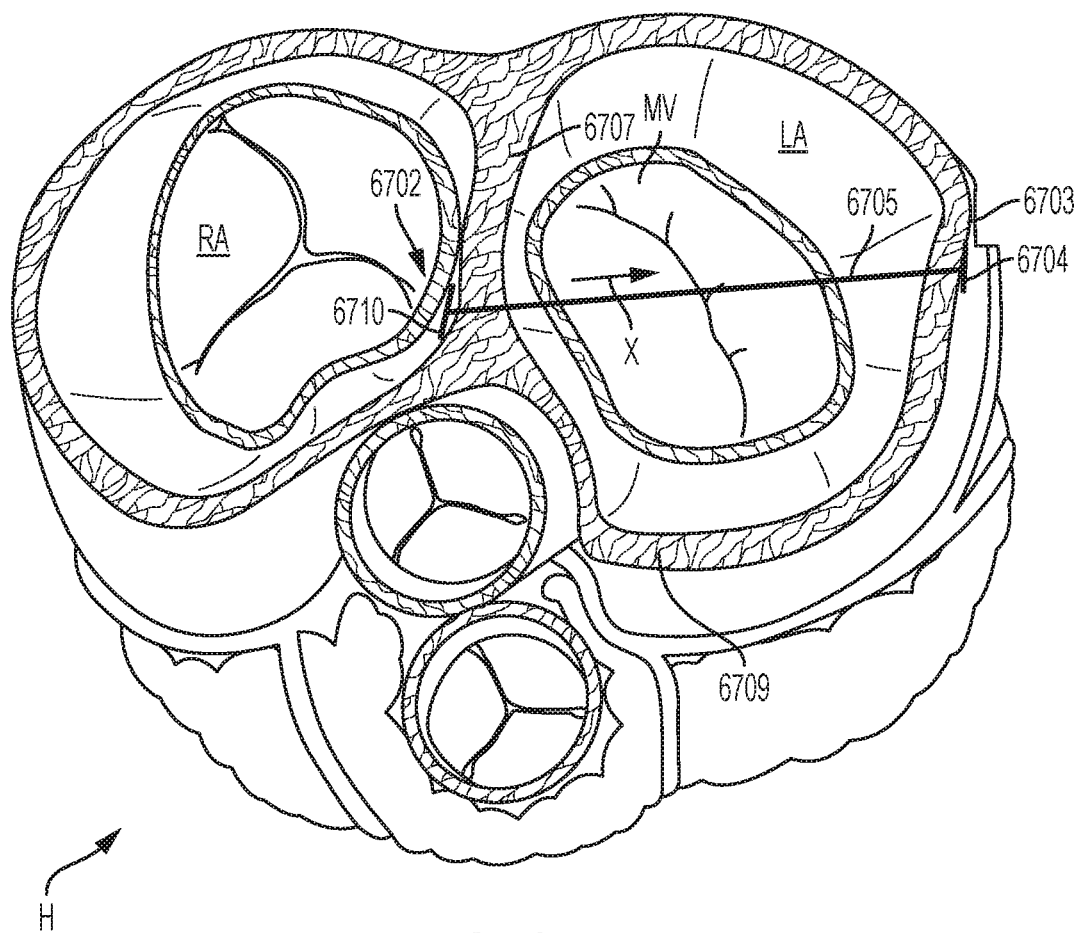
FIGS. 67A-67B illustrate the heart shown from the perspective shown by line A-A in FIG. 66 after repairing the mitral valve using the exemplary valve repair device shown in FIG. 66.
Figure 67B:
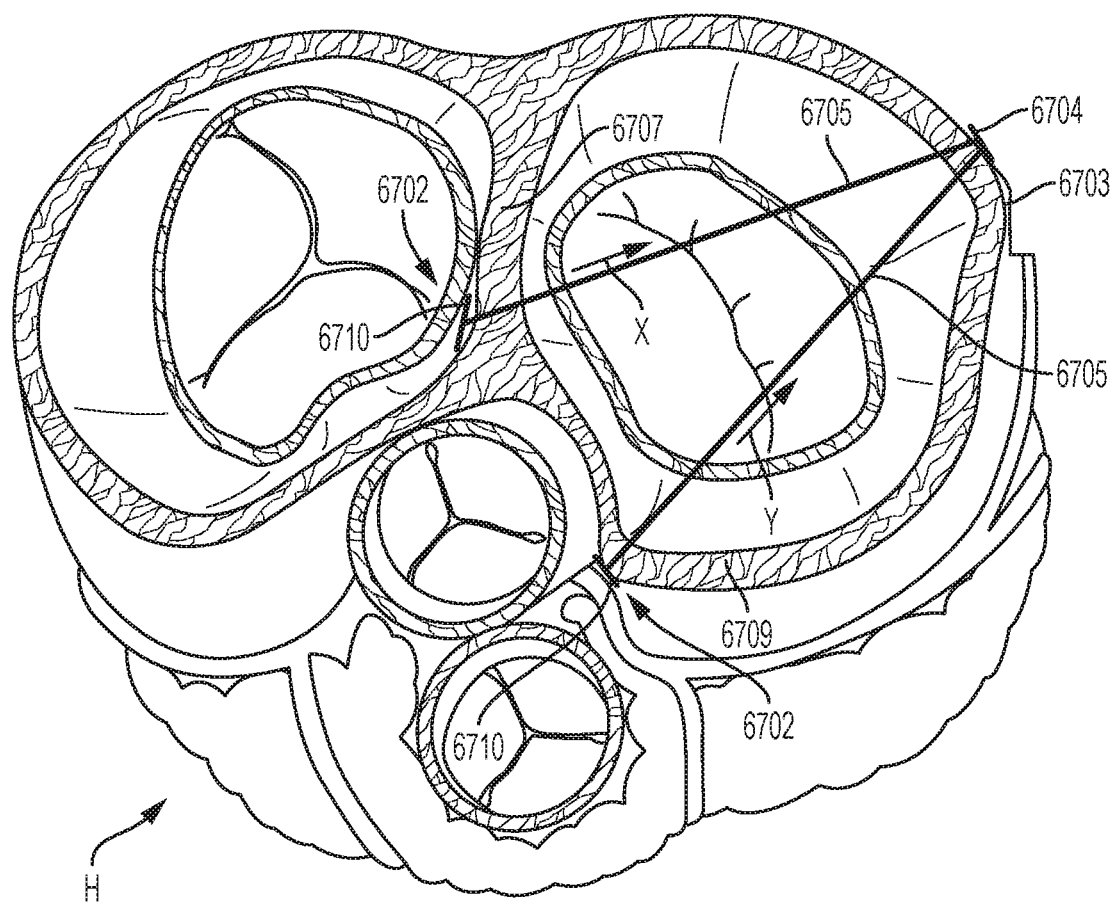

Referring to FIGS. 66 and 67A-67B, an exemplary procedure for mitral annuloplasty is a transatrial procedure using valve repair device 6600 to attach one or more attachment members 6702 to the heart H. Referring to FIG. 67A, in certain embodiments, the attachment member 6702 includes a securing portion 6710 and a suture portion 6705, and the suture portion is attached to the outer wall 6703 of the left atrium LA using an anchoring member 6704. In this embodiment, the anchoring member 6704 attaches the suture portion 6705 to the outer wall 6703 such that a force is applied to the securing portion 6710 of the attachment member 6702 to improve coaptation of the mitral valve MV and prevent regurgitation though the mitral valve MV. Referring to FIG. 67B, in some situations, more than one attachment member 6702 can be used to improve coaptation of the mitral valve and prevent regurgitation through the mitral valve MV. In the illustrate embodiment, two attachment members 6702 are used during the exemplary mitral annuloplasty procedure. The procedure, however, can include using any number of attachment members 6702, such as, for example, three attachment members, four attachment members, five attachment members, etc. Referring again to FIG. 67B, in this embodiment, the suture portion 6705 of both attachment members 6702 are attached to the outer wall 6703 of the left atrium LA using a single anchoring member 6704. In alternative embodiments, each attachment member 6702 may be secured to the outer wall of the left atrium LA by separate anchoring members 6704, or some attachment members 6702 may be secured by the same anchoring member 6704 and some attachment members may be secured by a separate anchoring member. The attachment members 6702 may take any suitable form, such as, for example, any form described in the present application. The anchoring members 6704 may take any suitable form, such as, for example, any form described in the present application.

Referring to FIG. 66, the valve repair device 6600 enters the left atrium LA through an outer wall 6703 of the heart H. After the valve repair device 6600 enters the left atrium LA, the repair device engages the atrial septum 6707 (FIGS. 67A and 67B) and/or the anterior wall 6709 (FIGS. 67A and 67B) of the left atrium. The valve repair device 6600 is configured to attach one or more attachment members to the heart H. The attachment members 6702 can be attached to the atrial septum 6707 in the right atrium RA and/or could terminate in the anterior wall 6709 of the left atrium LA. The valve repair device 6600 may take any suitable form that is capable of entering the left atrium LA through an outer wall 6703 of the heart H and attaching one or more attachment members to the heart H. For example, the valve repair device 6600 can take the form of the devices described in U.S. Pat. No. 7,635,386 and U.S. Patent Application Publication No. 2014/0114404 A1, which are hereby incorporated by reference in their entireties. In one embodiment, the device 6600 can take the form of the devices described in U.S. Patent Application Publication No. 2016/0008132 A1, which is incorporated herein by reference in its entirety, and the attachment member 6702 can be attached to the heart in any form described in this incorporated reference.

Referring to FIG. 67A, a single attachment member 6702 is used to repair the mitral valve MV. In this example, the securing portion 6710 of the attachment member 6702 is attached to the atrial septum 6707 and is disposed in the right atrium RA of the heart H. The suture portion 6705 of the attachment member extends from the securing portion 6710, through the atrial septum 6707, and through the outer wall 6709 of the left atrium LA. The suture portion 6705 is then secured to the outer wall 6703 of the left atrium LA of the heart H by an anchoring member 6704. The suture portion 6705 is secured such that a force is applied in the direction X to improve coaptation of the mitral valve MV and prevent regurgitation through the mitral valve MV.

Referring to FIG. 67B, one attachment member 6702 is attached to the atrial septum 6707 and disposed in the right atrium RA of the heart H, and another attachment member 6702 is terminated in the anterior wall 6709 of the left atrium LA of the heart H. The suture portion 6705 of each of these attachment members are secured to the outer wall 6703 of the left atrium LA by a single anchoring member 6704. In an alternative embodiment, the attachment members 6702 are secured by separate anchoring members. In the embodiment shown in FIG. 67B, one attachment member 6702 is secured such that a force is applied in the direction X, and the other attachment member 6702 is secured such that a force is applied in the direction Y. These forces improve coaptation of the mitral valve MV and prevent regurgitation through the mitral valve.

While the various devices and procedures described in the present application refer to engaging and repairing the mitral valve, or procedures for mitral annuloplasty, it should be understood that these devices and procedures can be used in repairing any other native valves (e.g., the tricuspid valve, the pulmonary valve, the aortic valve) or any other portion of the heart.

While the exemplary procedures provided in the present application may refer to a first step, a second step, etc., it should be understood that the steps of the procedure can be rearranged and/or intermediate steps can be included in the procedures.

While the foregoing is a complete description of the preferred embodiments, various alternatives, modifications, and equivalents can be used. Moreover, it will be obvious that certain other modifications can be practiced within the scope of the appended claims.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Depending on the embodiment, certain acts, events, or functions of any of the processes described herein can be performed in a different sequence, may be added, merged, or left out altogether. Thus, in certain embodiments, not all described acts or events are necessary for the practice of the processes.

Certain standard anatomical terms of location are used herein with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present. As used herein, the term "and/or" used between the last two of a list of elements means any one or more of the listed elements. For example, the phrase "A, B, and/or C" means "A," "B," "C," "A and B," "A and C," "B and C," or "A, B, and C."

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

The methods, operations, steps, etc. described herein can be performed on a living animal or on a non-living cadaver, cadaver heart, simulator (e.g., with the body parts, tissue, etc. being simulated), etc.

What is claimed is:

1. A method for repairing a native valve of a heart, the method comprising:
    accessing a ventricle of a heart with a valve repair device;
    puncturing, using a portion of the valve repair device, a first portion of a native valve from a ventricular side of the valve to access an atrial side of the valve;
    deploying a first tissue anchor on the atrial side of the valve, wherein a first suture portion extends from the first tissue anchor, through the first portion of the valve, and to a ventricular side of the valve;

withdrawing the portion of the valve repair device back through the first portion of the valve into the ventricle;

puncturing a second portion of the valve from the ventricular side of the valve to access the atrial side of the valve;

deploying a second tissue anchor on the atrial side of the valve, wherein a second suture portion extends from the second tissue anchor, through the second portion of the valve, and to the ventricular side of the valve;

applying a force to the first and second suture portions such that the first tissue anchor and the second tissue anchor are drawn relatively toward one another to a cinched position; and locking the first tissue anchor and the second tissue anchor in the cinched position using a suture-securing means.

2. The method of claim 1, wherein:
the valve is a mitral valve; and
the first and second portions of the valve are part of an annulus of the mitral valve.

3. The method of claim 2, wherein the first and second suture portions run along a ventricular side of the annulus.

4. The method of claim 3, wherein the first and second suture portions are part of a single strand of suture.

5. The method of claim 1, wherein the portion of the valve repair device comprises a needle tip configured to be deployed from a shaft of the valve repair device.

6. The method of claim 1, wherein the first and second tissue anchors comprise first and second pledgets.

7. The method of claim 2, wherein the force applied to the first and second suture portions causes a cinching effect on at least a portion of the annulus of the mitral valve.

8. The method of claim 1, wherein the first and second tissue anchors comprise T-shaped members.

9. The method of claim 6, wherein the first suture portion is secured to the first pledget by a knot on a distal side of the first pledget.

10. The method of claim 8, wherein the T-shaped members each comprise a main body portion, a tab portion, and a suture-attachment aperture through which a respective suture portion is disposed.

11. A method for repairing a mitral valve, the method comprising:

inserting a valve repair device into a left ventricle of a heart of a patient, wherein two or more tissue anchors are disposed in a shaft of the valve repair device, the two or more tissue anchors being coupled by a suture;

engaging a ventricle side of an annulus of the mitral valve with the valve repair device;

deploying first and second tissue anchors of the two or more tissue anchors on an atrium side of the annulus of the mitral valve such that a first portion of the suture that is coupled between the first and second tissue anchors passes between the first and second tissue anchors along a first annular segment of the ventricle side of the annulus;

applying a force to the suture to cause a cinching effect on at least a portion of the annulus; and fixing the suture such that the two or more tissue anchors and the suture maintain the cinching effect.

12. The method of claim 11, wherein each of the two or more tissue anchors is associated with a suture portion that extends from the respective tissue anchor, through the annulus, and along at least an annular portion the annulus.

13. The method of claim 12, wherein the force is applied to an excess portion of the suture that is not coupled between the first and second tissue anchors.

14. The method of claim 12, wherein the suture is further coupled between the second tissue anchor and a third tissue anchor disposed on the atrium side of the annulus by a portion of the suture that runs along a second annular segment of the annulus on the ventricle side of the annulus.

15. The method of claim 14, wherein the first, second, and third tissue anchors are secured in relative position by a single suture-securing means associated with the suture.

16. The method of claim 1, wherein the suture-securing means comprises at least one of a knot, a clasp, a lock, or a fastener.

17. A method for repairing a mitral valve, the method comprising:

inserting a valve repair device into a heart, the valve repair device comprising a delivery member having an outlet, a puncturing member, and an advancement member configured to move two or more tissue anchors connected by a suture out of the outlet of the delivery member;

puncturing a first location of an annulus of the mitral valve with the puncturing member of the valve repair device, such that the outlet of the delivery member of the valve repair device moves from a first side of the annulus to a second side of the annulus;

deploying a first tissue anchor of the two or more tissue anchors out of the outlet of delivery member of the valve repair device, such that the first tissue anchor abuts the second side of the annulus;

moving the outlet of the delivery member of the valve repair device from the second side of the annulus to the first side of the annulus, such that the suture extends from the first tissue anchor, through the annulus, and outward from the first side of the annulus;

puncturing a second location of the annulus of the mitral valve with the puncturing member of the valve repair device, such that the outlet of the delivery member of the valve repair device moves from the first side of the annulus to the second side of the annulus, and such that the suture runs along an annular segment of the annulus on the first side of the annulus and extends through the annulus and outward from the second side of the annulus;

deploying a second tissue anchor of the two or more tissue anchors out of the outlet of the delivery member of the valve repair device, such that the second tissue anchor abuts the second side of the annulus;

moving the outlet of the delivery member of the valve repair device from the second side of the annulus to the first side of the annulus, such that the suture extends from the second tissue anchor, through the annulus, and outward from the first side of the annulus;

applying a force to the suture such that the two or more tissue anchors cause a cinching effect on the annular segment of the annulus of the mitral valve; and securing the suture to maintain the cinching effect.

18. The method of claim 17, wherein the puncturing member of the valve repair device comprises a needle.

19. The method of any of claim 17, wherein the puncturing member of the valve repair device is retractable.

20. The method of claim 1, wherein the first and second tissue anchors comprise knot suture forms.

* * * * *